(12) United States Patent
Liu et al.

(10) Patent No.: US 11,623,091 B2
(45) Date of Patent: Apr. 11, 2023

(54) PORTABLE ELECTRICAL STIMULATION SYSTEM AND METHOD

(71) Applicant: Avent, Inc., Alpharetta, GA (US)

(72) Inventors: Wanzhan Liu, Alpharetta, GA (US);
Chris Zobkiw, Alpharetta, GA (US);
Gleb Klimovitch, Alpharetta, GA (US);
Ryan Caldwell, Alpharetta, GA (US);
Eric A. Schepis, Alpharetta, GA (US);
Phillip A. Schorr, Alpharetta, GA (US);
Jalpa Shah, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 289 days.

(21) Appl. No.: 16/790,713

(22) Filed: Feb. 13, 2020

(65) Prior Publication Data
US 2020/0254257 A1 Aug. 13, 2020

Related U.S. Application Data

(60) Provisional application No. 62/819,475, filed on Mar. 15, 2019, provisional application No. 62/805,019, filed on Feb. 13, 2019.

(51) Int. Cl.
*A61N 1/36* (2006.01)
*A61N 1/05* (2006.01)

(52) U.S. Cl.
CPC ....... *A61N 1/36071* (2013.01); *A61N 1/0551* (2013.01); *A61N 1/36017* (2013.01); *A61N 1/36021* (2013.01)

(58) Field of Classification Search
CPC .............. A61N 1/36071; A61N 1/0551; A61N 1/36017; A61N 1/36021; A61N 1/025; A61N 1/0502; A61N 1/06; A61N 1/3603
See application file for complete search history.

(56) References Cited

U.S. PATENT DOCUMENTS

| | | |
|---|---|---|
| 5,344,438 A | 9/1994 | Testerman et al. |
| 5,755,750 A | 5/1998 | Petruska et al. |
| | (Continued) | |

FOREIGN PATENT DOCUMENTS

| | | |
|---|---|---|
| WO | 2006/029257 | 3/2006 |
| WO | 2008/106174 | 9/2008 |
| | (Continued) | |

OTHER PUBLICATIONS

International Search Report and Written Opinion dated Jun. 30, 2020, from International Application No. PCT/US2020/018196, 14 pages.

(Continued)

*Primary Examiner* — Mark W. Bockelman
(74) *Attorney, Agent, or Firm* — Meunier Carlin & Curfman LLC

(57) ABSTRACT

The present disclosure is directed to a portable system and method for modulating targeted neural and non-neural tissue of a nervous system to block nerve conduction for the treatment of pain. A high-efficiency portable electrical stimulation system is provided that allows a user to carry the system and move around freely while continuously receiving therapy. The electronic control system is configured to deliver high-frequency electrical stimulation at a therapeutic level, for an intended duration (e.g., up to 24 hours or more) at a manageable and/or comfortable weight for a person, to the target nerve.

19 Claims, 41 Drawing Sheets

(56) References Cited

U.S. PATENT DOCUMENTS

| | | |
|---|---|---|
| 6,981,967 B2 | 1/2006 | Massengale et al. |
| 7,389,145 B2 | 6/2008 | Kilgore et al. |
| 8,027,718 B2 | 9/2011 | Spinner et al. |
| 8,060,208 B2 | 11/2011 | Kilgore et al. |
| 8,463,383 B2 | 6/2013 | Sakai et al. |
| 8,612,020 B2 | 12/2013 | Donofrio |
| 8,700,177 B2 | 4/2014 | Strother et al. |
| 8,731,676 B2 | 5/2014 | Fang et al. |
| 8,751,009 B2 | 6/2014 | Wacnik |
| 8,843,188 B2 | 9/2014 | Kilgore et al. |
| 8,855,776 B2 | 10/2014 | Lin et al. |
| 8,965,516 B2 | 2/2015 | Bennett et al. |
| 8,983,612 B2 | 3/2015 | Fang et al. |
| 8,983,614 B2 | 3/2015 | Kilgore et al. |
| 9,008,800 B2 | 4/2015 | Ackermann, Jr. et al. |
| 9,037,248 B2 | 5/2015 | Durand et al. |
| 9,119,966 B2 | 9/2015 | Franke et al. |
| RE45,718 E | 10/2015 | Kilgore et al. |
| 9,205,258 B2 | 12/2015 | Simon et al. |
| 9,205,265 B2 | 12/2015 | Franke |
| 9,248,289 B2 | 2/2016 | Bennett et al. |
| 9,259,571 B2 | 2/2016 | Straka et al. |
| 9,259,578 B2 | 2/2016 | Torgerson |
| 9,295,841 B2 | 3/2016 | Fang et al. |
| 9,333,356 B2 | 5/2016 | Franke et al. |
| 9,339,647 B2 | 5/2016 | Strother et al. |
| 9,358,374 B2 | 6/2016 | Dacey, Jr. et al. |
| 9,364,661 B2 | 6/2016 | Kilgore et al. |
| 9,387,322 B2 | 7/2016 | Bhadra et al. |
| 9,403,014 B2 | 8/2016 | Kilgore et al. |
| 9,409,020 B2 | 8/2016 | Parker |
| 9,415,211 B2 | 8/2016 | Bradley et al. |
| 9,498,621 B2 | 11/2016 | Ackermann et al. |
| 9,555,245 B2 | 1/2017 | Boggs, II et al. |
| 9,566,426 B2 | 2/2017 | Simon et al. |
| 9,636,497 B2 | 5/2017 | Bradley et al. |
| 9,694,181 B2 | 7/2017 | Bhadra et al. |
| 9,707,394 B2 | 7/2017 | Bennett et al. |
| 9,884,192 B2 | 2/2018 | Kilgore et al. |
| 9,889,291 B2 | 2/2018 | Bhadra et al. |
| 10,039,917 B2 | 8/2018 | Kilgore et al. |
| 10,071,241 B2 | 9/2018 | Bhadra et al. |
| 10,195,434 B2 | 2/2019 | Bhadra et al. |
| 2005/0197678 A1 | 9/2005 | Boveja et al. |
| 2007/0191915 A1 | 8/2007 | Strother |
| 2008/0027505 A1 | 1/2008 | Levin et al. |
| 2008/0071321 A1 | 3/2008 | Boggs, II et al. |
| 2008/0132962 A1 | 6/2008 | Diubaldi |
| 2008/0208287 A1 | 8/2008 | Palermo et al. |
| 2008/0294221 A1 | 11/2008 | Kilgore |
| 2009/0259279 A1 | 10/2009 | Dobak, III |
| 2010/0152808 A1 | 6/2010 | Boggs, II |
| 2010/0191311 A1 | 7/2010 | Scheiner et al. |
| 2010/0274318 A1 | 10/2010 | Walker et al. |
| 2012/0277823 A1 | 11/2012 | Gerber et al. |
| 2012/0290053 A1 | 11/2012 | Zhang et al. |
| 2012/0296389 A1 | 11/2012 | Fang et al. |
| 2013/0066393 A1 | 3/2013 | Gross et al. |
| 2013/0116752 A1 | 5/2013 | Parker et al. |
| 2013/0138193 A1 | 5/2013 | Durand et al. |
| 2013/0238066 A1 | 9/2013 | Boggs, II et al. |
| 2013/0261697 A1 | 10/2013 | Parker |
| 2013/0296966 A1 | 11/2013 | Wongsarnpigoon et al. |
| 2014/0058495 A1 | 2/2014 | Sakai et al. |
| 2014/0163660 A1 | 6/2014 | Fang et al. |
| 2014/0324129 A1 | 10/2014 | Franke et al. |
| 2014/0343655 A1 | 11/2014 | Rao et al. |
| 2014/0358191 A1 | 12/2014 | Kilgore et al. |
| 2015/0100106 A1 | 4/2015 | Shishilla et al. |
| 2015/0174397 A1 | 6/2015 | Bhadra et al. |
| 2015/0182742 A1 | 7/2015 | Ackermann et al. |
| 2015/0238764 A1 | 8/2015 | Franke |
| 2015/0320481 A1 | 11/2015 | Cosman, Jr. et al. |
| 2016/0030408 A1 | 2/2016 | Levin |
| 2016/0213927 A1 | 7/2016 | McGee et al. |
| 2016/0235969 A1 | 8/2016 | Kilgore et al. |
| 2016/0331976 A1 | 11/2016 | Kilgore et al. |
| 2016/0339241 A1 | 11/2016 | Hargrove et al. |
| 2017/0173329 A1 | 6/2017 | Boggs, II et al. |
| 2017/0197079 A1 | 7/2017 | Illegems et al. |
| 2017/0224989 A1 | 8/2017 | Schepis et al. |
| 2017/0246453 A1 | 8/2017 | Fang et al. |
| 2017/0312523 A1 | 11/2017 | Bennett et al. |
| 2018/0085587 A1 | 3/2018 | Kilgore et al. |
| 2018/0250506 A1 | 9/2018 | Kilgore et al. |
| 2018/0256886 A1 | 9/2018 | Bhadra et al. |
| 2018/0361155 A1 | 12/2018 | Bhadra et al. |
| 2019/0060640 A1 | 2/2019 | Bhadra et al. |
| 2019/0282809 A1 | 9/2019 | Schepis et al. |
| 2019/0282810 A1 | 9/2019 | Schepis et al. |

FOREIGN PATENT DOCUMENTS

| | | |
|---|---|---|
| WO | 2009/061813 | 5/2009 |
| WO | 2012/021583 | 2/2012 |
| WO | 2012/159002 | 11/2012 |
| WO | 2014/126718 | 8/2014 |
| WO | 2015/003561 | 1/2015 |
| WO | 2016/032929 | 3/2016 |
| WO | 2016/039768 | 3/2016 |
| WO | 2016/094728 | 6/2016 |
| WO | 2017/044542 | 3/2017 |
| WO | 2017/066734 | 4/2017 |
| WO | 2018/075473 | 4/2018 |
| WO | 2018/085611 | 5/2018 |

OTHER PUBLICATIONS

Joseph et al., High-Frequency Stimulation Selectively Block Different Types of Fibers in Frog Sciatic Nerve. IEEE Transactions on Neural Systems and Rehabilitaion Eng. 19(5), 2011, 8 pages.

Kilgore, et al., Reversible Nerve Conduction Block Using Kilohertz Frequency Alternating Current. Neuromodulation: Technology at the Neural Interface, 17(3):242-255 (2013).

Franke Manfred, et al. "Combined KHFAC+ DC nerve block without onset or reduced nerve conductivity after block." Journal of neural engineering 11.5 (2014):056012.

Frahm, Ken Steffen, et al. "Nerve fiber activation during peripheral nerve field stimulation: importance of electrode orientation and estimation of area of paresthesia." Neuromodulation: Technology at the Neural Interface 19.3 (2016):B11-318. Abstract.

Kapural et al.; "Novel 10-kHz High-frequency Therapy (HFIO Therapy) Is Superior to Traditional Low-frequency Spinal Cord Stimulation for the Treatment of Chronic Back and Leg Pain"; Anesthesiology 2015, Dated: 2015; 11 pages.

Finch et al.; "High-Frequency (10 kHz) Electrical Stimulation of Peripheral Nerves for Treating Chronic Pain: A Double-Blind Trial of Presence vs Absence of Stimulation"; Neuromodulation 2018; Dated: 2018; 8 pages.

International Search Report and Written Opinion issued for Application No. PCT/US2019/022626, dated Oct. 23, 2019.

Office Action issued for U.S. Appl. No. 16/355,673, dated Sep. 11, 2019.

Office Action issued for U.S. Appl. No. 16/355,673, dated Dec. 18, 2019.

Notice of Allowance issued for U.S. Appl. No. 16/355,673, dated Apr. 16, 2020.

Office Action issued for U.S. Appl. No. 16/355,651, dated Aug. 26, 2019.

Office Action issued for U.S. Appl. No. 16/355,651, dated Feb. 7, 2020.

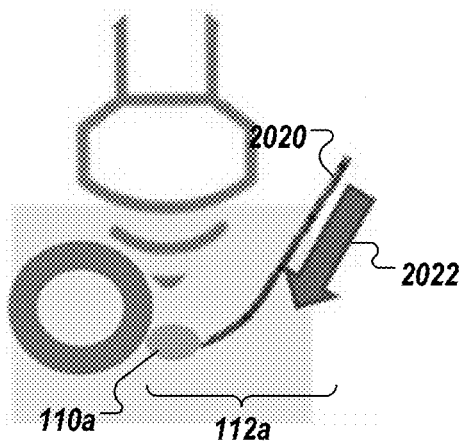
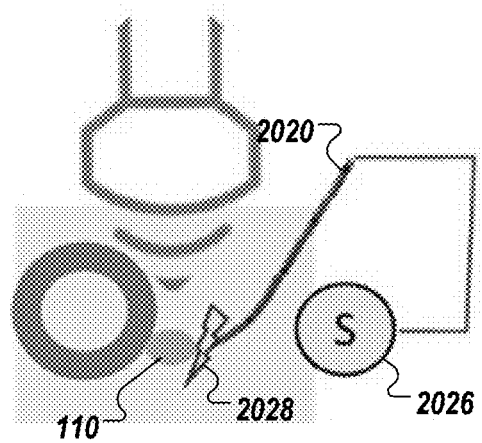
FIG. 21A
FIG. 21B
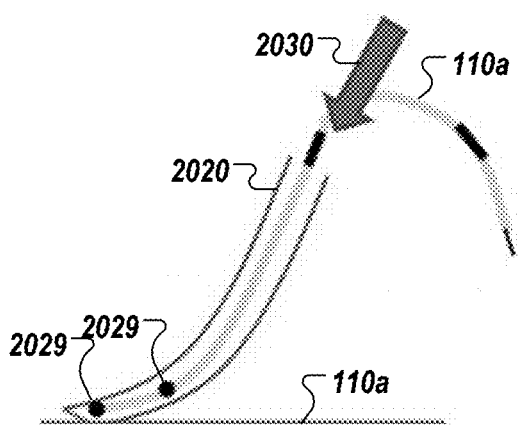
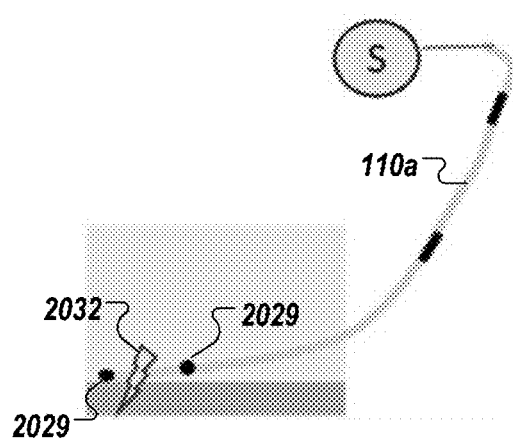
FIG. 21C
FIG. 21D

PORTABLE ELECTRICAL STIMULATION SYSTEM AND METHOD

RELATED APPLICATION

This application claims priority to, and the benefit of, U.S. Provisional Application No. 62/805,019, filed Feb. 13, 2019, entitled "Portable Electrical Stimulation System and Method" and U.S. Provisional Application No. 62/819,475, filed Mar. 15, 2019, entitled "Portable Electrical Stimulation System and Method", each of which is incorporated by reference herein in its entirety.

FIELD OF THE INVENTION

The present invention relates generally to a device and method to modulate neural and non-neural tissue activity using high-frequency electrical stimulation to block nerve conduction, e.g., treat pain.

BACKGROUND OF THE INVENTION

Pain can be treated by destructive and non-destructive methods that interfere with the transmission of pain signals sent to the brain. Destructive methods, such as radiofrequency ablation, are treatments of last resort, and are typically not used for treating acute (i.e., post-surgical) pain. Non-destructive methods to treat pain include the use of local anesthetic injections and electrical stimulation.

Two types of electrical stimulation have been used to treat pain originating from the periphery: (1) conventional stimulation, and (2) high-frequency stimulation. Conventional electrical stimulation (e.g., stimulation at less than 1 KHz) of a peripheral nerve has been used to treat chronic pain and generally involves attenuating or reducing perception of the pain by eliciting a sensory paresthesia within the receptive field of the treated nerve. Several high-frequency electrical stimulation are known. One type of high-frequency stimulation delivers electrical stimulation (e.g., often to the spine) that is below the subsensory threshold to attenuate the pain without causing paresthesia. Such high-frequency and conventional electrical stimulation treatment do not fully block nerve conduction as a means to treat pain. Another type of high-frequency stimulation has been used to treat post-amputation pain in people but requires open surgical procedures to place electrode in direct physical contact with a target nerve or complex-shaped leads around the nerve. Further, the usability of high-frequency electrical stimulation is challenged by "onset activity" and the "co-excitation" of nearby excitable tissues. Further, high-frequency electrical stimulation operation, in portable devices, also pose challenges associated with ease of use and battery life.

SUMMARY OF THE INVENTION

The present disclosure is directed to a portable system and method for modulating (e.g., reversibly and temporarily modulating) targeted neural and non-neural tissue of a nervous system to block nerve conduction for the treatment of pain. A high-efficiency portable electrical stimulation system is provided that allows a user to carry the system and move around freely while continuously receiving therapy. The electronic control system is configured to deliver high-frequency electrical stimulation at a therapeutic level, for an intended duration (e.g., up to 24 hours or more) at a manageable and/or comfortable weight for a person, to the target nerve. The high-frequency electrical stimulation is applied from one or more electrodes located on a percutaneous lead that are placed in parallel, or substantially in parallel, and without direct contact, to a long axis of the peripheral nerve over an overlapping nerve region of greater than about 3 millimeters, e.g. to provide a disruptive charge that produces an effect over several nodes of Ranvier of the target nerve. The electrical stimulation has, in some embodiments, a fundamental frequency harmonics that is greater than about 1.5 kilohertz and less than about 75 kilohertz, though other frequencies may be used as described herein. Percutaneous lead can be more readily positioned at the specified or intended position relative to the target nerve without need to complex paddle lead structures.

In some embodiments, the exemplary system is used as a drug-free (e.g., narcotic free) electric nerve block, e.g., for clinical or non-clinical settings, for perioperative pain management, e.g., to provide symptomatic relief of post-operative acute pain. In some embodiments, the exemplary system is configured for use with infusion pump system that controls flow of anesthetic medication to percutaneous catheter delivered to a wound site. In some embodiments, the system is configured as a single use, disposable device. In other embodiments, the system is configured such that the electronic portion of the system can be reused (e.g., for another set of patients or therapy session).

The complete block of nerve conduction, or a sufficient partial block of it, also ensures that the patient does not feel any pain or discomfort. Further, without having to directly contact the target nerve, the exemplified system and method provides a large delivery window for the percutaneous electrode to be placed without requiring an open surgical procedure. It is observed that this method completely and consistently blocks nerve conduction through the overlapping nerve region, thereby arresting any conduction, e.g., of pain sensation from regions of the body downstream of the overlapping nerve region. Indeed, the percutaneous electrode when deployed in such orientation can facilitate complete, or near complete, block of nerve conduction. The exemplified system and method can be further configured to block nerve condition without eliciting onset activity and co-excitation of non-targeted structures.

In an aspect, a portable electrical stimulation system is disclosed configured to percutaneously block nerve conduction (e.g., to inhibit a user's perception of pain), the system comprising a modular power source (e.g., rechargeable or non-rechargeable batteries); a switching circuit coupled to said modular power source and configured to continuously generate at an output of said switching circuit an electrical stimulation output at a plurality of selectable output level (e.g., amplitude level, duty cycle, or frequency) that spans over a range of output levels that can block nerve conduction (e.g., to inhibit a subject's perception of pain); and a controller coupled to the switching circuit, the switching circuit having one or a programmable output level, wherein the output of the switching circuit is coupled to one or more electrodes, directly or through a cable, located at, or in proximity to, the target site, wherein the one or more electrodes are placed in parallel, or substantially in parallel to a long axis of a peripheral nerve over an overlapping nerve region of greater than about 3 millimeters (e.g., wherein an electrical field generated between an electrode of the one or more electrodes and the overlapping nerve region from the application of the electrical stimulation sufficiently blocks nerve conduction through the overlapping nerve region).

In some embodiments, the switching circuit configured to continuously generate the electrical stimulation output at an output efficiency greater than 70%.

In some embodiments, the switching circuit configured to continuously generate the electrical stimulation output at an output efficiency greater than 90%.

In some embodiments, the switching circuit comprises a switching stage (e.g., comprising a first switching element coupled to a second switching element between a power source and ground sink) and a filter stage, the switching stage being configured to generate a square-wave amplitude modulated output, the filter stage being configured to shape the square wave amplitude modulated output to a sinusoidal waveform.

In some embodiments, the filter stage includes inductive and capacitive components with a high-quality factor (e.g., low resistive losses) at an operating frequency output of the sinusoidal waveform between 1.5 kHz and 75 kHz.

In some embodiments, the switching circuit comprises a variable output power source, the variable output power source comprising a linear regulator configured to vary the power source to the switching stage to vary the amplitude of the square-wave amplitude modulated output or the pulse-shaped amplitude modulated output.

In some embodiments, the switching circuit comprises a variable output power source, the variable output power source comprising a switching power regulator to vary the power source to the switching stage to vary the amplitude of the square-wave amplitude modulated output or the pulse-shaped amplitude modulated output.

In some embodiments, the switching circuit comprises a variable output power source, the variable output power source comprising any combination of linear regulator and switching power regulator to vary the power source to the switching stage to vary the amplitude of the square-wave amplitude modulated output or the pulse-shaped amplitude modulated output.

In some embodiments, the switching circuit comprises one or more feedback loops (e.g., voltage envelope sensing and current sensing), the controller being configured to vary the pulse-shaped amplitude modulated output based on a detected envelope of the square-wave amplitude modulated output or the pulse-shaped amplitude modulated output.

In some embodiments, the portable electrical stimulation system further includes a second modular power source, wherein the second modular power source has sufficient stored electrical energy to continuously generate the electrical stimulation output for a temporary period (e.g., less than 10 minutes); and a breaker to connect the switching circuit to the second modular power source and to isolate the modular power source during the temporary period without interruption (e.g., without interruption to the electrical stimulation output or with limited interruption to the electrical stimulation output such that the interruption does not interrupt an associated treatment).

In some embodiments, the controller comprises a display, the controller being configured present, via the display, the selected output level (e.g., selected intensity control value) or a monitored output level of the electrical stimulation output (e.g., as a percentage of maximum output).

In some embodiments, the controller comprises a speaker, the controller being configured to monitor for interruption of the electrical stimulation output when operating in a stimulation mode, and to generate an audible alert, via the speaker, upon detection of an interruption of the electrical stimulation output while in the stimulation mode.

In some embodiments, the switching circuit comprises a circuit to detect phasor magnitude load impedance between a pair of electrodes (e.g., percutaneous electrodes), and wherein the controller is configured to monitor (e.g., at start-up and at intermittent time during deployment, e.g., every 15 minutes) a detected phasor magnitude load impedance and to output an alert when the detected phasor magnitude load impedance exceeds a specified threshold.

In some embodiments, the controller is configured to vary one or more control parameters (output intensity, waveform frequency output, waveform duty cycle) associated with the electrical stimulation output based on the detected phasor magnitude load impedance.

In some embodiments, the portable electrical stimulation system has a weight that is less than 600 grams and has a volume that is less than 600 milliliters.

In some embodiments, the switch circuit comprises a first fault safety switch at a first output and a second fault safety switch at a second output, wherein each of the first fault safety switch and the second fault safety switch is configured to isolate the switch circuit from the pair of electrodes.

In some embodiments, one of the switching circuit comprises a fault safety switch (e.g., for one of a pair of electrodes).

In some embodiments, the switch circuit comprises a fault safety switch, wherein the fault safety switch is coupled between the modular power source and active output components to isolate the power source from the active output components and the electrode circuits when a circuit fault is detected.

In some embodiments, the controller comprises a display and a monitoring circuit, wherein the monitoring circuit is configured to monitor a battery state of the modular power source, and wherein the controller is configured to present, via the display, a remaining battery life or a remaining operating time based on the monitored battery state.

In some embodiments, the controller comprises persistent, non-volatile memory, the controller being configured to log, at pre-defined intermittent duration, one or more parameters selected from the group consisting of a first set of one or more parameters associated with the electrical stimulation output, a second set of one or more parameters associated with switching circuit, controller, or modular power source, a third set of one or more parameters associated with lead coupled to the switching circuit, a fourth set of one or more parameters associated with electrodes coupled to the switching circuit, and a fifth set of one or more parameters associated software status.

In some embodiments, the switch circuit comprises a high impedance differential voltage sensing circuit and a variable DC current injection circuit, wherein the differential voltage sensing circuit is configured to measure differential DC voltage at the pair of electrodes, and wherein the variable DC current injection circuit is configured to inject a current between the pair of electrodes to counteract any excess DC voltages based on the measured differential DC voltage.

In some embodiments, the switch circuit is configured to continuously output the electrical stimulation output over, at least, a 24-hour duration using the modular power source without replacement or recharge of the modular power source.

In some embodiments, the portable electrical stimulation system further includes one or more bypass filter circuits coupled to the switch circuits, and a connection element coupled to the one or more bypass filter circuits, wherein the connection element is configured to be coupled to electrodes, directly or through the cable, with the electrodes (e.g., wherein the square wave amplitude modulated output or pulse-shaped amplitude modulated output can be sent directly to tissue, e.g. for detecting nerve location and ideal electrode placement).

In some embodiments, the percutaneous lead are surgically or interventionally placed into the treatment site in an orientation parallel, or substantially parallel, to the long axis of the peripheral nerve.

In some embodiments, the placement of the one or more electrodes places a long axis of the percutaneous lead in parallel, or substantially in parallel, to the long axis of the peripheral nerve.

In some embodiments, the one or more electrodes are placed in parallel, or substantially in parallel to, the overlapping nerve region over a distance selected from the group consisting of greater than about 4 millimeters (mm), greater than about 5 mm, greater than about 6 mm, greater than about 7 mm, greater than about 8 mm, greater than about 9 mm, greater than about 1 centimeter (cm), greater than about 2 cm, greater than about 2.5 cm, greater than about 3 cm, greater than about 3.5 cm, greater than about 4 cm, greater than about 4.5 cm, greater than about 5 cm, greater than about 5.5 cm, greater than about 6 cm, greater than about 6.5 cm, greater than about 7 cm, greater than about 7.5 cm, greater than about 8 cm, greater than about 8.5 cm, greater than about 9 cm, greater than about 9.5 cm, and up to about 10 cm.

In some embodiments, the electrical stimulation is predominantly a sinusoidal waveform, a square waveform, a triangular waveform, a sinc waveform, a noisy waveform, or a chirp waveform.

In some embodiments, the one or more electrodes do not directly contact a portion of the peripheral nerve at the overlapping nerve region and is in proximity to the overlapping nerve region by less than about 15 millimeters.

In some embodiments, the peripheral nerve is selected from the group consisting of an enteric nerve, an autonomic nerve, and a cranial nerve.

In some embodiments, the electrical stimulation comprises high-frequency stimulation having a fundamental frequency harmonics between about 2 KHz and about 100 KHz. In some embodiments, the high-frequency electrical stimulation is predominantly a sinusoidal waveform. In other embodiments, the high-frequency electrical stimulation is a square waveform, a triangular waveform, a sinc waveform, a noisy waveform (e.g., an unstructured waveform having a pre-defined frequency distribution), or a chirp waveform. In some embodiments, the electrical stimulation includes bi-phasic that deliver a varying and balance charge to the tissue.

In some embodiments, the electrical stimulation comprises high-frequency stimulation having a fundamental frequency harmonic between about 2 KHz and about 100 KHz. In some embodiments, the high-frequency stimulation is predominantly a sinusoidal waveform. In other embodiments, the high-frequency stimulation is a square waveform, a triangular waveform, a sinc waveform, a noisy waveform (e.g., an unstructured waveform having a pre-defined frequency distribution), or a chirp waveform (e.g., wherein any of which can having a high frequency component). In some embodiments, the electrical stimulation is predominantly charged balanced.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention to one skilled in the art, including the best mode thereof, is set forth more particularly in the remainder of the specification, including reference to the accompanying figures, in which:

FIGS. 21A, 21B, 21C, and 21D are diagram illustrating example procedures of FIG. 20 of placing a percutaneous lead at a treatment site of a subject to block nerve conduction at the treatment site via an electrical stimulation (e.g., to provide pain therapy) in which an electrode of the lead is placed in parallel, or substantially in parallel to a long axis of a target nerve over an overlapping nerve region of greater than about 3 millimeter in accordance with an illustrative embodiment.

Figure 1:
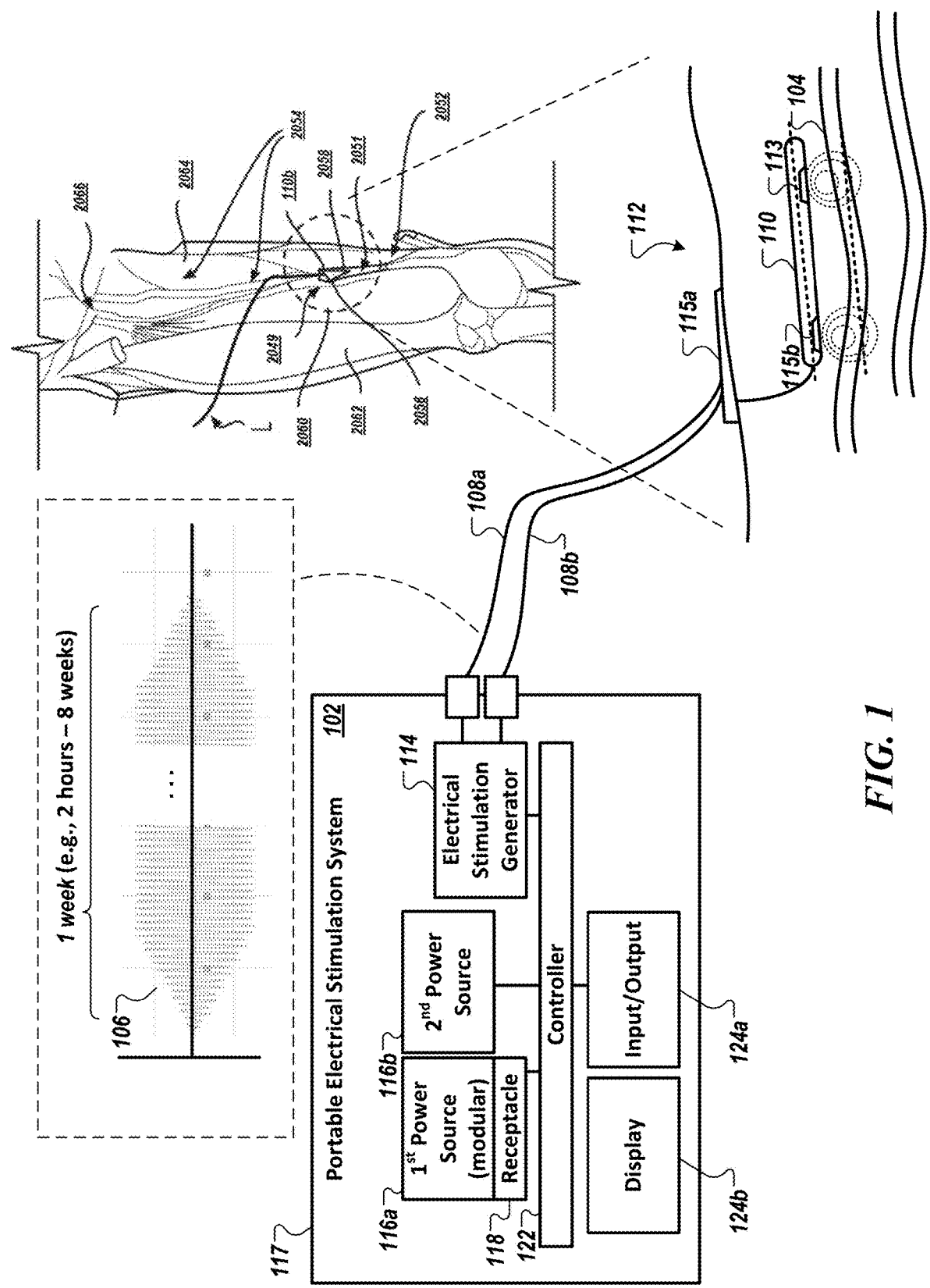
FIG. 1 is a diagram of an exemplary portable electrical stimulation system configured to deliver electrical stimulation, e.g., for percutaneously blocking painful sensations in a peripheral nerve in accordance with an illustrative embodiment.

Repeat use of reference characters in the present specification and drawings is intended to represent the same or analogous features or elements of the present invention.

Definitions

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Throughout the description and claims of this specification, the word "comprise" and variations of the word, such as "comprising" and "comprises," means "including but not limited to," and is not intended to exclude, for example, other additives, components, integers or steps. "Exemplary" and "e.g." means "an example of" and is not intended to convey an indication of a preferred or ideal aspect. "Such as" is not used in a restrictive sense, but for explanatory purposes.

As used herein, the terms "electrical stimulation" or "electrical nerve-blocking stimulation" or "electrical nerve-block" refer to electrical energy delivered by a controller to the tissues by means of one or more electrodes. The electrical energy, upon reaching an axon of a neuron, blocks the propagation of action potentials through the stimulation site, resulting in a partial or complete cessation of nerve conduction, e.g., that partially or completely inhibit painful sensations by the patient at the stimulation site. Where the electrical stimulation does so without eliciting non-targeted motor and sensory activity, the disclosure will indicate as such.

The electrical energy, in some embodiments, is characterized as a high-frequency temporally varying voltage, current, power, and/or other electrical measure, e.g., as a high-frequency alternating current unless stated otherwise. Delivery of the electrical energy to the target tissue is referred to as an electrical treatment, an electrical therapy, or simply a treatment or a therapy. The electrical energy creates an electrical field in the tissue such that control of the electrical energy strongly influences control of the electrical field in the tissue.

As used herein, the term "nervous structure" or "neural structure" refers to a structure including neural and non-neural tissue. In addition to neural tissue (such as neurons and components of neurons including axons, cell bodies, dendrites and synapses of neurons), nervous structures may also include non-neural tissue such as glial cells, Schwann cells, myelin, immune cells, connective tissue, epithelial cells, neuroglial cells, astrocytes, microglial cells, ependymal cells, oligodendrocytes, satellite cells, cardiovascular cells, blood cells, etc.

As used herein, the terms "percutaneous" and/or "percutaneously" refer to electrical stimulation applied utilizing one or more electrodes penetrating through the surface of the skin so an electrode delivering electrical stimulation to a target nerve beneath the skin is also located beneath the skin.

It is contemplated that return electrodes or anodes may be located beneath the skin or on the surface of the skin unless stated otherwise herein.

As used herein, the term "percutaneous electrode" refers to electrode assemblies, e.g., in a percutaneous lead, inserted through the skin and directed into the vicinity of the nerve (mm to cm distance), without having to contact the nerve, in a minimally invasive fashion to electrically affect neural structure.

As used herein, the term "painful sensation" refers to a disagreeable sensation generated by the activation of sensory nociceptors or nerve fibers. Nociception describes the perception of acute pain and is generally caused by activation of sensory nociceptors or by disruption of nociceptor pathways (e.g. severed neurons or disrupted nociceptors). Chronic pain sensation can also be generated by activation of nerve fibers which result in a disagreeable perception similar in nature to that generated by activation of nociceptors (for example, neuropathic pain). In some cases, such as following a surgery intended to treat chronic pain, both acute pain sensation and chronic pain sensation may contribute in a mixed manner to the overall pain sensation.

As used herein, the term "target nerve" may refer to mixed nerves containing motor nerve fibers and sensory nerve fibers. It may additionally refer to sensory nerves containing only sensory nerve fibers and/or to motor nerves containing only motor nerve fibers.

As used herein, the term "peripheral nerve" refers to motor and/or sensory nerves or ganglia structure outside of the central nervous system that connect the brain and spinal cord (the central nervous system) to the entire human body.

The terms "proximal" and "distal" are used herein as relative terms that refer to regions of a nerve, positions of nerves, or regions of a stimulation device. "Proximal" means a position closer to the spinal cord, brain, or central nervous system, whereas "distal" indicates a position farther from the spinal cord, brain, or central nervous system. When referring to the position on a neural structure in the peripheral nervous system or along an appendage, proximal and distal refer to positions either closer to the central nervous system or further from the central nervous system along the pathway followed by that neural structure or appendage. When referring to the position on a neural structure in the spinal cord, proximal and distal refer to positions either closer to the brain or further from the brain along the pathway followed by the neural structure.

As used herein, the terms "preserve" or "preserving" refer to cases where nerve function is partially but not completely maintained, as well as cases where a function is completely maintained. In comparative cases, one function may be inhibited while another function is preserved, suggesting that, in a comparative sense, the inhibited function has experienced a magnitude of reduction greater than the magnitude of reduction experienced by the preserved function. Specifically, in comparative cases, inhibition of one function and preservation of another function does not require complete preservation or complete inhibition of either function or both functions.

DETAILED DESCRIPTION OF THE INVENTION

Reference will now be made in detail to one or more embodiments of the invention, examples of which are illustrated in the drawings. Each example and embodiment is provided by way of explanation of the embodiment and is not meant as a limitation of the disclosure. For example, features illustrated or described as part of one embodiment may be used with another embodiment to yield still a further embodiment. It is intended that the embodiments include these and other modifications and variations as coming within the scope and spirit of the invention.

Each and every feature described herein, and each and every combination of two or more of such features, is included within the scope of the present invention provided that the features included in such a combination are not mutually inconsistent.

Generally speaking, embodiments of present invention is directed to a system and method that can percutaneously block nerve conduction at a target nerve (e.g., a peripheral nerve such as the saphenous nerve, femoral nerve, pudendal nerve, brachial plexus nerves, radial nerve, median nerve, ulnar nerve, tibial nerve, sciatic nerve, ilioinguinal nerve, intercostal nerve, occipital nerve, suprascapular nerve, axillary nerve, lateral femoral cutaneous, lateral pectineal nerve, or the pelvic nerve), as well as the enteric nerve, the autonomic nerve, and the cranial nerve, e.g., to inhibit pain sensation, using electrical stimulation from a percutaneous lead placed in parallel, or substantially in parallel, and without direct contact, to a long axis of the peripheral nerve over an overlapping nerve region of greater than about 3 millimeters. In such configuration, the system can deliver a continuous high frequency stimulation that generates charges at the electrodes to temporarily and reversibly disrupt action potential across the length of the peripheral nerve over several nodes of Ranvier to block nerve conduction at that region. To this end, nerve transmission that originates from a downstream source are then arrested at that region of the peripheral nerve preventing pain signals associated with that source from reaching the brain and even the spinal cord. The electrical stimulation can be delivered with a ramp that does not elicit sensations corresponding to onset activity.

Indeed, the exemplary high-frequency electrical stimulation system discussed herein can be used, in some embodiments, to reversibly and temporarily inhibit nerve signal transmission through at least one of a myelinated Aδ fiber and an unmyelinated C fiber located in the peripheral nerve while preserving nerve signal transmission through at least one of the Aβ and Aα fibers, and/or motor fibers.

In some embodiments, the exemplary high-frequency electrical stimulation discussed herein is applied to peripheral nerves such as the saphenous nerve, the femoral nerve, the pudendal nerve the brachial plexus nerves, the tibial nerve, the radial nerve, median nerve, ulnar nerve, tibial nerve, the sciatic nerve, the ilioinguinal nerve, the intercostal nerve, the occipital nerve, the pelvic nerve, the suprascapular nerve, the lateral pectineal nerve, the axillary nerve, the lateral femoral cutaneous or other large peripheral nerves, e.g., at a nerve region having a diameter greater than about 2.5 mm. In some embodiments, the exemplary high-frequency electrical stimulation discussed herein is applied to ganglia such as a dorsal root ganglia, a sympathetic ganglia, a parasympathetic ganglia, a sphenopalatine ganglion, or a gasserian ganglion, e.g., at a region having a diameter greater than about 2.5 mm.

Example System

FIG. 1 is a diagram of an exemplary portable electrical stimulation system 102 configured to deliver high-frequency electrical stimulation (106), e.g., for percutaneously blocking nerve conduction in a target nerve 104, e.g., peripheral nerve, to prevent the transmission of pain sensation over such nerve without eliciting non-targeted motor and sensory activity in accordance with an illustrative embodiment. The portable electrical stimulation system 102, in some embodiments, is configured to deliver high-frequency electrical stimulation 106 (e.g., continuous high-frequency electrical stimulatoin) comprising biphasic sinusoidal waveforms that deliver, at the electrodes a balanced charge to a target nerve 104 via a set of percutaneous lead 110 comprising electrodes to reversibly and temporarily block nerve fiber activity at the stimulation delivered site of the target nerve 104. As used herein, the term "high-frequency" refers to a stimulation frequency that is generated during a therapy session, the stimulation having a fundamental frequency harmonics greater than 1.5 kHz. Percutaneous lead includes lead body and electrode assemblies configured to be inserted through the skin and part of the underlying tissue to be placed into the vicinity of the nerve (mm to cm distance) in a minimally invasive fashion to electrically affect neural physiology. The percutaneous lead 110, in some embodiments, include one or more anodic electrodes 113 and cathodic electrodes 115 (shown as 115a) to be disposed, or affixed, beneath the skin or on the surface of the skin. In other embodiments, the cathodic electrode (or return electrode) (shown as 115b) is disposed on the percutaneous lead 110. Though shown in FIG. 1 with two charge effects generated at two electrodes, it is contemplated that a single stimulation output can be applied. The percutaneous lead 110 is configured to be delivered to the target site, in some embodiments, with an introducer needle having a universal lure connector, e.g., for syringe or bolus operation.

In some embodiments, the exemplary portable electrical stimulation system 102 is configured to generate a high-frequency electrical stimulation 106 having a fundamental frequency harmonics in the range between about 1.5 kHz and about 15 kHz. In some embodiments, the exemplary portable electrical stimulation system 102 is configured to generate a high-frequency electrical stimulation 106 having a fundamental frequency harmonics in the range between about 1.5 kHz and about 25 kHz. In some embodiments, the exemplary portable electrical stimulation system 102 is configured to generate a high-frequency electrical stimulation 106 having a fundamental frequency harmonics in the range between about 1.5 kHz and about 50 kHz. In some embodiments, the exemplary portable electrical stimulation system 102 is configured to generate a high-frequency electrical stimulation 106 having a fundamental frequency harmonics in the range between about 1.5 kHz and about 75 kHz.

In some embodiments, the exemplary portable electrical stimulation system 102 is configured to generate a high-frequency electrical stimulation 106 having any frequency component (e.g., any harmonics) in the range between about 1.5 kHz and about 15 kHz. In some embodiments, the exemplary portable electrical stimulation system 102 is configured to generate a high-frequency electrical stimulation 106 having any frequency component (e.g., any harmonics) in the range between about 1.5 kHz and about 25 kHz. In some embodiments, the exemplary portable electrical stimulation system 102 is configured to generate a high-frequency electrical stimulation 106 having any frequency component (e.g., any harmonics) in the range between about 1.5 kHz and about 50 kHz. In some embodiments, the exemplary portable electrical stimulation system 102 is configured to generate a high-frequency electrical stimulation 106 having any frequency component (e.g., any harmonics) in the range between about 1.5 kHz and about 75 kHz.

Referring still to FIG. 1, the exemplary portable electrical stimulation system 102 is configured as an external high-frequency signal generator that is electrically and physically coupled, via a cable 108, (show as 108a, 108b) to a percutaneous lead 110 carrying the electrodes.

The cable(s) 108 has one or more conductors encapsulated therein and may include separate distinct cables to each carry the high-frequency electrical stimulation 106 or may include a single combined cable that comprises internal cables for the electrical stimulation and feedback signals.

The exposed electrode(s) of a given percutaneous lead may be inserted into a target site 112 to contact tissue proximal to, or in contact with, a target nerve. Electrodes refers to exposed conductors used to establish an electrical charge that can disrupt the conduction flow. In some embodiments, the exposed electrodes of the percutaneous lead are inserted into a tissue at a distance of about 0.5 millimeters to about 15 millimeters from the target nerve, e.g., a distance from about 0.75 millimeters to about 10 millimeters, a distance from about 1 millimeter to about 5 millimeters. In some embodiments, the exposed electrodes are located only at a tip of the percutaneous lead. In other embodiments, the exposed electrodes are located at multiple locations at the tip region of the percutaneous lead. In some embodiments, other embodiments, the exposed electrodes are located at multiple locations that runs along a longitudinal length defining a percutaneous lead.

As shown in FIG. 1, the exemplary portable electrical stimulation system 102 includes a high-efficiency electrical-stimulation generator 114 and one or more power sources 116 (shown as 116a and 116b) that are each housed in a carrier 117. The high-efficiency electrical-stimulation generator 114 is configured to generate the electrical waveform output defining the high-frequency electrical stimulation 106. The one or more power sources 116 provide power for the electrical stimulation and, in some embodiments, for the underlying controls and electronics of the exemplary portable electrical stimulation system 102.

In some embodiments, the electrical-stimulation generator 114 is configured to continuously generate the high-frequency electrical stimulation 106 at an output efficiency, at least, greater than 80%, e.g., greater than 90% and at a plurality of selectable output level (e.g., amplitude level, duty cycle, or frequency) that spans over a range of output levels that can block nerve conduction at targeted neural tissue at a target site 112 of a patient or subject (e.g., to inhibit a subject's perception of pain by blocking nerve conduction only at that neural tissue while preserving other sensory and motor function). Indeed, the high efficiency operation facilitates the portability of the electrical stimulation system 102 in providing continuous high-frequency electrical stimulation, e.g., having a fundamental frequency harmonic between 1.5 KHz-75 KHz, at a therapeutic level, for an intended duration (e.g., up to 24 hours) at a manageable and/or comfortable weight for a person (e.g., less than about 350 grams, i.e., less than about 0.75 pounds, for some embodiments).

The power source 116, in some embodiments, comprises a first set of one or more rechargeable or non-rechargeable batteries that is configured to be inserted into and held in place in a receptacle 118. In some embodiments, the power source (e.g., 116a, 116b) is placed in a carrier configured to be placed into, and mate with, the receptacle 118. The power source 116 may be a standard Lithium ion, such as 18650 standard Lithium ion cells. Typical 18650 cells has a size of 18 mm×65 mm and can have capacity between 2200 mAh and 2600 mAh. With the high-efficiency stimulation circuit, the exemplary portable electrical stimulation system 102, in some embodiments, can provide continuous therapeutic operation at maximum output/intensity (e.g., 20 mA) for at least 24 hours with a design margin of that operation of 2×. In other embodiments, the exemplary portable electrical stimulation system 102 can provide continuous therapeutic operation at nominal output/intensity (e.g., 15 mA) for at least 24 hours with a design margin with a design margin of at least 20 percent. Indeed, the system 102 can provide continuous therapeutic operation for longer duration when lower than maximum output is provided.

In FIG. 1, the exemplary portable electrical stimulation system 102 includes a first power source 116a that is housed in a carrier 120 configured to mate with and retained by the receptacle 118 to serve as a modular power source. The exemplary portable electrical stimulation system 102 includes a second power source 116b (e.g., a smaller power source, e.g., having 10% of the energy density as the first power source 116a) that is retained by receptacle 118. In some embodiments, the first power source 116a is used as a primary source of power for the exemplary portable electrical stimulation system 102 and is sized (in terms of energy density) to provide continuous power output (e.g., at 50% power level) for up to 8 hours. In some embodiments, the first power source 116a is sized to provide continuous power output (e.g., at 50% power level) for up to 24 hours. In some embodiments, the second power source 116b is used to provide temporary source of power for the exemplary portable electrical stimulation system 102 and is sized (in terms of energy density) to provide continuous power output (e.g., at 80% power level) for up to 3 minutes (e.g., up to 5 minutes, up to 20 minutes) e.g., to allow hot-removal and hot-insertion of the first power source 116a in a replacement operation. In some embodiments, the exemplary portable electrical stimulation system 102 is configured with a single primary power source.

Referring still to FIG. 1, the exemplary portable electrical stimulation system 102 includes a controller 122 that directs the operation of the electrical-stimulation generator 114 and provides the user interface 124 (shown as "input/output" 124a and "display" 124b). The user interface 124, in some embodiments, is configured to receive inputs from, and outputs to, the user (i.e., patient or subject) as well as to medical professionals (e.g., pharmacists, pharmacy technicians, physicians, CRNAs, and nurses). The user (i.e., patient) may provide input directing operation of the stimulation device 100 including modifications to the electrical signal to a set of selectable power levels. The user interface 124, in some embodiments, further includes a display providing indication of system on/off status, electrical stimulation on/off status, signal delivery model (e.g., power level, intensity output, etc.), system status, battery storage status (e.g., remaining battery capacity, low/high battery status, etc.), to the user regarding the electrical stimulation system 102. In some embodiments, the user interface 124 includes an indication of whether the requested intensity setting (or a user change) is within, or is outside, the operating range or at one of the range limits. In some embodiments, the user interface 124 includes an indication of an error status (e.g., associated with automatic stimulation suspension or from a detected built-in-test error). In some embodiments, the user interface 124 includes an audio output for indication of an alert or alarm condition or state. In some embodiments, the user interface 124 includes communication port to external devices, such as a tablet, mobile computing device, desktop computing device, etc., to set schedules for the electrical-stimulation generator 114, track usage of the electrical stimulation system 102 (e.g., power settings of the electrical stimulation), track outputs of the electrical-stimulation generator 114, etc. In some embodiments, the controller 122 includes a patient monitoring system that is configured to amplifies and filters physiological signals (e.g., associated with patient surface temperature, blood flow, blood-oxygen levels, heart rate, muscle activity), and outputs them to the controller 122 for patient monitoring.

In some embodiments, the user interface 124 is configured to provide visual or audio outputs to guide the user to hot swap the first power source 116a with a new set of first power source 116a (e.g., having a new set of non-rechargeable batteries or a new set of fully charged, or more charged, rechargeable batteries).

The controller 122 and/or the electrical stimulation generator 114 are configured monitor to alarm and alert conditions, e.g., out-of-range output settings, software errors, watchdog error, remaining stored energy, maximum current output of the electrical stimulation, maximum voltage output of the electrical stimulation, maximum power output of the electrical stimulation, power source voltages, device temperature, electrode impedance, among others. In some embodiments, the controller 122 and/or the electrical stimulation generator 114 is configured to enter idle or suspended mode (in which electrical stimulation is suspended) when one or more parameters associated with the alarm and alert conditions are detected.

Figure 11:
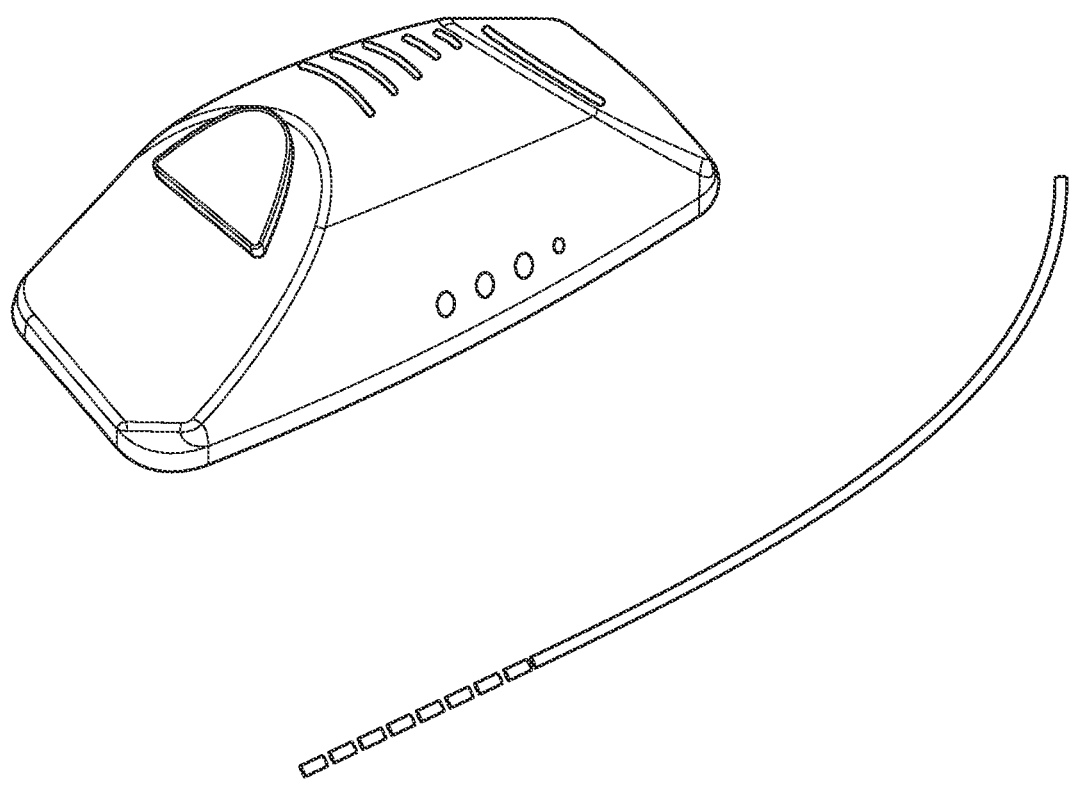
FIG. 11 shows an example of the portable electrical stimulation system of FIG. 1 in accordance with an illustrative embodiment.

The exemplary portable electrical stimulation system 202 includes the carrier 117 that houses the controller 122, user interface 124 (shown as 124a, 124b), and power source (e.g. 116a and 116b). FIG. 11 shows an example portable electrical stimulation system 102 of FIG. 1 in accordance with an illustrative embodiment.

Electrical Stimulation System #2

Figure 2:
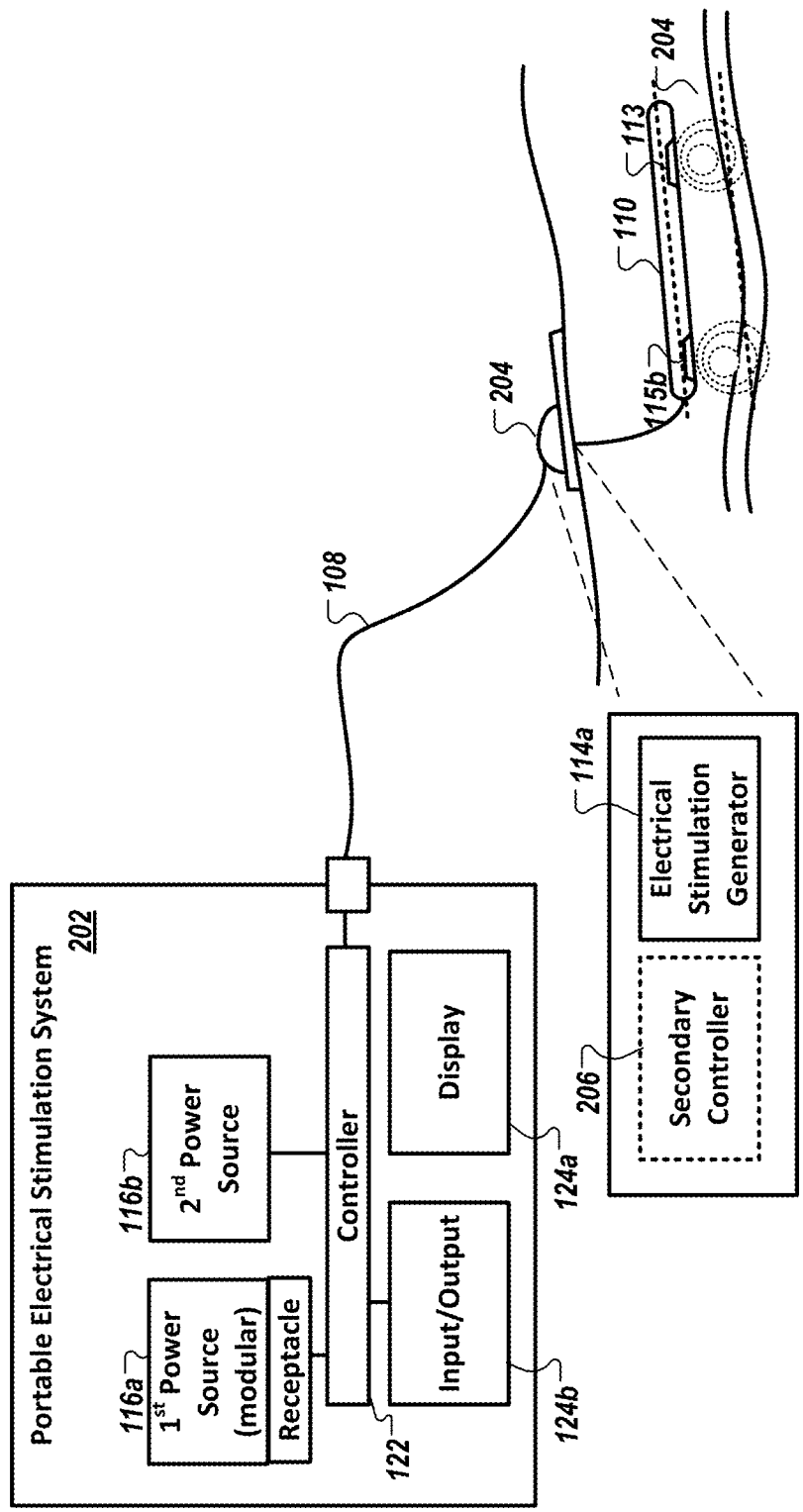
FIG. 2 is a diagram of another exemplary portable electrical stimulation system configured to deliver electrical stimulation, e.g., for percutaneously blocking painful sensations in a peripheral nerve without eliciting non-targeted motor and sensory activity in accordance with another illustrative embodiment.

FIG. 2 is a diagram of another exemplary portable electrical stimulation system 202 configured to deliver electrical stimulation (106), e.g., for percutaneously blocking painful sensations in a peripheral nerve 104 without eliciting non-targeted motor and sensory activity in accordance with another illustrative embodiment. The exemplary portable electrical stimulation system 202 includes a separate electrical-stimulation-generator portion (shown as 114a) that is housed in carrier 204 configured disposed, e.g., attached, affixed, etc., to the surface of patient, near the percutaneous lead 110, e.g., to directly couple therewith. The controller 122 of the exemplary portable electrical stimulation system 202 is configured to provide control signals to the electrical-stimulation generator 114a over the cable 108. The electrical-stimulation generator 114a, or a secondary controller 206 located in the carrier 204 or electrical-stimulation generator 114a, receives the control signals to direct the output of the electrical-stimulation generators 114a to provide the high-frequency electrical stimulation 106 to the electrodes of the percutaneous lead 110a, 110b.

High-Efficiency Electrical Stimulation Generator

Figure 3:
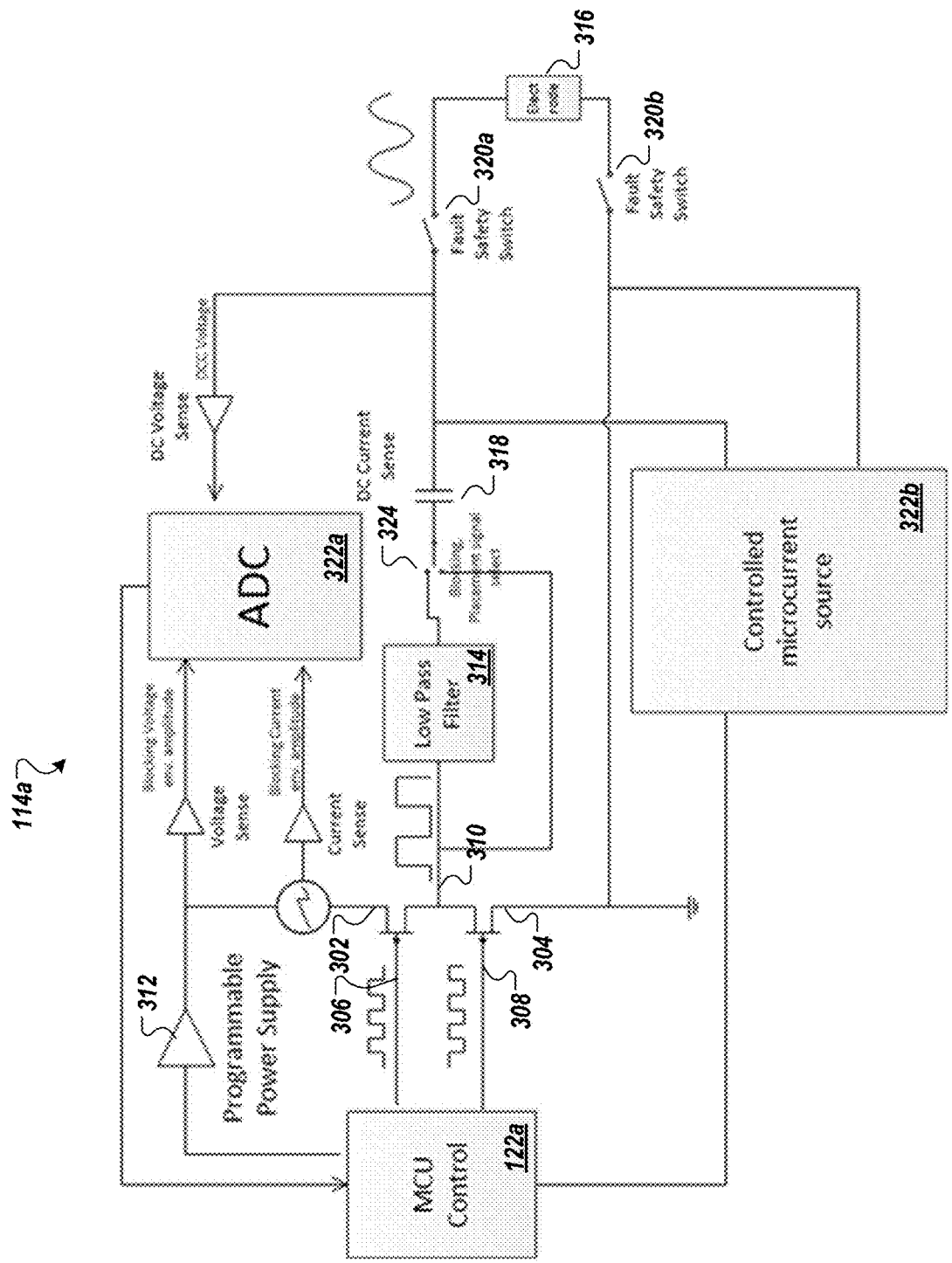
FIG. 3 is a diagram of an exemplary high-efficiency electrical-stimulation generator in accordance with an illustrative embodiment.

FIG. 3 is a diagram of an exemplary high-efficiency electrical-stimulation generator 114 (shown as 114a) in accordance with an illustrative embodiment. The electrical-stimulation generator 114a includes an electrical stimulation generating circuit comprising a set of switching circuit elements (e.g., shown as field-effect transistors 302, 304) configured in receive switching inputs 306, 308 from the controller 122 (shown as "MCU Control" 122a) to provide a switching waveform output 310 from a programmable power supply 312 to a low-pass filter 314. Indeed, the set of switching circuit elements 302, 304 allows a higher-frequency square-wave or pulsed wave output to be generated from that of the switching inputs 306, 308 (e.g., as a difference between the inputs), thereby allowing for high-efficiency operation for such embodiments. The low-pass filter 314 provides an electrical stimulation output to the electrode 113 (shown as 316) of the percutaneous lead 110 through a high-impedance output (shown as capacitor 318) and set of fault disconnect switches (shown as "Fault Safety Switch" 320a, 320b).

In some embodiments, the electrical-stimulation generator 114a includes a high impedance differential voltage sensing circuit for the detection of differential DC voltage (e.g., in 322a). In some embodiments, the electrical-stimulation generator 114 includes a variable DC current injection circuit that can counteract the buildup of DC voltages across the electrode (e.g., in 322b). In some embodiments, the electrical-stimulation generator 114a includes a feedback control system that drives the DC current injection amplitude with an amplitude and polarity that counteracts the DC contamination buildup. In some embodiments, the electrical-stimulation generator 114a includes a fault mitigation switching circuit that disengages the active circuits from the electrode in case of a circuit fault. In some embodiments, the electrical-stimulation generator 114a includes a fault mitigation switching circuit that disengages the power supplies from the active circuits that can supply current to the electrodes in case of a circuit fault. In some embodiments, the electrical-stimulation generator 114a includes a DC current sensing circuit that is used to sense circuit faults used in conjunction with fault mitigation switching circuit. In some embodiments, the electrical-stimulation generator 114a uses a high impedance differential voltage sensing circuit for the detection differential DC voltage as a fault sensing input to the fault mitigation switching circuit. In some embodiments, the electrical-stimulation generator 114a uses the same high impedance differential voltage sensing circuit for the purposes of detection of the differential DC voltage and for the detection differential DC voltage as a fault sensing input to the fault mitigation switching circuit.

In some embodiments, the electrical-stimulation generator 114a includes an impedance measurement circuit configured to detect short circuit between the electrode pair. The impedance measurement circuit, in some embodiments, is configured to measure an estimated impedance for the tissue and electrode load to normalize the electrical stimulation. In some embodiments, the impedance measurement is used as a pre-condition to initiate output of electrical stimulation to ensure that the electrical-stimulation generator 114 is properly connected to the electrode and that the electrode is properly delivered to the target site.

In FIG. 3, the electrical-stimulation generator 114a includes the feedback circuits (shown as analog-to-digital converter "ADC" 322a) configured to sense the voltage output of the electrical-stimulation generator 114a, the current output of the electrical-stimulation generator 114a, the voltage output of the programmable power supply 312, and the current output of the programmable power supply 312 and to provide sense feedbacks to the controller (122a). The measured sinusoidal current and current envelopes from a controlled voltage envelope are used, in some embodiments, to control the variable voltage switching supply to facilitate high power efficiency operation over conventional techniques.

FIG. 3 further shows a connection element (e.g., a switch 324) coupled the output of the low-pass filter 314. The connection element (e.g., 324) provides for a bypass filter circuit to the which the switching waveform output 310 can be directly applied to the electrodes, 316, for example, for detecting nerve location and ideal electrode placement.

Figure 4:
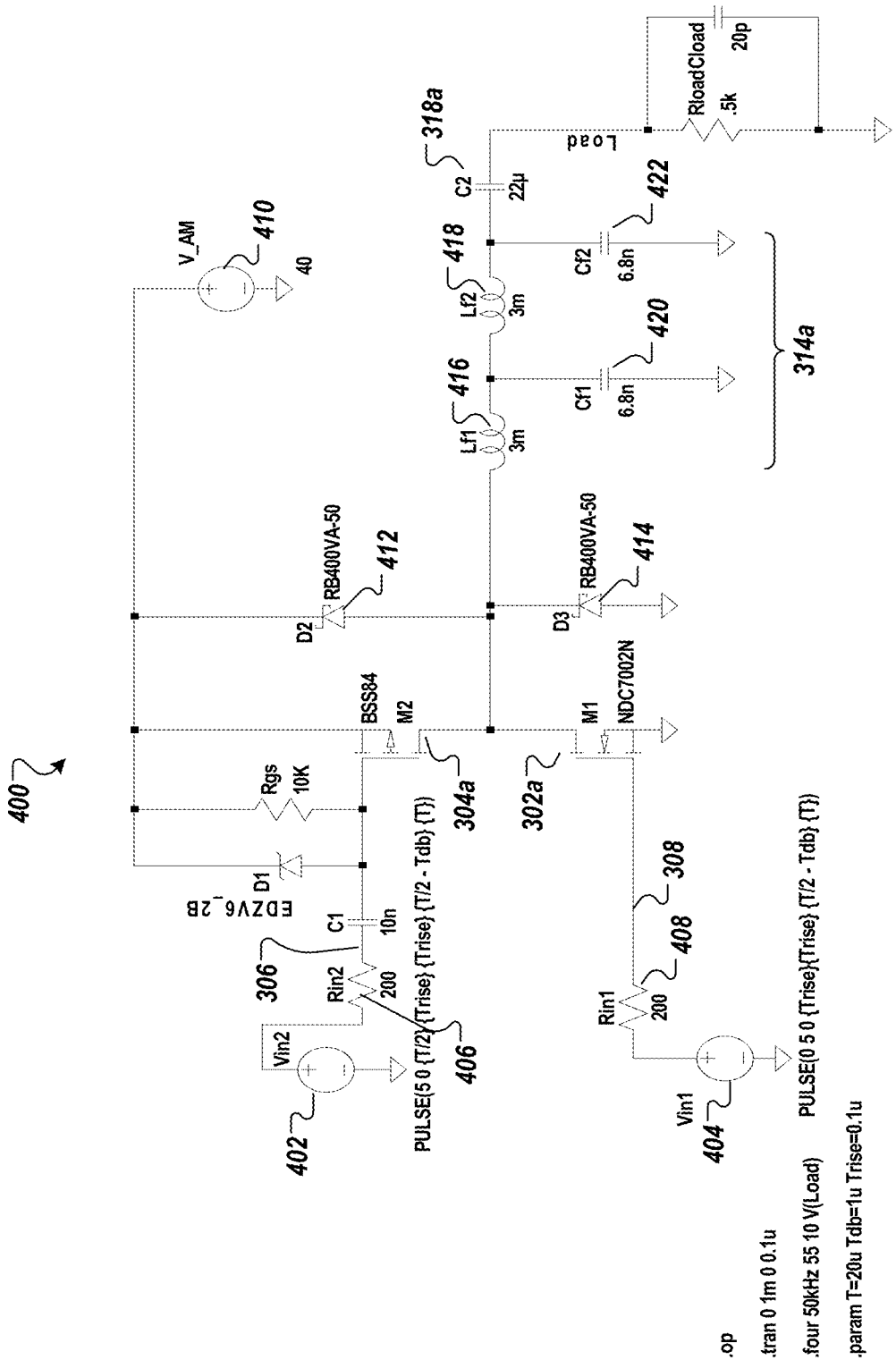
FIG. 4 is a circuit diagram of the exemplary stimulation generating circuit of the electrical-stimulation generator (e.g., in a simulation model) in accordance with an illustrative embodiment.

FIG. 4 is a circuit diagram of the exemplary stimulation generating circuit of the electrical-stimulation generator 114a (shown as 400) (e.g., in a simulation model) in accordance with an illustrative embodiment. The set of switching circuit elements, e.g., shown as field-effect transistor 302, 304, comprises an n-type MOSFET (shown as 302a) and a p-type MOSFET (shown as 304a) in which the drain of the p-type MOSFET (304a) is connected to the source of the n-type MOSFET (302a). The gates of the MOSFET (302a, 304a) are connected to output pins (e.g., 306, 308) of the MCU Control 122a (shown as voltage sources 402, 404) connected in serial to a resistive load 406, 408. The source of the p-type MOSFET (304a) is connected to the output of the programmable power supply (shown as voltage source 410) and voltage regulating diodes (shown as Zener diodes 412, 414). The drain of the n-type MOSFET (302a) is connected to circuit ground.

In FIG. 4, the low-pass filter 314 is configured as a LC low-pass filter (shown as 314a) comprising a set of inductive elements 416, 418 and capacitive elements 420, 422. Of course, fewer numbers of such elements may be used. The LC low-pass filter 314a is configured, in some embodiments, with component values suitable for high-frequency operation, e.g., between 1.5 kHz and 75 kHz. As shown, the LC low-pass filter has a cut-off frequency around about 70 kHz. Other cut-off frequencies can be used. The high-impedance output is formed using a capacitor 318a. The electrodes of the percutaneous lead 110 and target nerve are modeled as a combined resistive and capacitive load (e.g., 500 ohm and 20 pF). The electrodes of the percutaneous lead 110 and target nerve can be modeled as a combined load up to 1500 ohm, in some embodiments.

In some embodiments, the electrical-stimulation generator (e.g., 114, 114a, 400) is configured to not output a DC current exceeding 1 µA for a duration exceeding 2 seconds.

Indeed, the exemplary stimulation generating circuit (e.g., 114, 114a, 400) provides a power-efficient electrode driver circuit for sinusoidal and/or large duty cycle waveforms that includes an efficient variable voltage switching supply to provide high power efficiency and low power consumption. The exemplary stimulation generating circuit (e.g., 114a, 400, etc.) has a relatively small number of electronic components (providing an optimized implementation) that maintains performance over a wide range of power supply variations and amplitude modulation control (e.g., via power supply settings). The user of a linear regulator, in some embodiments, along with the variable voltage switching supply can be used, e.g., to extend the dynamic range of the output signal amplitude. The low pass filter stage following the switched output for generation of sinusoidal waveforms facilitates performance over a wide range of load impedances.

Example Electrical Stimulation System Circuit Design

FIGS. 5A, 5B, 5C, 5D, 5E, 5F, and 5G show circuit diagrams for an example portable electrical stimulation system (500) of FIG. 1 or 2 configured to deliver electrical stimulation in accordance with an illustrative embodiment.

The electrical stimulation system 500 provides a power-efficient electrode driver circuit for sinusoidal and/or large duty cycle waveforms. The power-efficient electrode driver circuit includes an efficient switching output circuit with variable voltage switching supply and is used to generate square or rectangular waveforms. The power-efficient electrode driver circuit includes a low-pass filter stage following the switching output circuit configured to generate sinusoidal waveforms that can maintain performance over a wide range of load impedances. Indeed, the electrical stimulation system 500 is configured for high power efficiency and low power consumption. The electrical stimulation system 500 also has low complexity with fewer numbers of electronic components. The electrical stimulation system 500 includes a linear regulator along with a variable voltage switching supply to extend the dynamic range of the output signal amplitude that can maintain performance over a wide range of power supply variations, allowing for amplitude control and modulation, e.g., via power supply settings.

Figure 5A:
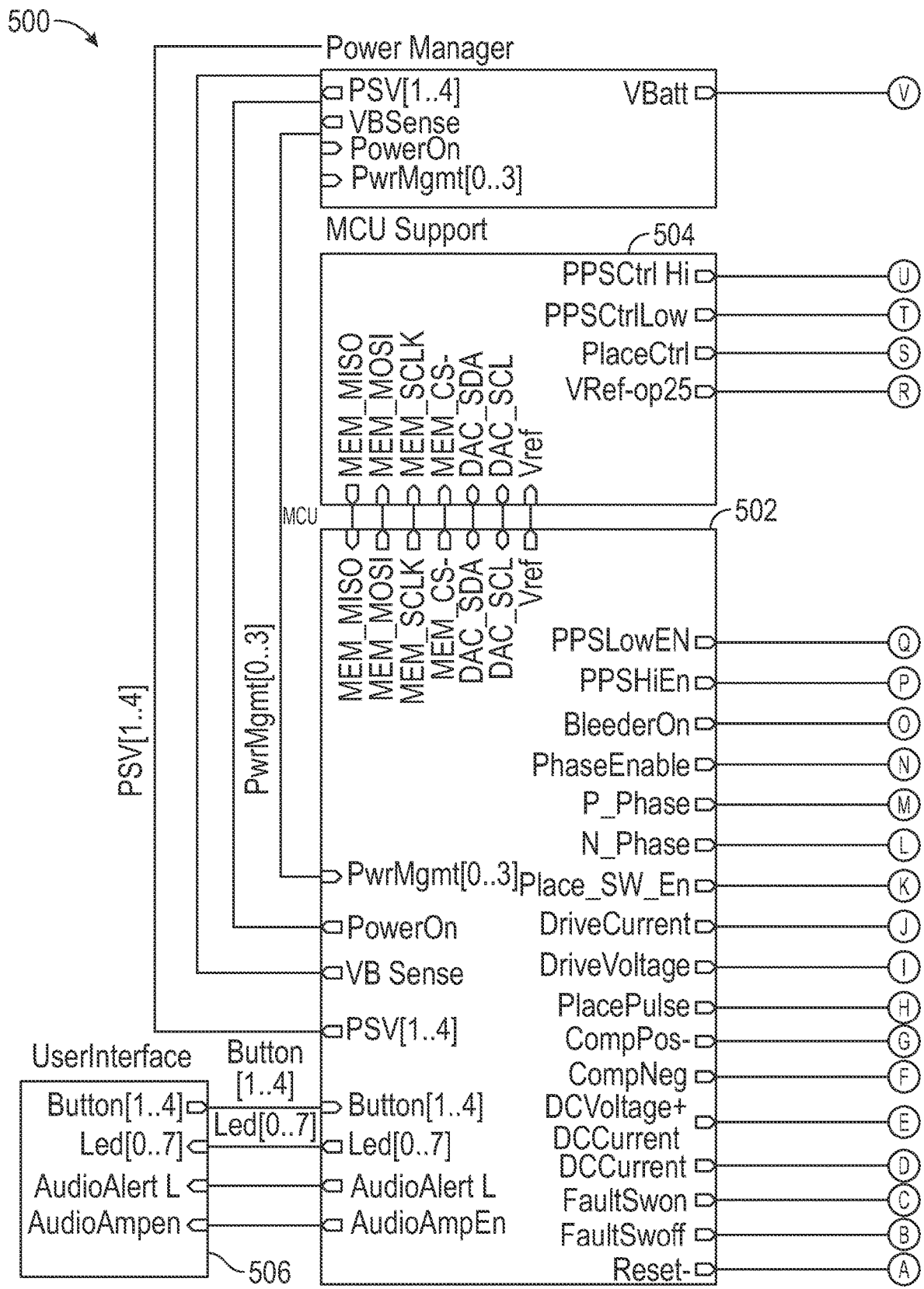
FIGS. 5A, 5B, 5C, 5D, 5E, 5F, and 5G show circuit diagrams for an example portable electrical stimulation system of FIG. 1 or 2 configured to deliver electrical stimulation in accordance with an illustrative embodiment.
Figure 5A:
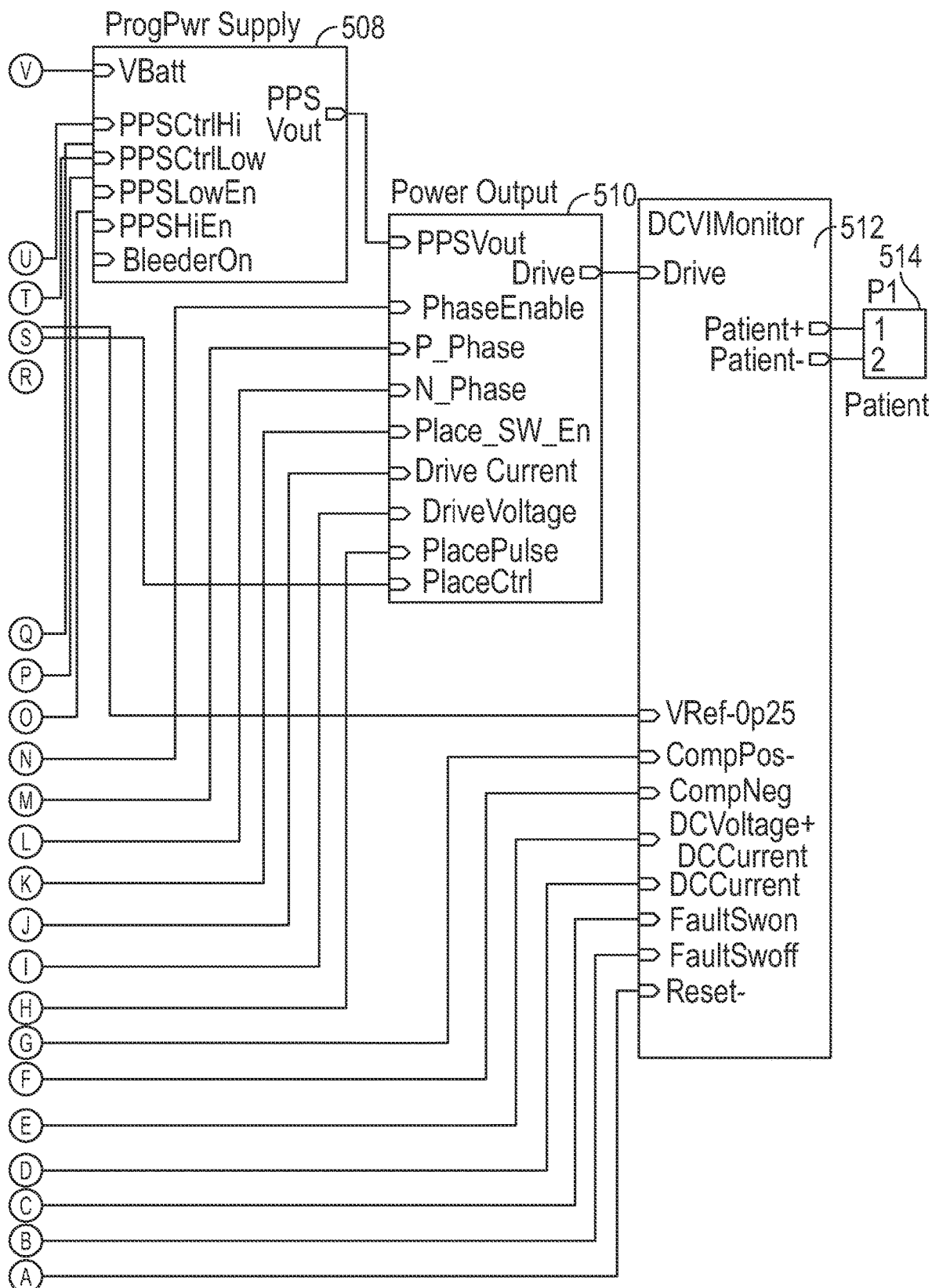
Figure 5B:
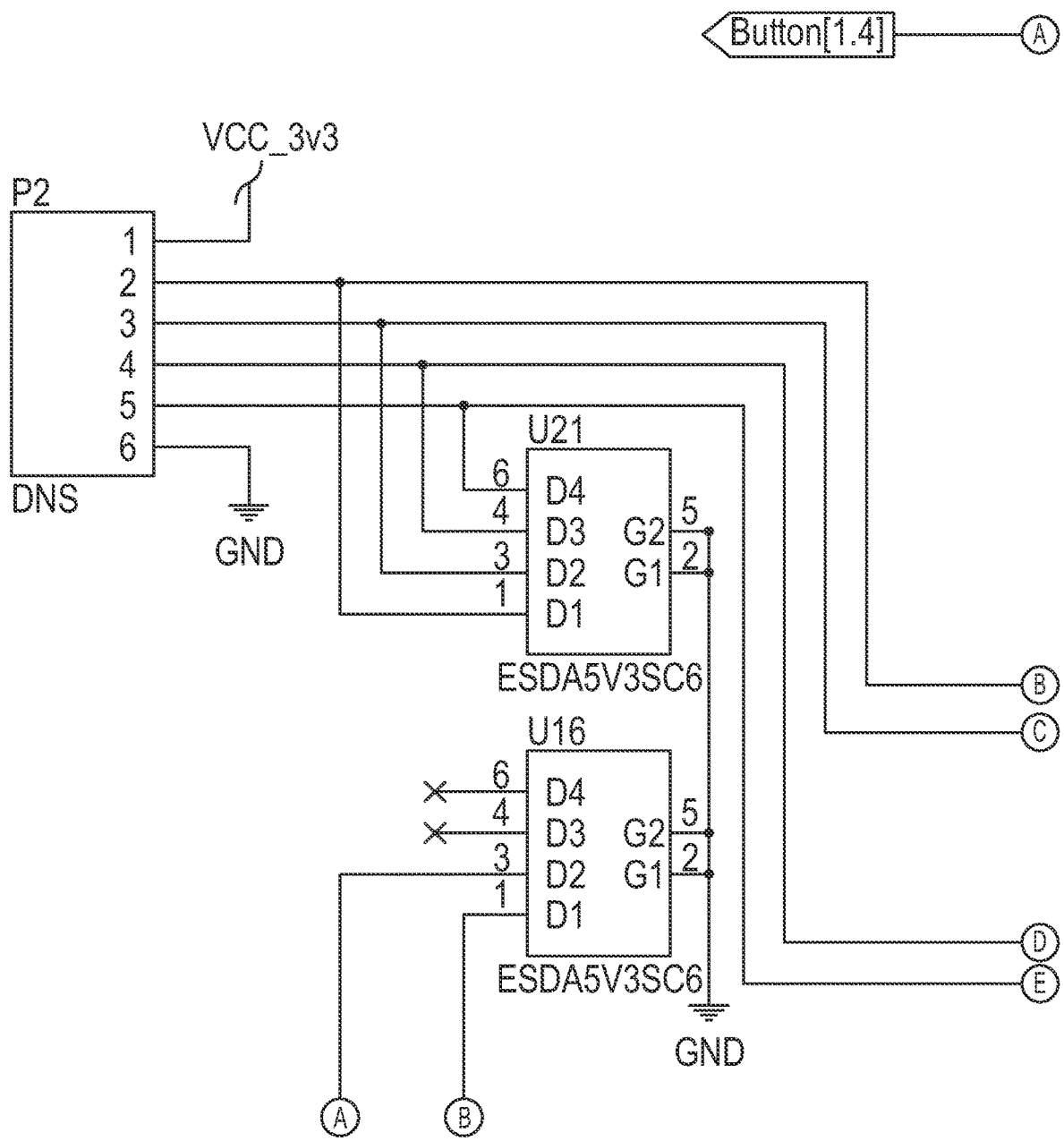
Figure 5B:
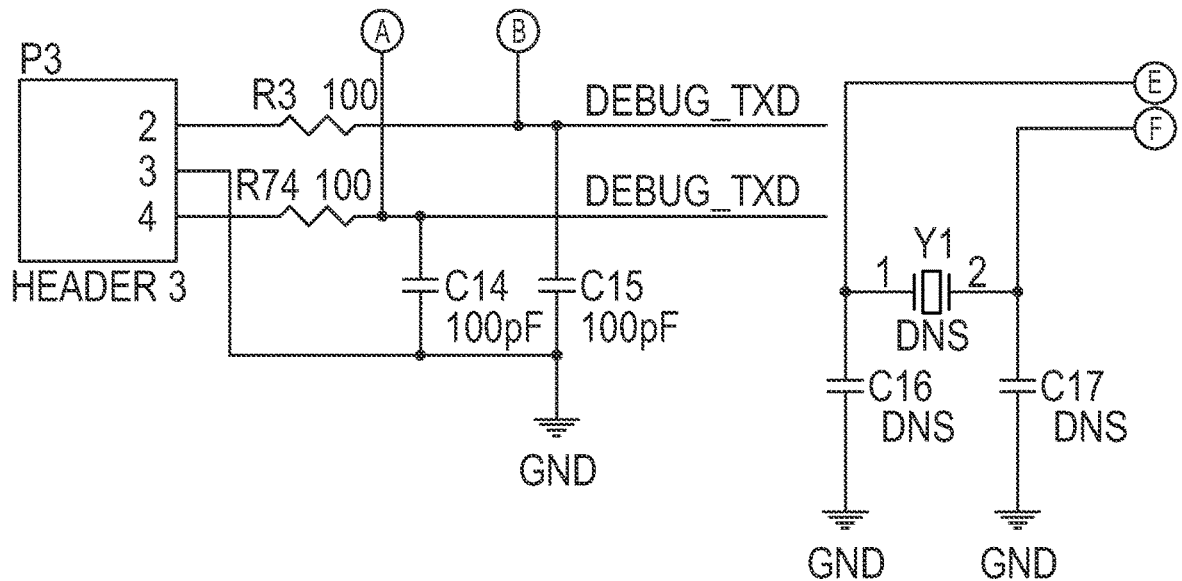
Figure 5B:
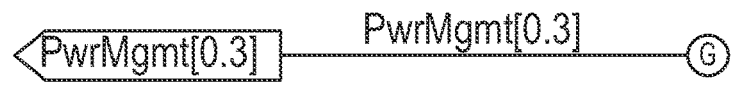
Figure 5B:
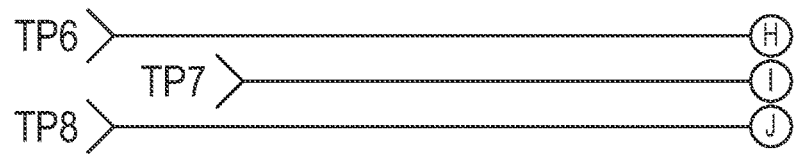
Figure 5B:
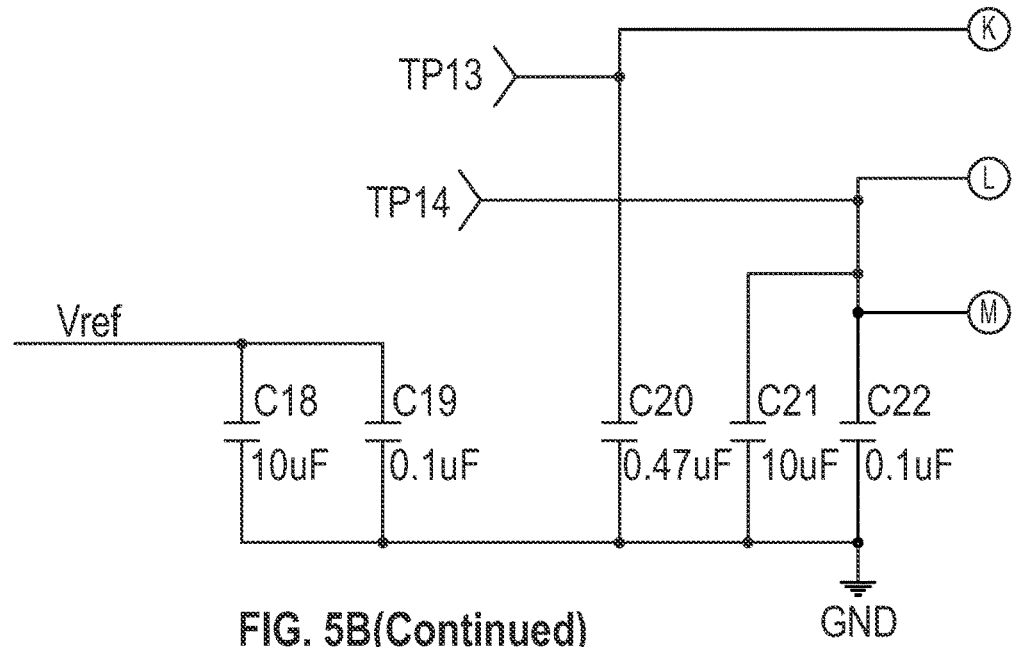
Figure 5B:
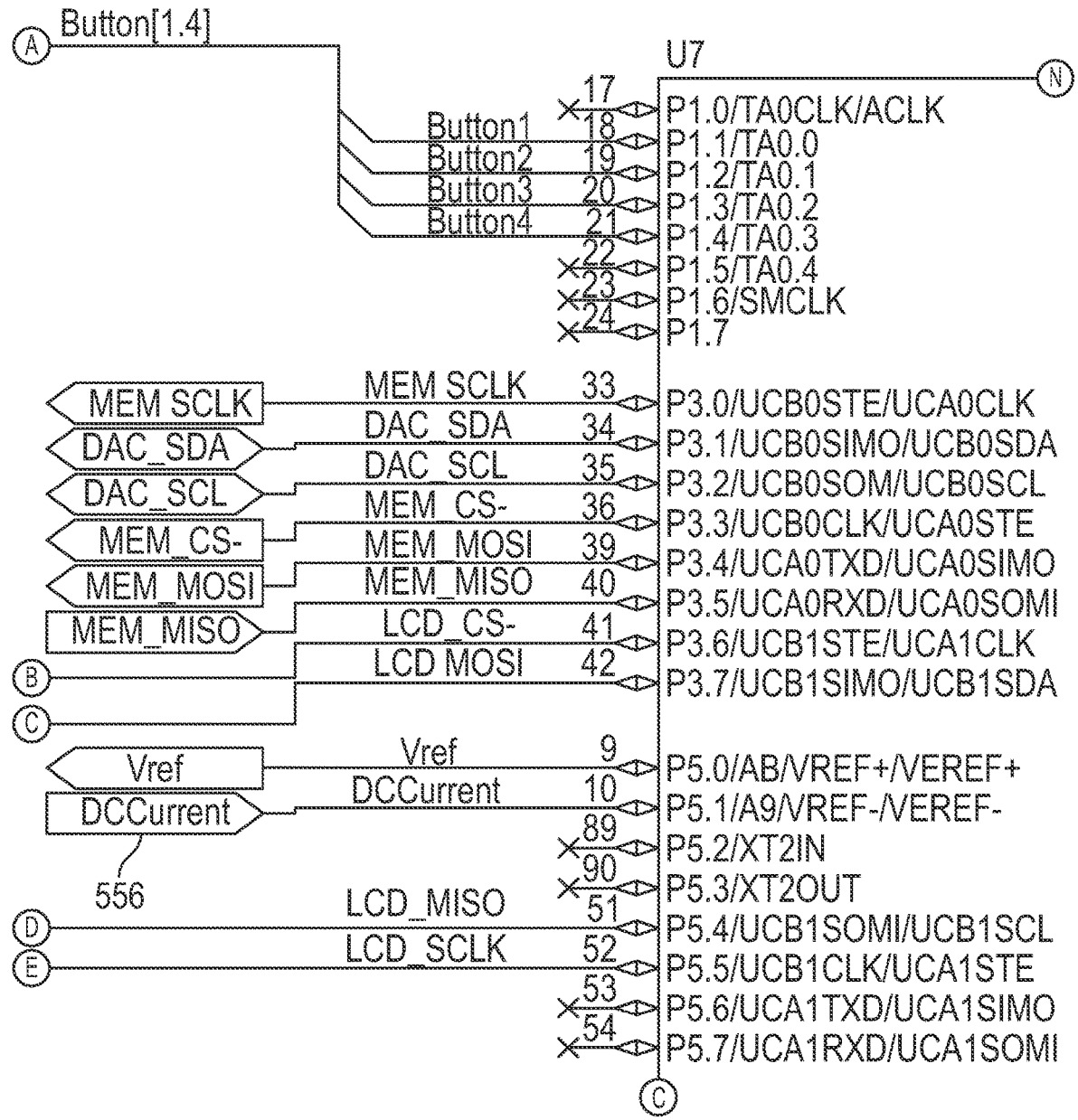
Figure 5B:
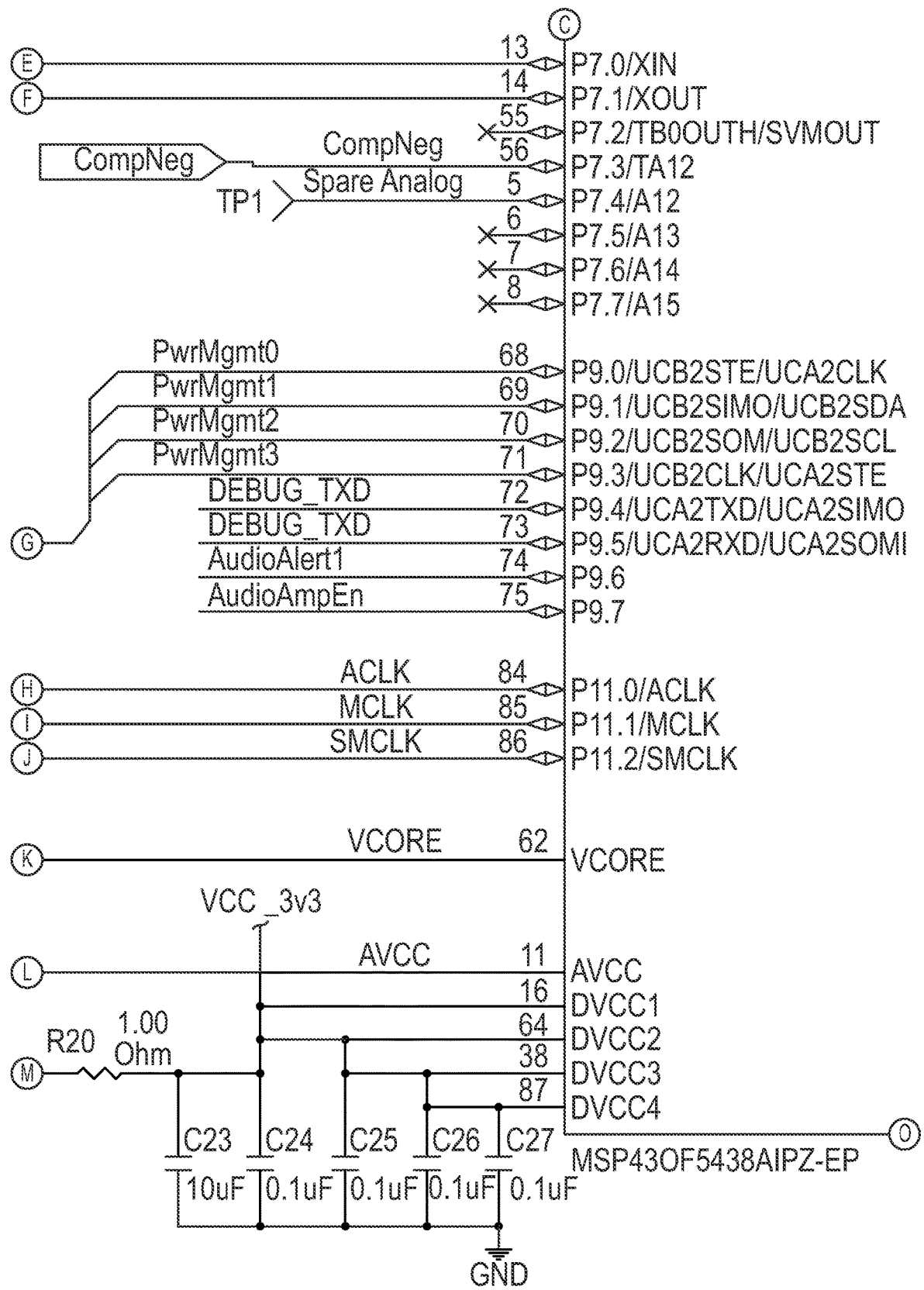
Figure 5B:
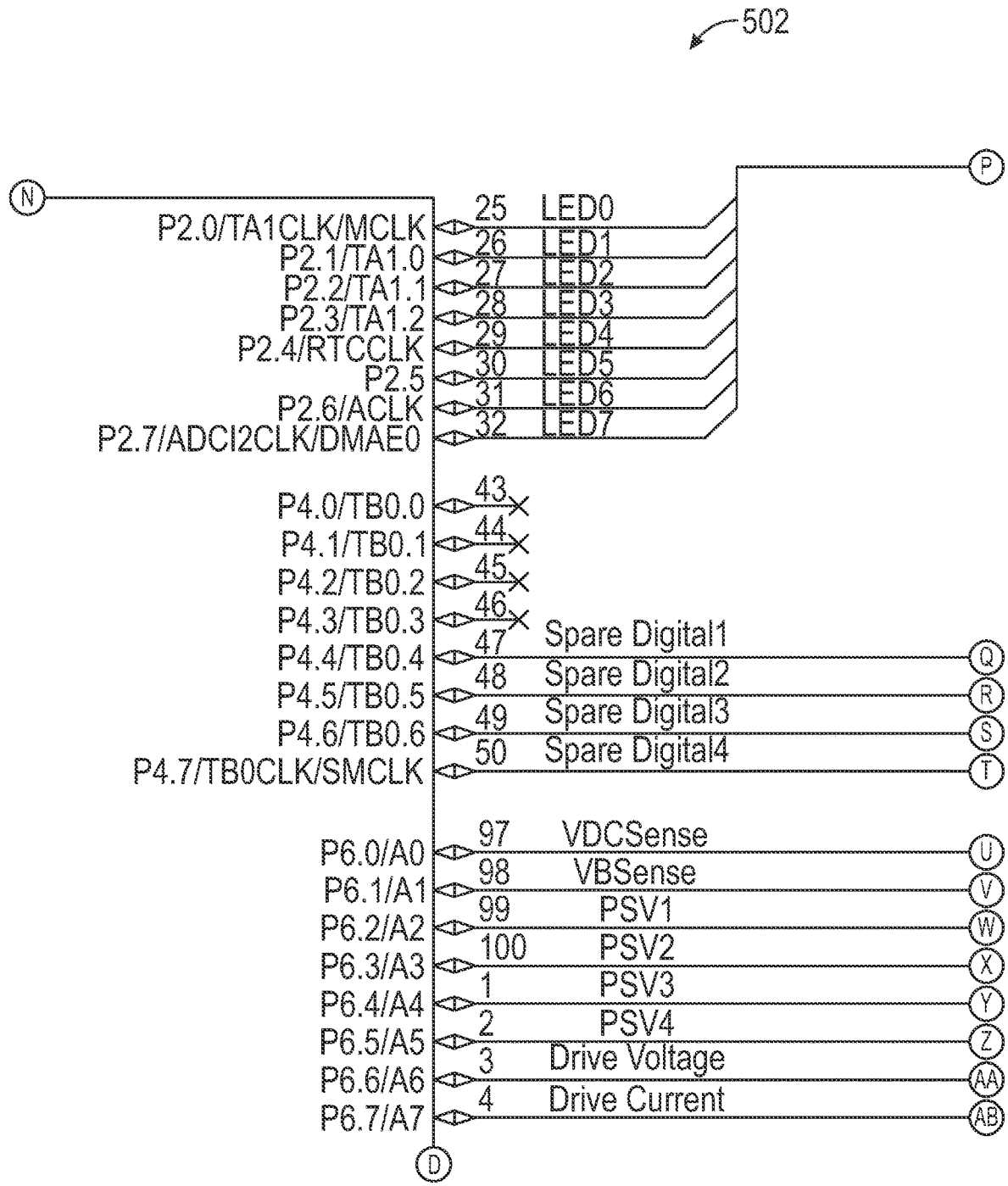
Figure 5B:
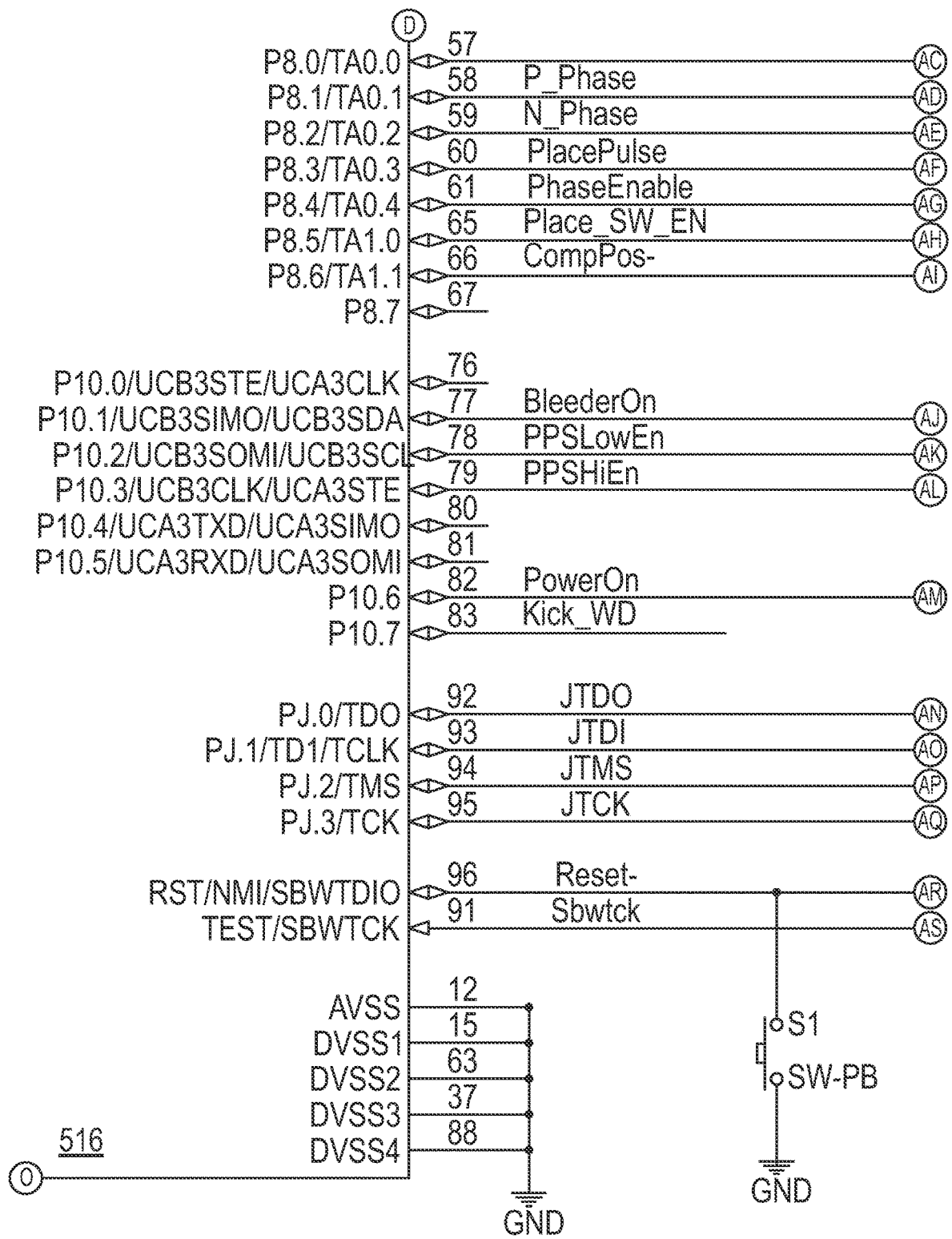
Figure 5B:
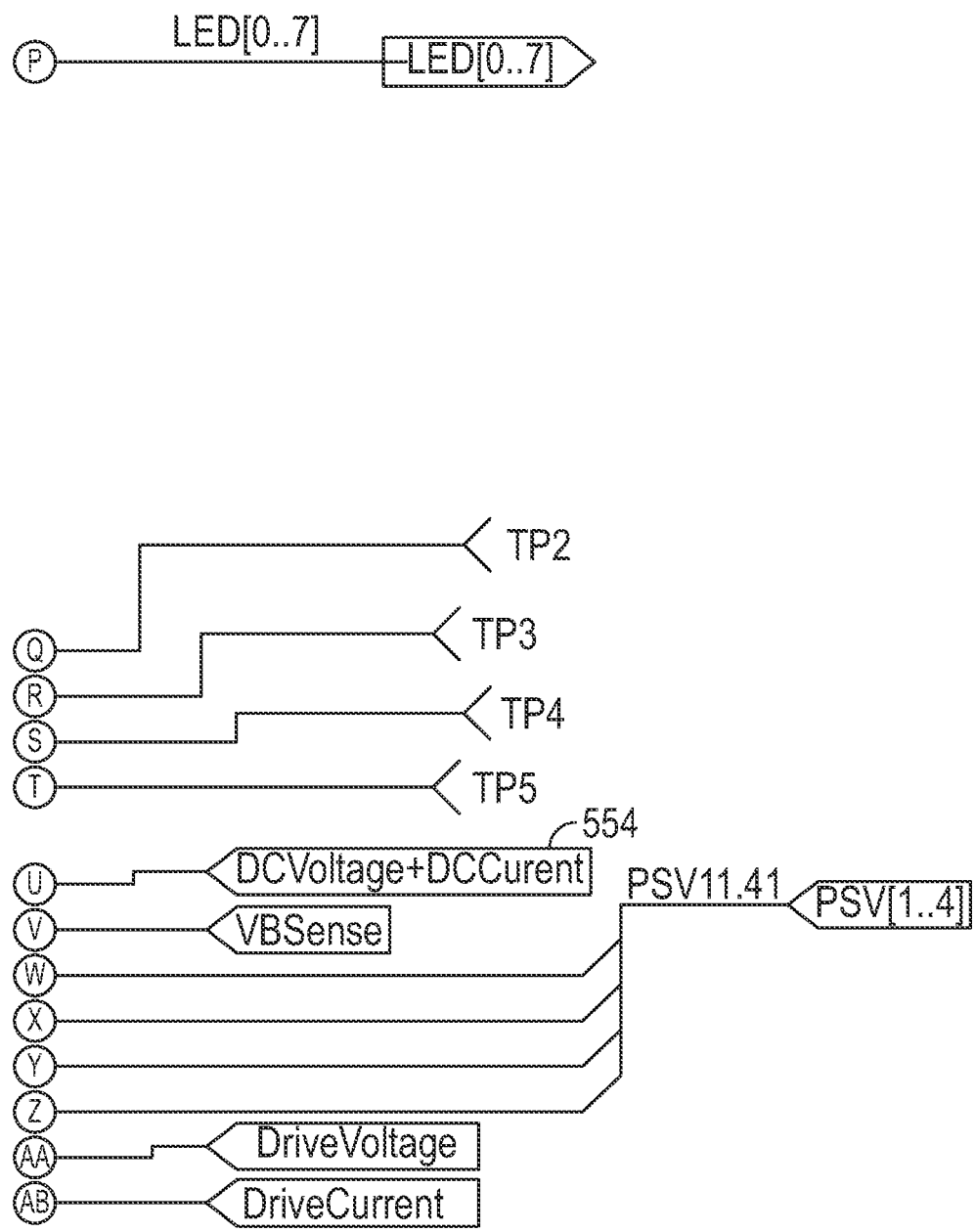
Figure 5B:
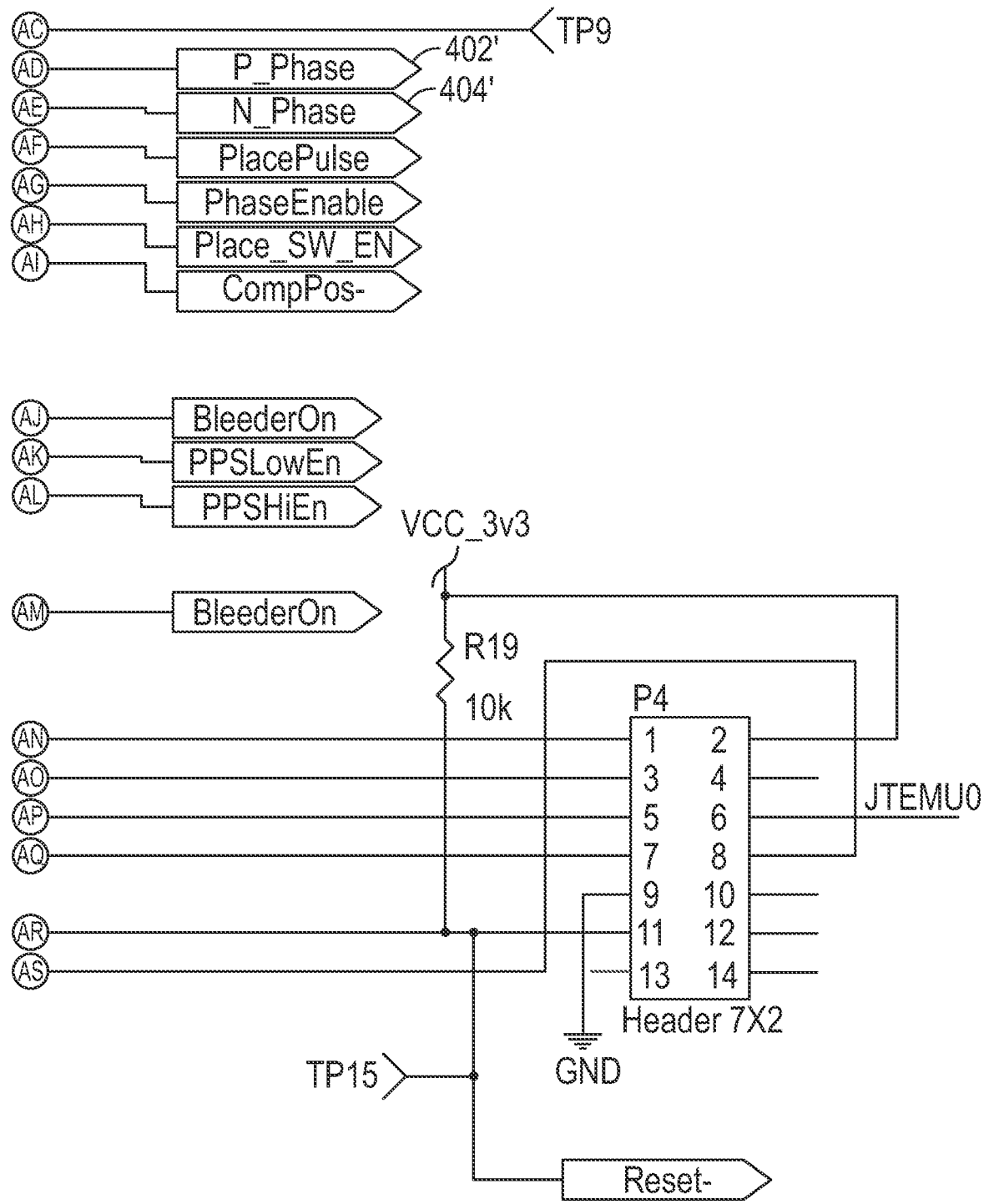
Figure 5B:
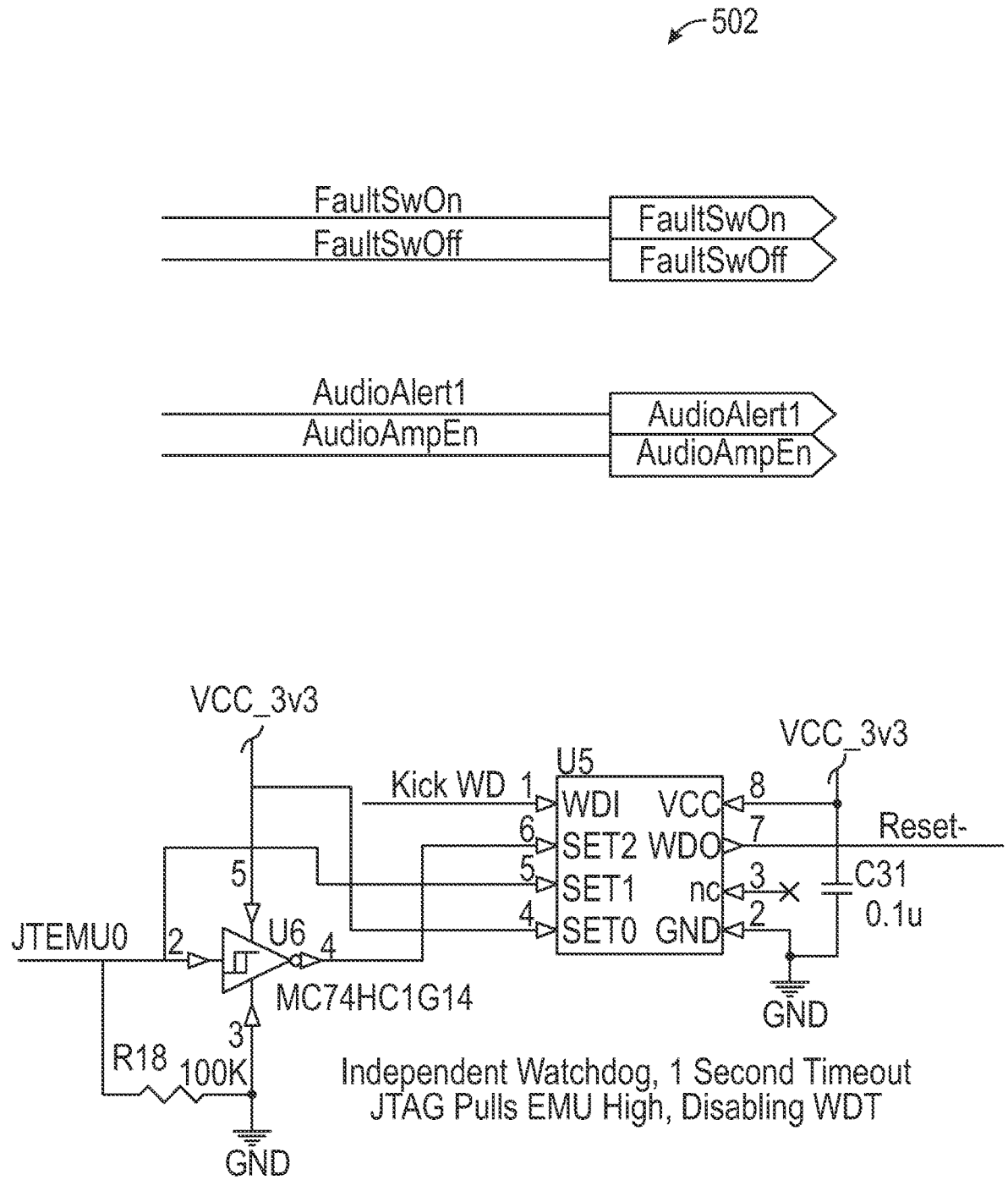
Figure 5C:
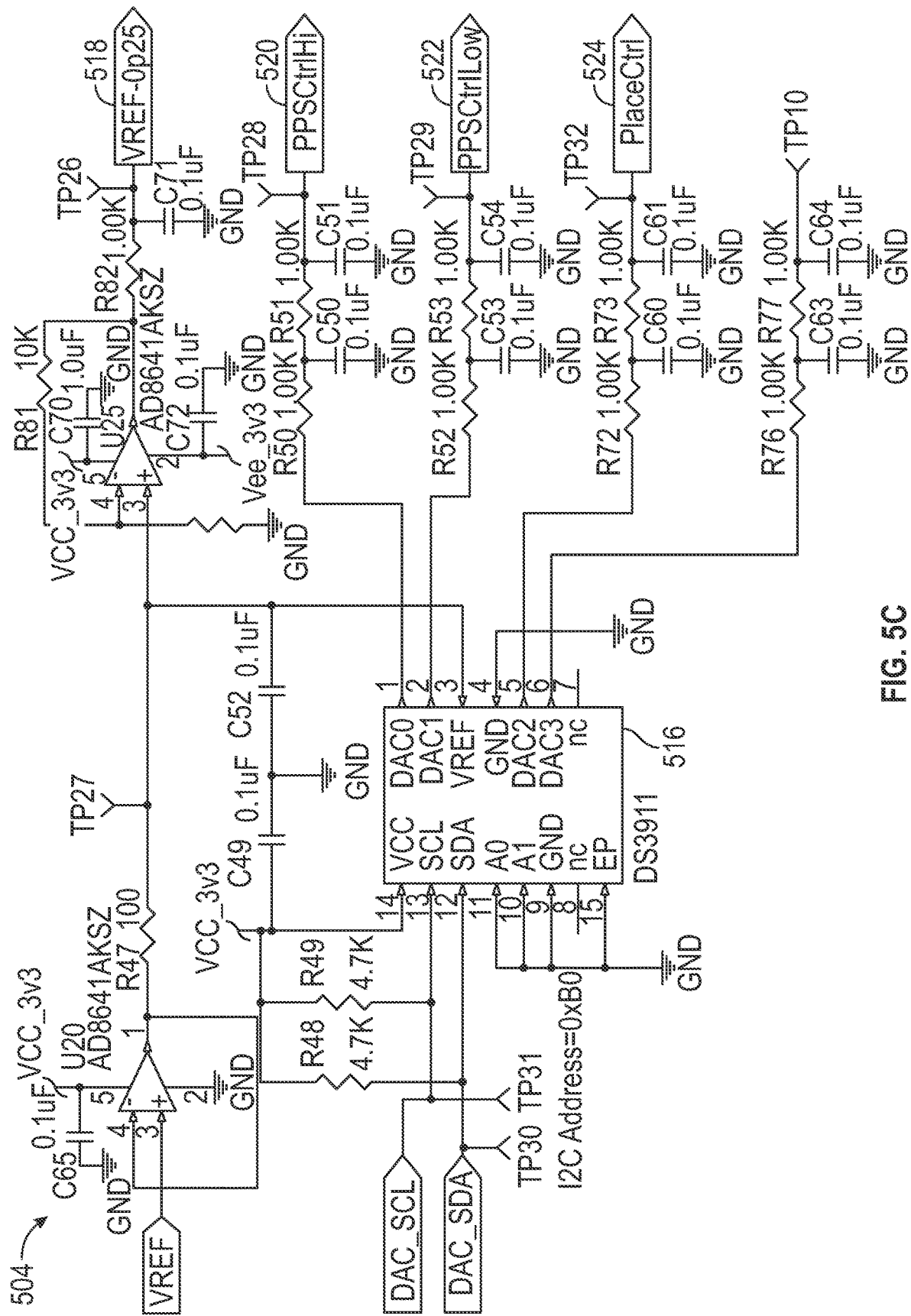
Figure 5C:
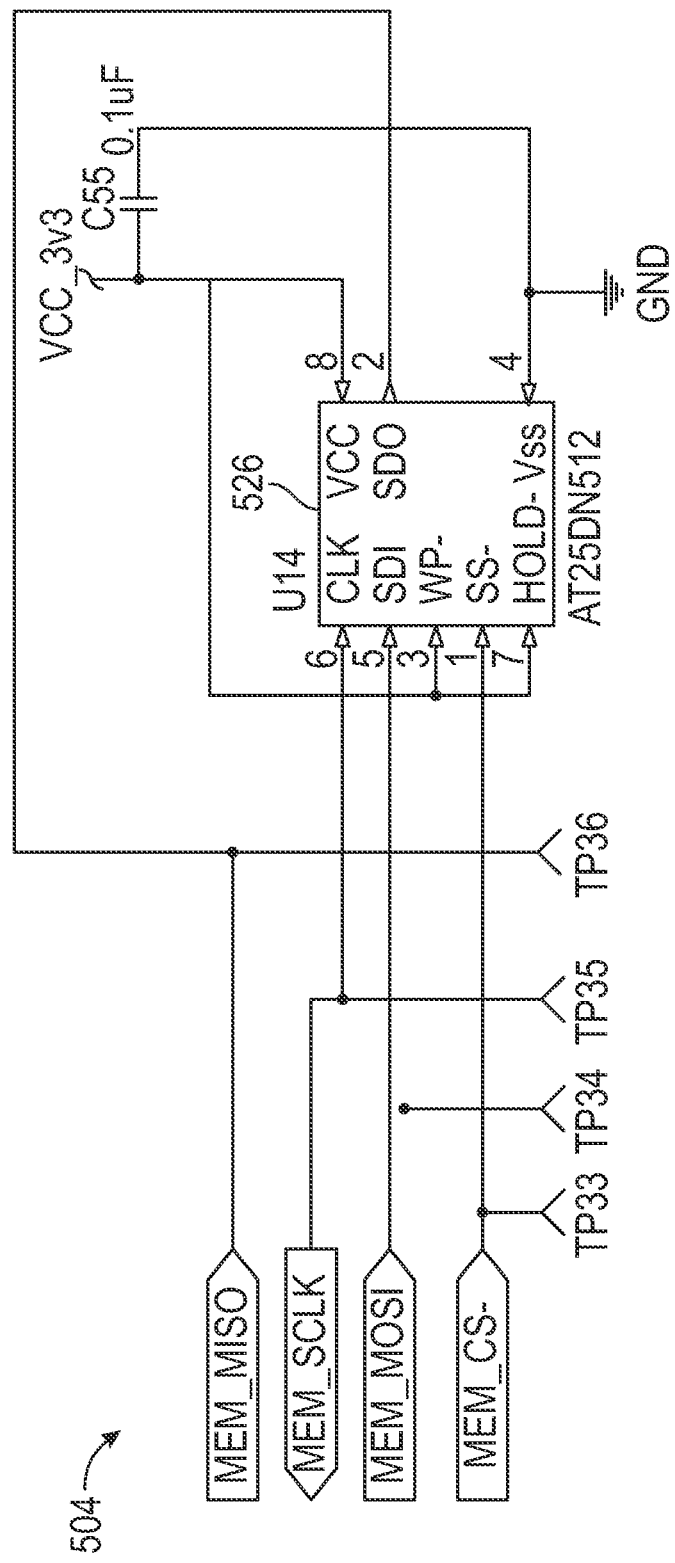
Figure 5D:
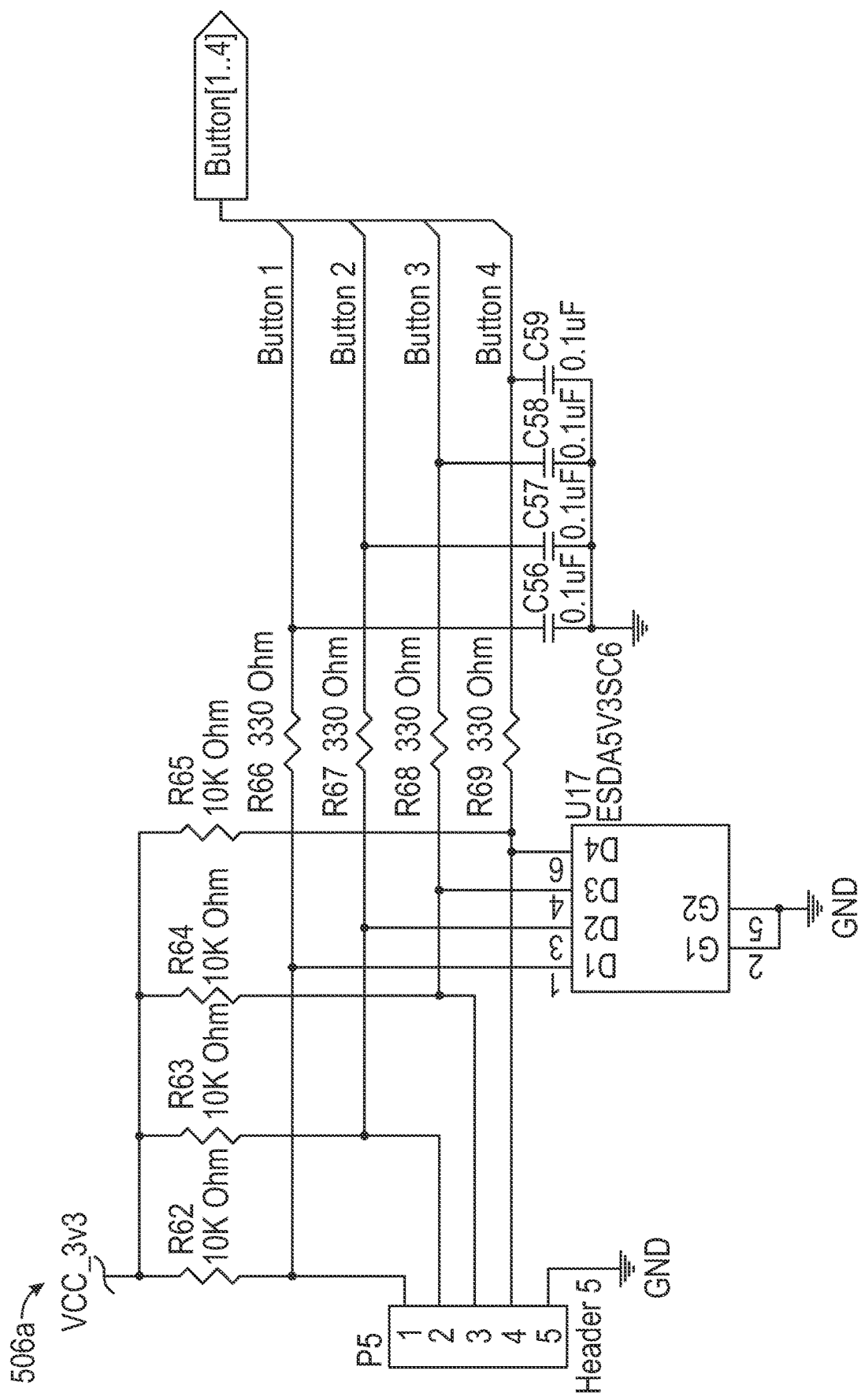
Figure 5D:
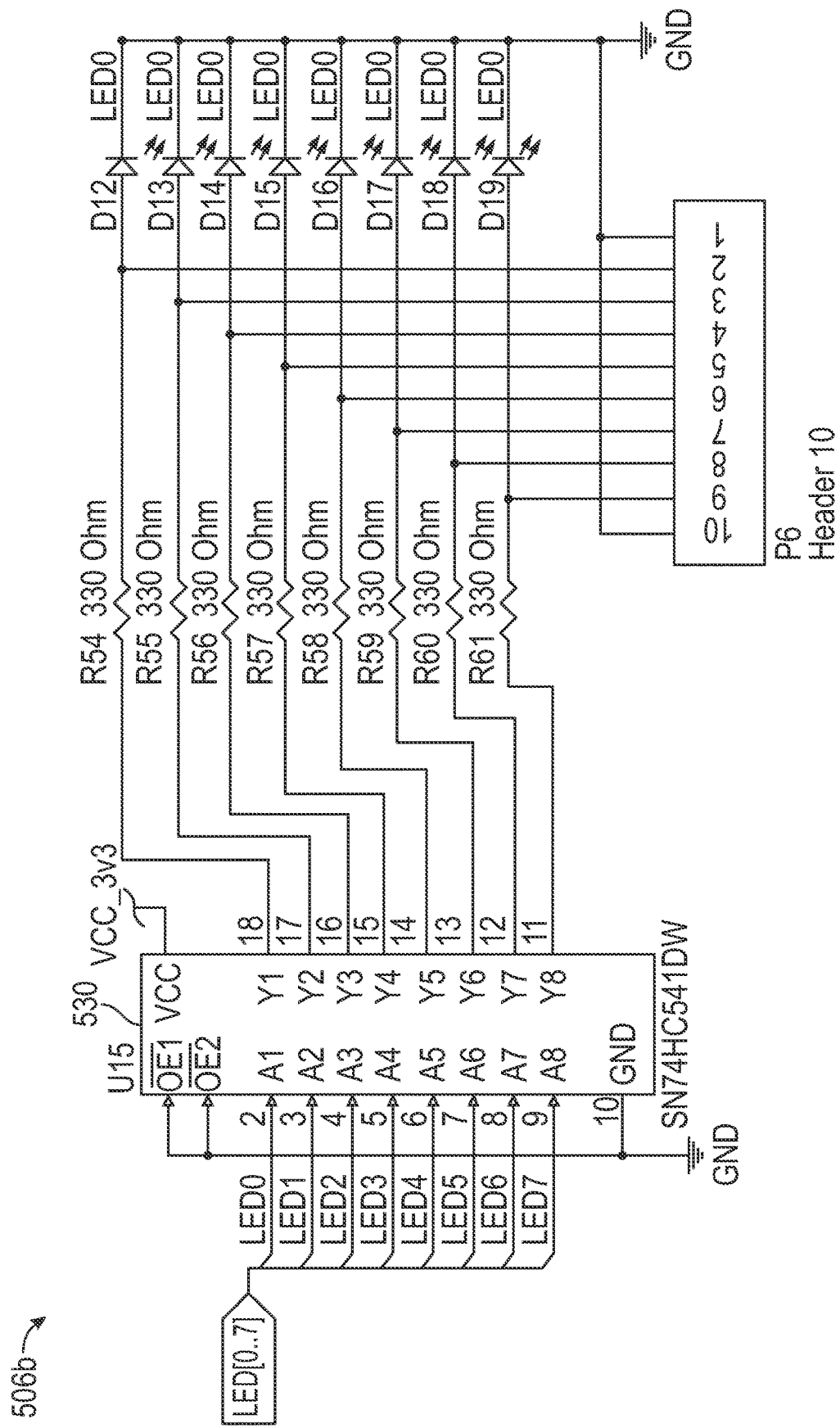
Figure 5D:
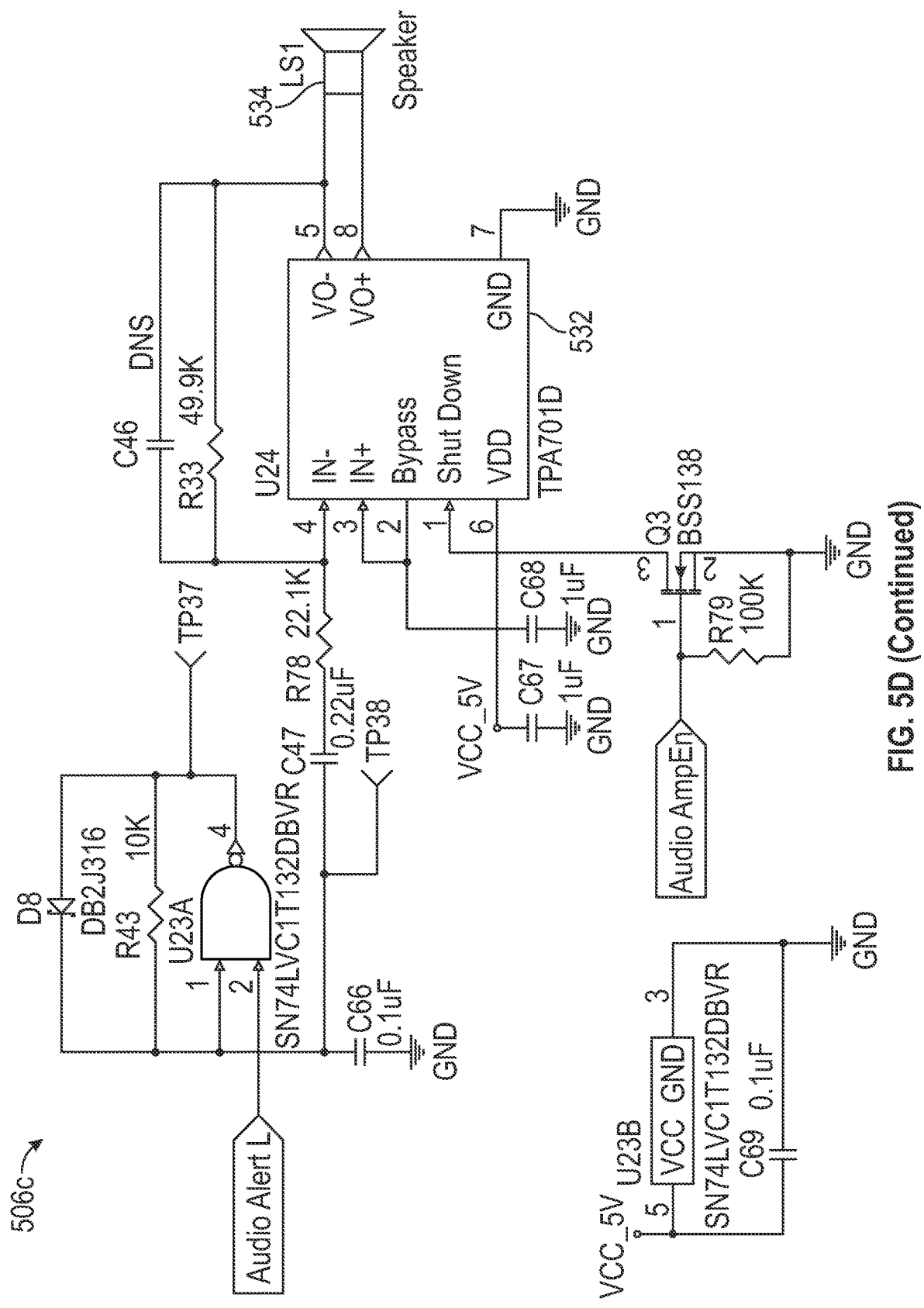
Figure 5E:
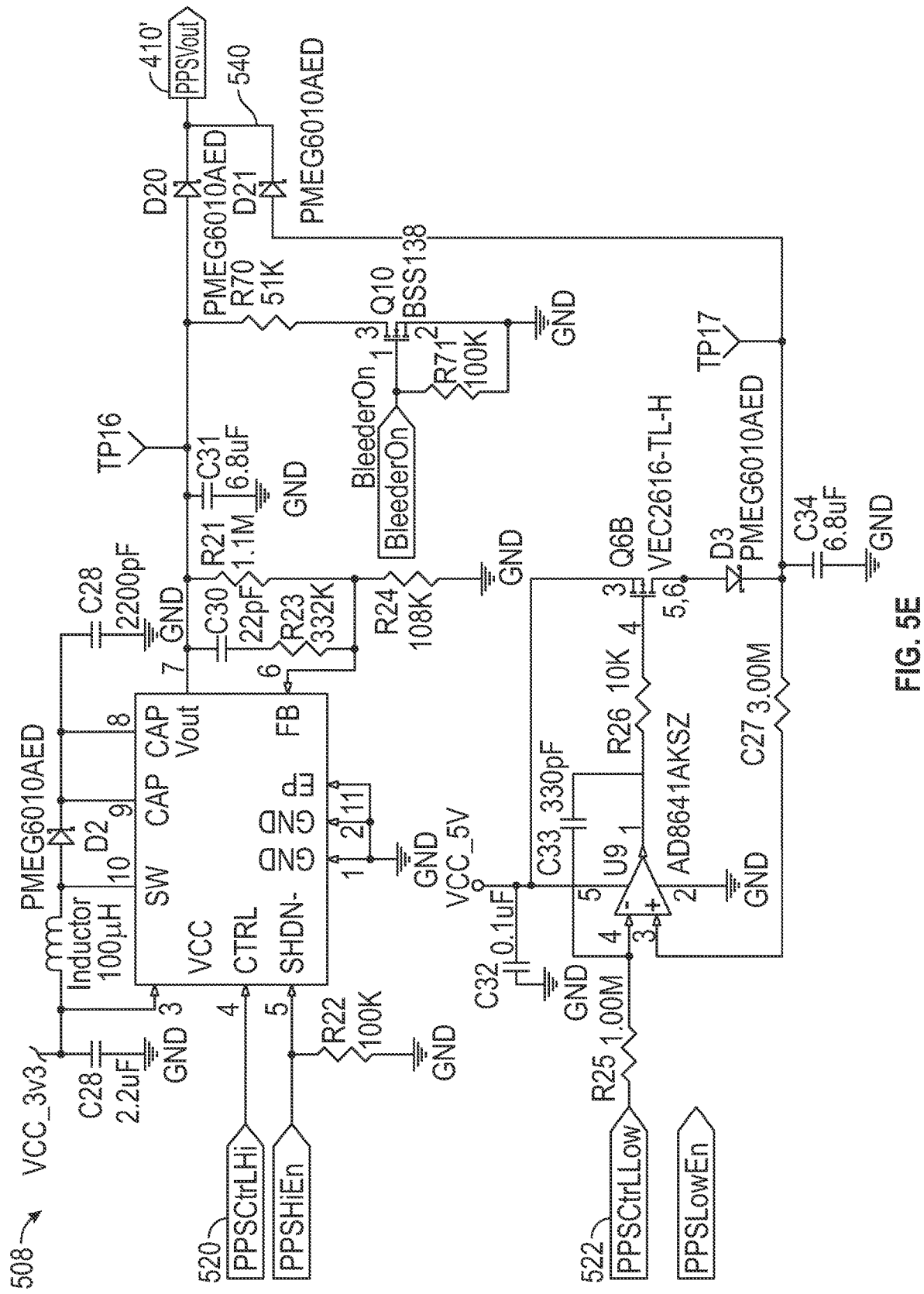
Figure 5F:
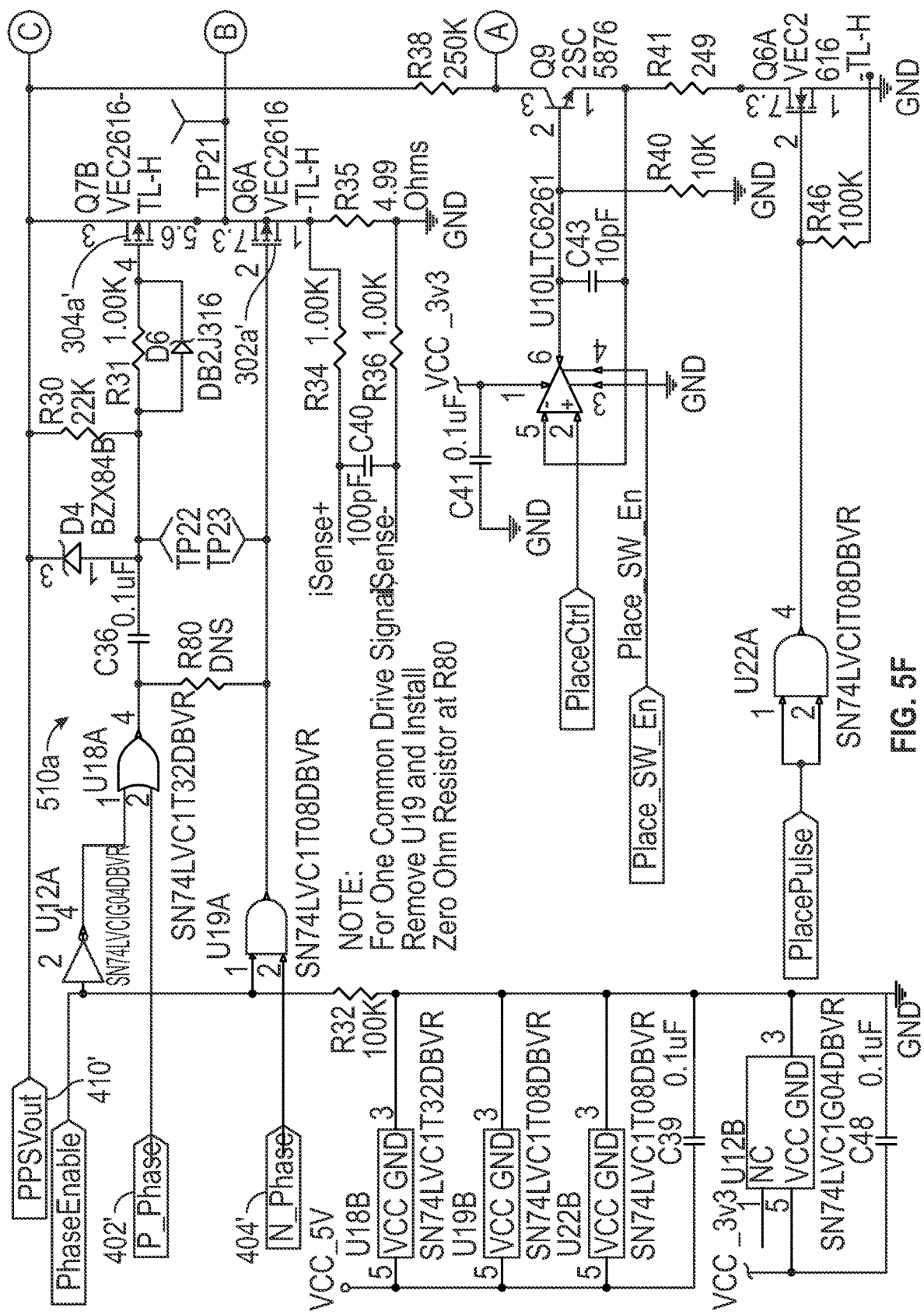
Figure 5F:
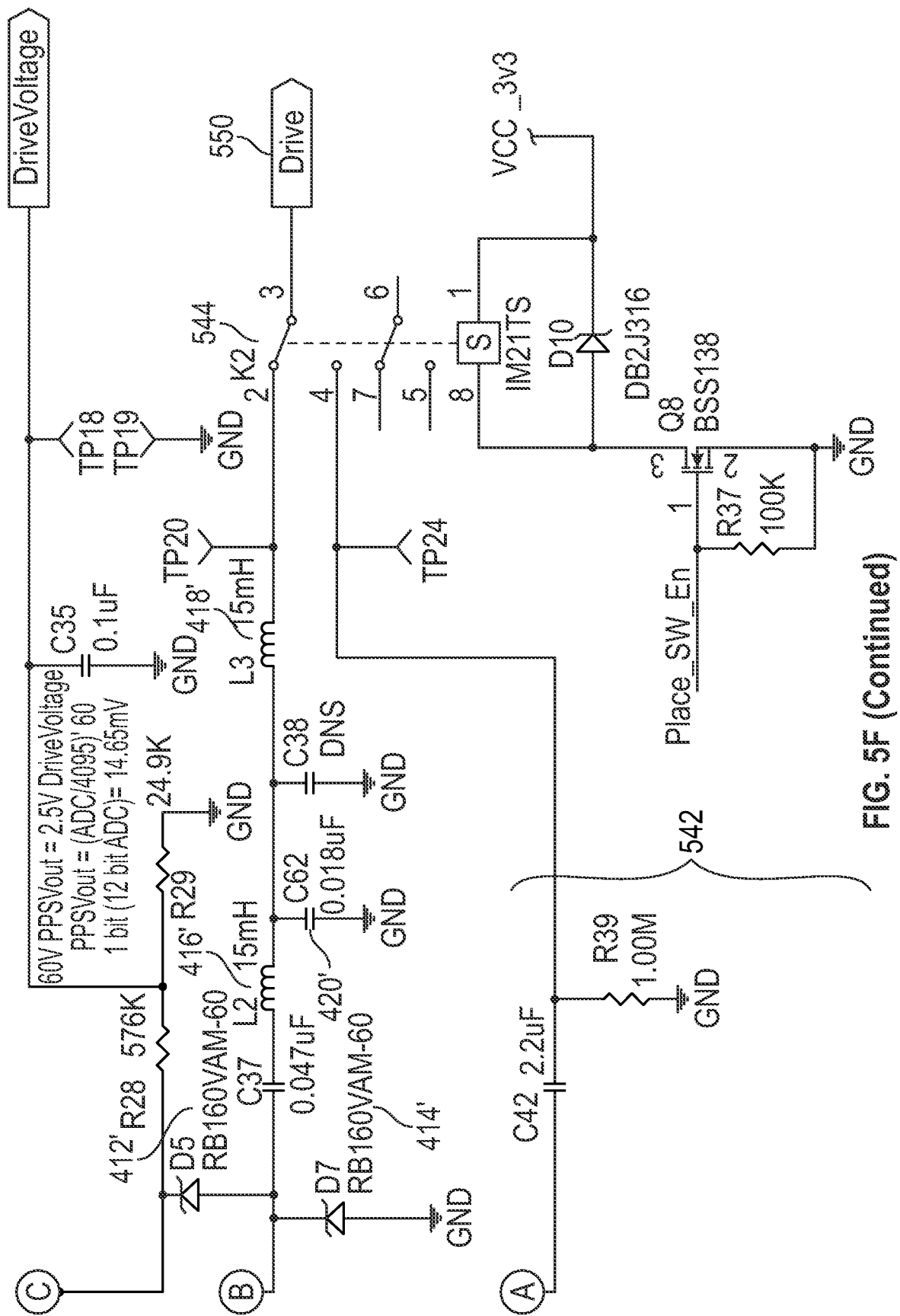
Figure 5F:
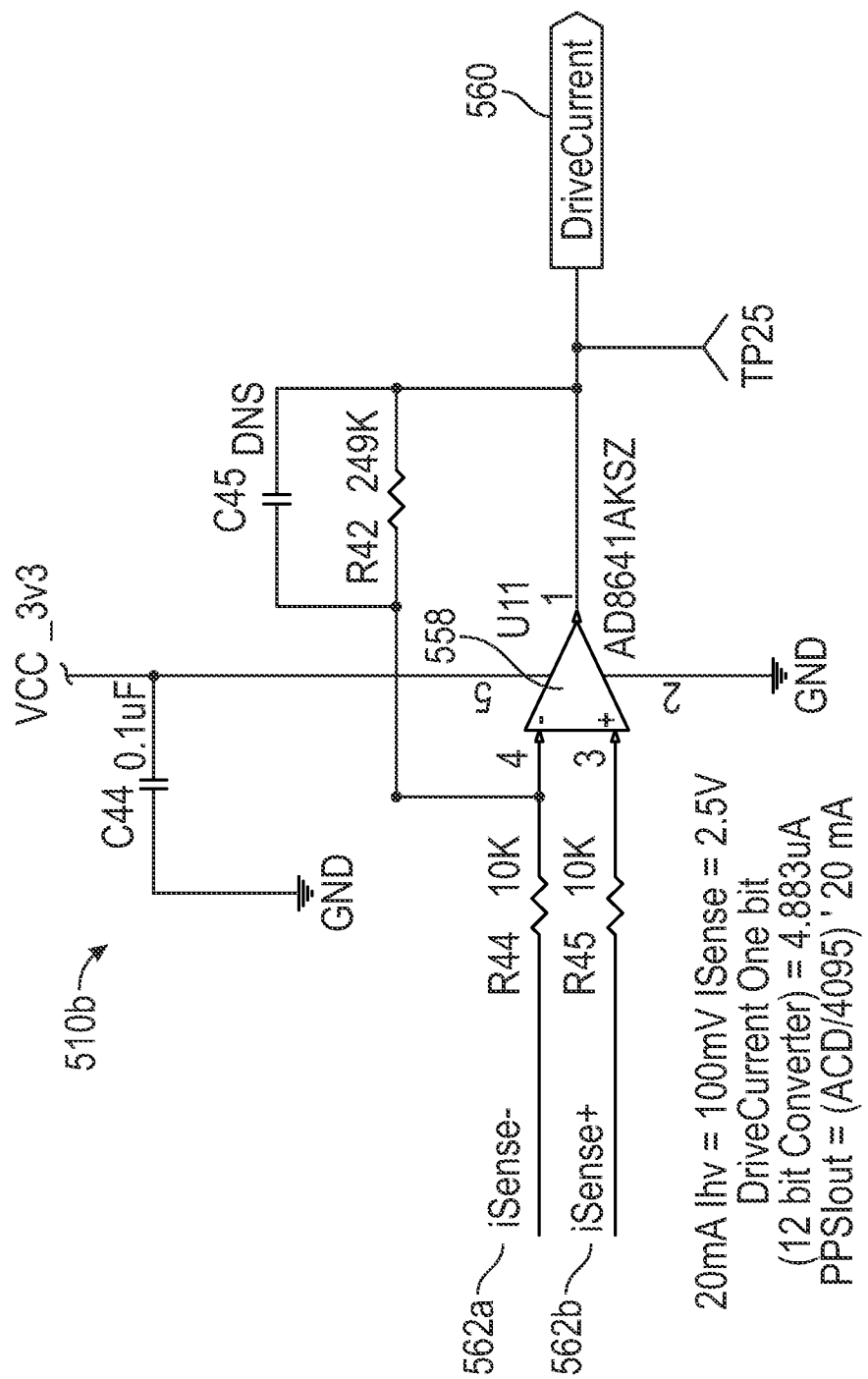
Figure 5G:
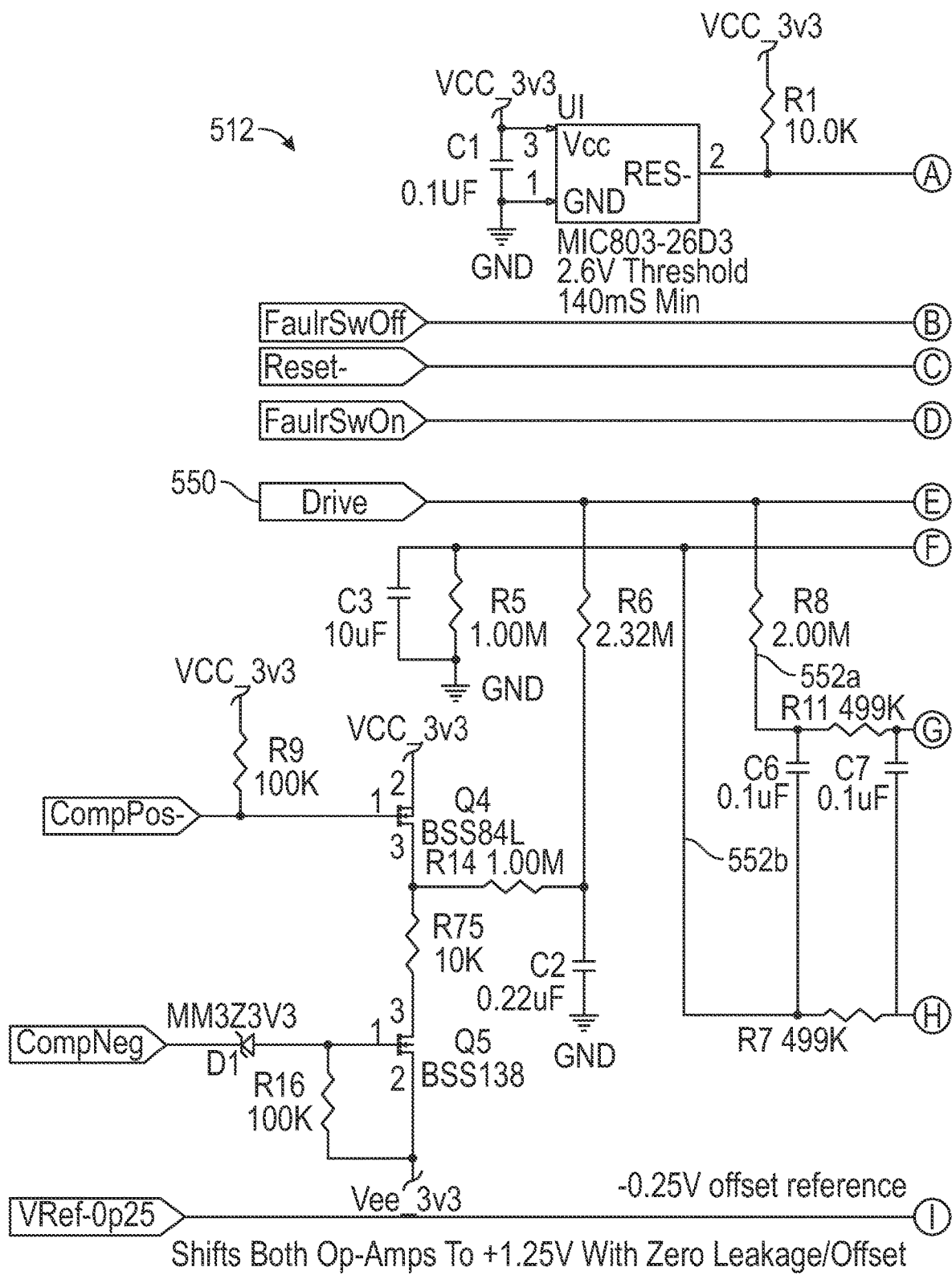
Figure 5G:
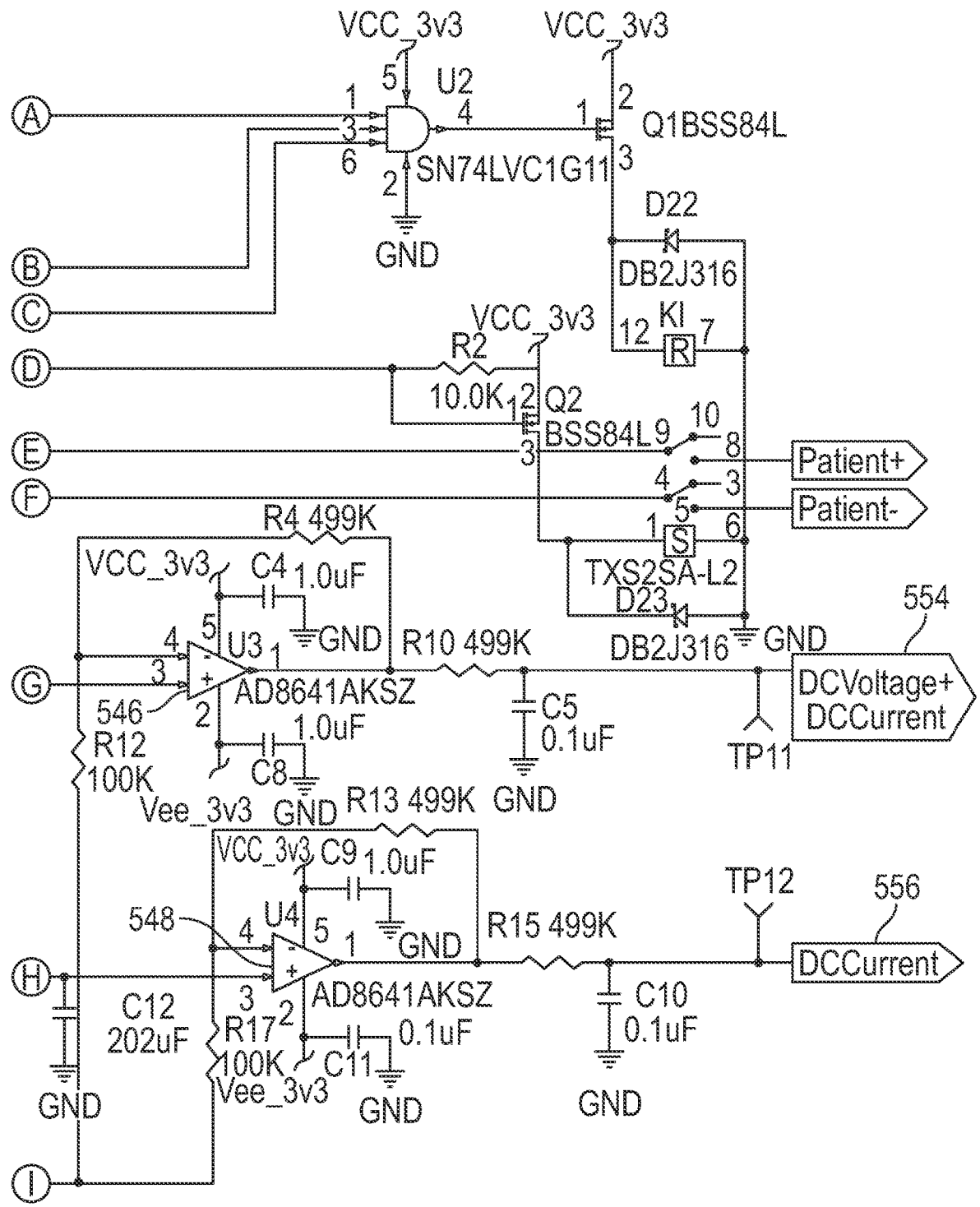

Specifically, FIG. 5A shows a high-level system diagram of an example portable electrical stimulation system of FIG. 1 or 2 in accordance with an illustrative embodiment. FIG. 5B shows a diagram of a controller circuit of FIG. 5A in accordance with an illustrative embodiment. FIG. 5C shows a diagram of supporting control circuit of FIG. 5A in accordance with an illustrative embodiment. FIG. 5D shows a diagram of a user interface circuit of FIG. 5A in accordance with an illustrative embodiment. FIG. 5E shows a diagram of a power supply circuit of FIG. 5A in accordance with an illustrative embodiment. FIG. 5F shows a diagram of a stimulation output circuit of FIG. 5A in accordance with an illustrative embodiment. FIG. 5G shows a diagram of a voltage and current monitoring circuit of FIG. 5A in accordance with an illustrative embodiment.

System Circuit. As noted above, FIG. 5A shows a system diagram of electronics and stimulation circuitries for an example portable electrical stimulation system 102 (shown as 500) in accordance with an illustrative embodiment. In FIG. 5A, the example portable electrical stimulation system 500 includes an electrical-stimulation generator (e.g. 114), a controller (e.g., 122), and user interface (e.g., 124a, 124b) implemented with one or more printed circuit board(s). The board(s) are housed in a housing (e.g., shown in FIG. 11). The controller (e.g., 122) and electrical-stimulation generator (e.g., 114) as shown in FIG. 5A includes a controller circuit 502 (shown as "MCU" 502), supporting circuitries 504 for the controller circuit 502 (shown as "MCU Support" 504), user interface circuit 506, power supply circuit 508 (shown as "ProgPwrSupply" 508), stimulation output circuit 510 (shown as "PowerOutput" 510), and voltage and current monitoring circuit 512 (shown as "DCVIMonitor" 512). FIGS. 5B-5G show example implementations of each of these sub-circuits.

In FIG. 5A, control inputs (e.g., intensity or amplitude selection) are provided from user interface elements (shown as "Button") to the user interface circuit 506. The user interface circuit 506 provides user-selected outputs (e.g., intensity settings/adjustments, device on/off, and stimulation enable/disable, etc.) to the controller 502, which send control signals to respective circuits (e.g., 508, 510, 512) directly as digital signals or as analog control signals via analog-to-digital converters located in the MCU supporting circuitries 504. The controller 502 can send voltage output control setpoints/levels to the programmable power supply circuit 508 (through ADC circuit(s) in 504), which is configured with a controllable variable voltage switching supply. The controller 502 can send stimulation control signals to the stimulation output circuit 510, which is configured to generate controlled current sinusoidal electrode drive signals for sinusoidal envelope amplitude control. The stimulation output circuit 510 generates the high-frequency stimulation waveform that is directed to the voltage and current monitoring circuit 512, which measures the sinusoidal current envelope amplitude and sinusoidal voltage envelope amplitude for their respective control as well as provide a connection 514 to the percutaneous lead (e.g., 110, 110a, 110b, 110c). Of course, other circuitries and topologies, particularly, those that are suitable for low-power operation may be used.

Controller Circuit. FIG. 5B shows a diagram of a controller circuit 502 of FIG. 5A in accordance with an illustrative embodiment. The controller circuit 502 includes a low-power microcontroller 516 (the specific part listed being manufactured by Texas Instruments) configured with flash and volatile memory, ADC, digital inputs and outputs, and serial communication, among other features, and an independent watchdog. The microcontroller is configured to execute instructions including operations as described in relation to FIG. 10. Other types of processing units may be used including application-specific circuits and general-purpose microprocessors. The controller 516 provides stimulation control signals (shown as "P Phase" 402' and "N Phase" 404') to the stimulation output circuit 510a (see FIG. 5F).

Supporting Control Controller Circuit. As noted above, FIG. 5C shows a diagram of the supporting control controller circuit 504 of FIG. 5A in accordance with an illustrative embodiment. As noted above, controller 502 is configured to send to respective circuits (e.g., 508, 510, 512) as analog command signals via an analog-to-digital converter 516 (the specific part listed being manufactured by Maxim Integrated) located in the MCU supporting circuitries 504. In FIG. 5C, the analog-to-digital converter 516 is configured to receive serial control signals from the controller 502 and generate a plurality of analog control signals 520 (shown as "PPSCtrlHi" 520), 522 (shown as "PPSCtrlLow" 522), and 524 (shown as "PlaceCtrl" 524). The controller 502 also provides a voltage reference output that is offset in the supporting control controller circuit 504 to provide a –0.25V offset reference 518 (shown as "Vref-0p25" 518) for the voltage and current sensing circuit in voltage and current monitoring circuit 512. In FIG. 5C, the supporting control controller circuit 504 is shown to further include a low density, low energy code storage memory devices 526 (the specific part number being manufactured by Adesto Technologies).

User Interface Circuit.

As noted above, FIG. 5D shows a diagram of the user interface circuit 506 of FIG. 5A in accordance with an illustrative embodiment. The user interface circuit 506 (shown as 506a) includes an ESD protection device 528 (the specific part number being manufactured by ST Microelectronics) and input circuitries for multi-button inputs (e.g., for connection to inputs/outputs 124a). In some embodiments, the button inputs (e.g., 124a) may correspond to an "on/off" button, a "stimulation on/off" button, an "intensity up" button, and an "intensity down" button. Of course, other UI circuitries and methodologies for inputs may be used, particularly, those that are suitable for low-power operation may be used.

The user interface circuit 506 (shown as 506b) includes a bus driver 530 to drive a plurality of LEDs (shown as "D12" to "D19") (e.g., corresponding to display 124b). The plurality of LEDs may be used to indicate an intensity level of the high-frequency electrical stimulation that is being outputted as well as output status indication for the system. Of course, other type of displays and display drivers may be used, particularly, those that are suitable for low-power operation may be used. Additionally, different number of LED elements may be used.

The user interface circuit 506 (shown as 506c) includes an audio driver circuit that includes an audio amplifier 532 (the specific part number being manufactured by Texas Instruments) to drive a speaker 534. The audio alert can be used to generate an audio output when there is an error detected, e.g., a hardware error, a lead disconnection, a detected fault condition.

Power Supply Circuit.

As noted above, FIG. 5E shows a diagram of the power supply circuit 508 of FIG. 5A in accordance with an illustrative embodiment. The power supply circuit 508 includes a controllable variable voltage switching supply device 536 comprising micro-low noise boost converter (the specific part manufactured by Linear Technology). The switching supply device 536 include a reference input, connected to control signal "PPSCtrlHi" 520, to which the internal feedback reference of the switching supply device 536 can be adjusted to control its output voltage (shown as "PPSVout" 410'). The power supply circuit 508 includes a second power supply, connected to control signal "PPSCtrlLow" 522, to provide output power 540 when the device is in sleep-mode/low-power mode.

Stimulation Output Circuit.

As noted above, FIG. 5F shows a diagram of a stimulation output circuit 510 of FIG. 5A in accordance with an illustrative embodiment. The stimulation output circuit 510 (shown as 510a) provides a circuit configured to generate controlled current sinusoidal electrode drive signals for sinusoidal envelope amplitude control. The stimulation output circuit 510a is configured with the exemplary stimulation generating circuit (e.g., 400 of FIG. 4 or 114a of FIG. 3). For the purpose of this example, description is provided in relation to the reference numbers and components of FIG. 4, though such description can be similarly applied to the reference numbers and components of FIG. 3.

In FIG. 5F, the stimulation output circuit 510a includes a set of switching circuit elements 302, 304 comprising an n-type MOSFET 302a (shown as 302a') and a p-type MOSFET 304a (shown as 304a') in which the drain of the p-type MOSFET 304a' is connected to the source of the n-type MOSFET 302a (302a'). The gates of the MOSFETs 302a' and 304a' are connected to output pins of the MCU Control 402, 404 (shown as "P Phase" 402' and "N Phase" 404') (per FIG. 4, it can be seen that the MCU Control 402' and 404' are pulse signals). The source of the p-type MOSFET 304a' is connected to the output of the programmable power supply 410 (shown as "PPSVout" 410') and voltage regulating diodes 412, 414 (shown as Zener diodes 412', 414'). The drain of the n-type MOSFET 302a' is connected to circuit ground. In FIG. 5F, the switching circuit elements 302a', 304a' are connected to a low-pass filter 314 comprising a set of inductive elements 416, 418 (shown as 416' and 418') and capacitive elements 420 (shown as 420'). Indeed, the LC low-pass filter is configured with component values suitable for high-frequency operation (including continuous high-frequency operation). The stimulation output circuit 510a may be used to generate a high-frequency electrical stimulation, e.g. similar to that shown and described in relation to those in FIG. 6A, 6B, or 7.

The stimulation output circuit 510a provides a power-efficient electrode driver circuit for sinusoidal and/or large duty cycle waveforms that includes an efficient variable voltage switching supply to provide high power efficiency and low power consumption. The stimulation output circuit 510a has a relatively small number of electronic components (providing an optimized implementation) that maintains performance over a wide range of power supply variations and amplitude modulation control.

FIG. 5F further shows an example placement stimulation circuit 542 and a relay assembly and circuit (544) coupled to an associated selector circuit that selects between the output of the stimulation output circuit 510a and the placement stimulation circuit 542 as the output 550 (shown as "Drive 550") of the system. The placement stimulation circuit 542 may be used to generate a placement pulse, e.g. similar to that shown and described in relation to those in FIG. 8.

Additionally, FIG. 5F shows a variable DC current injection circuit 322b (shown as 510b) that is configured to counteract the buildup of DC voltages across the electrode. The variable DC current injection circuit 510b includes a high impedance input amplifier 558 that senses DC voltages (shown as "ISense−" 562a and "ISense+" 562b), e.g., at the lead/electrode, to output (shown as "DriveCurrent" 560) a current output to mitigate such build-up.

Voltage and Current Monitoring Circuit.

As noted above, FIG. 5G shows a diagram of a voltage and current monitoring circuit 512 of FIG. 5A in accordance with an illustrative embodiment. Indeed, the voltage and current monitoring circuit 512 can measure sinusoidal current envelope amplitude and sinusoidal voltage envelope amplitude for the respective control of i) envelope amplitude voltage drive for controlled current output and ii) envelope amplitude voltage drive for controlled voltage output. In addition, the voltage and current monitoring circuit 512 includes a high impedance differential voltage sensing circuit (shown including 546 and 548) that is configured to detect differential DC voltage. In FIG. 5G, the two high impedance input amplifiers 546, 548 are respectively connected (see wire 552a and 552b) to the drive output signal 550 to provide DC voltage sensing output (shown as "DC Voltage+DC Current" 554) and DC current sensing output (shown as 554 and "DC Current" 556).

Additionally, as shown in FIG. 5G, the voltage and current monitoring circuit 512 includes a fault mitigation switching circuit that is configured to disengage the active circuits from the electrode in case of a circuit fault. As shown in FIG. 5G, the voltage and current monitoring circuit includes a DC current sensing circuit that is configured to sense circuit faults used in conjunction with fault mitigation switching circuit. As shown in FIG. 5G, the voltage and current monitoring circuit includes a high impedance differential voltage sensing circuit configured to detect differential DC voltage as a fault sensing input to the fault mitigation switching circuit. As shown in FIG. 5G, the same high impedance differential voltage sensing circuit (e.g., 546 and 548) is used to detect differential DC voltage for controls as well as for a fault sensing input. Indeed, the voltage and current monitoring circuit 512 can provide feedback to the MCU (e.g., 516) to drive the DC current injection amplitude with an amplitude and polarity that counteracts the DC contamination buildup.

Example High-Frequency Electrical Stimulation

Figure 6A:
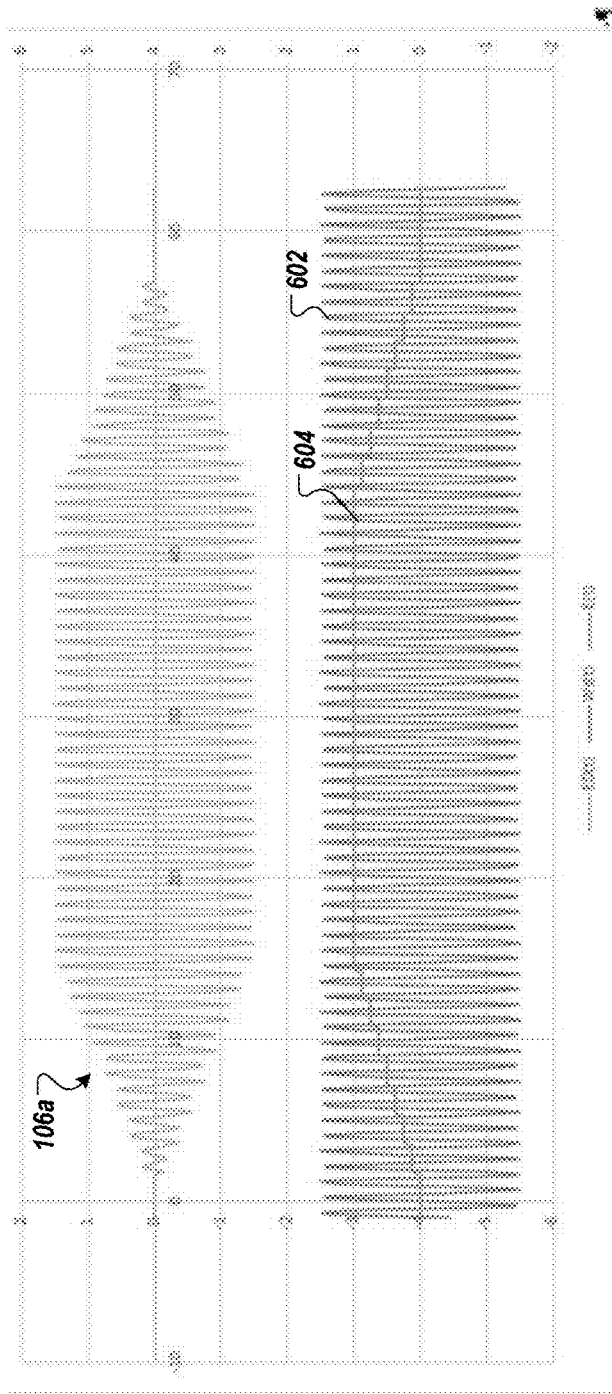
FIG. 6A shows an exemplary electrical stimulation generated by the portable electrical stimulation system in accordance with an illustrative embodiment.

FIG. 6A shows an exemplary electrical stimulation 106 (shown as 106a) generated by the portable electrical stimulation system 102 (e.g., from high-efficiency electrical-stimulation generator 114, e.g., of FIGS. 5A-5G) in accordance with an illustrative embodiment. In some embodiments, the exemplary electrical stimulation 106a comprises a voltage waveform having a maximum voltage of about 20 $V_{peak}$ and a current waveform having a maximum current of about 20 mA peak. For example, in some embodiments, the exemplary electrical stimulation 106a has a range between about +10V and −10V at −10 mA and 10 mA. In other embodiments, the exemplary electrical stimulation 106a has a range between about 0V and 20V at 0 mA and 20 mA. In some embodiments, the portable electrical stimulation system (e.g., 102, 202) is configured to limit charge density and charge per pulse to less than the Shannon criteria safe operating limit.

As shown in FIG. 6A, the electrical stimulation 106*a* is defined by a fundamental periodic waveforms, $W_x(f,t)$ (shown as 602), comprising a set of repetitive pulses (e.g., sinusoids) defined by frequency f over a time period t and an amplitude envelope, $E(t)$ (shown as 604) that modulate the amplitude of fundamental periodic waveforms (e.g., $ED(t) = E(t) \times W_x(f,t)$).

Figure 6B:
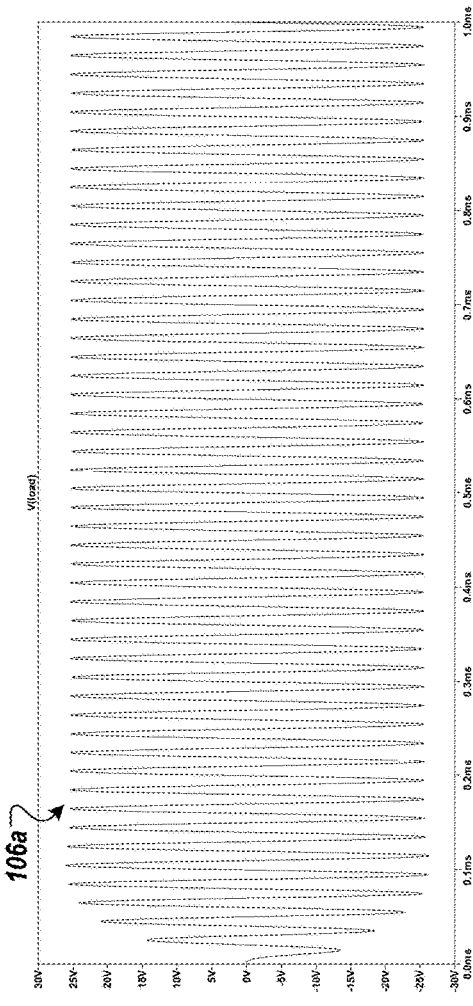
FIG. 6B shows another exemplary electrical stimulation comprising a 50 kHz sinusoidal output generated by the portable electrical stimulation system of FIG. 4 in accordance with an illustrative embodiment.

FIG. 6B shows another exemplary electrical stimulation 106*a* comprising a 50 kHz sine output generated by the portable electrical stimulation system 102 of FIG. 4 (e.g., from high-efficiency electrical-stimulation generator 114) in accordance with an illustrative embodiment. The electrical stimulation 106*a* can be any other frequency and waveform as discussed herein, including a sinusoidal waveform having a fundamental frequency harmonics around 10 KHz.

Figure 7:
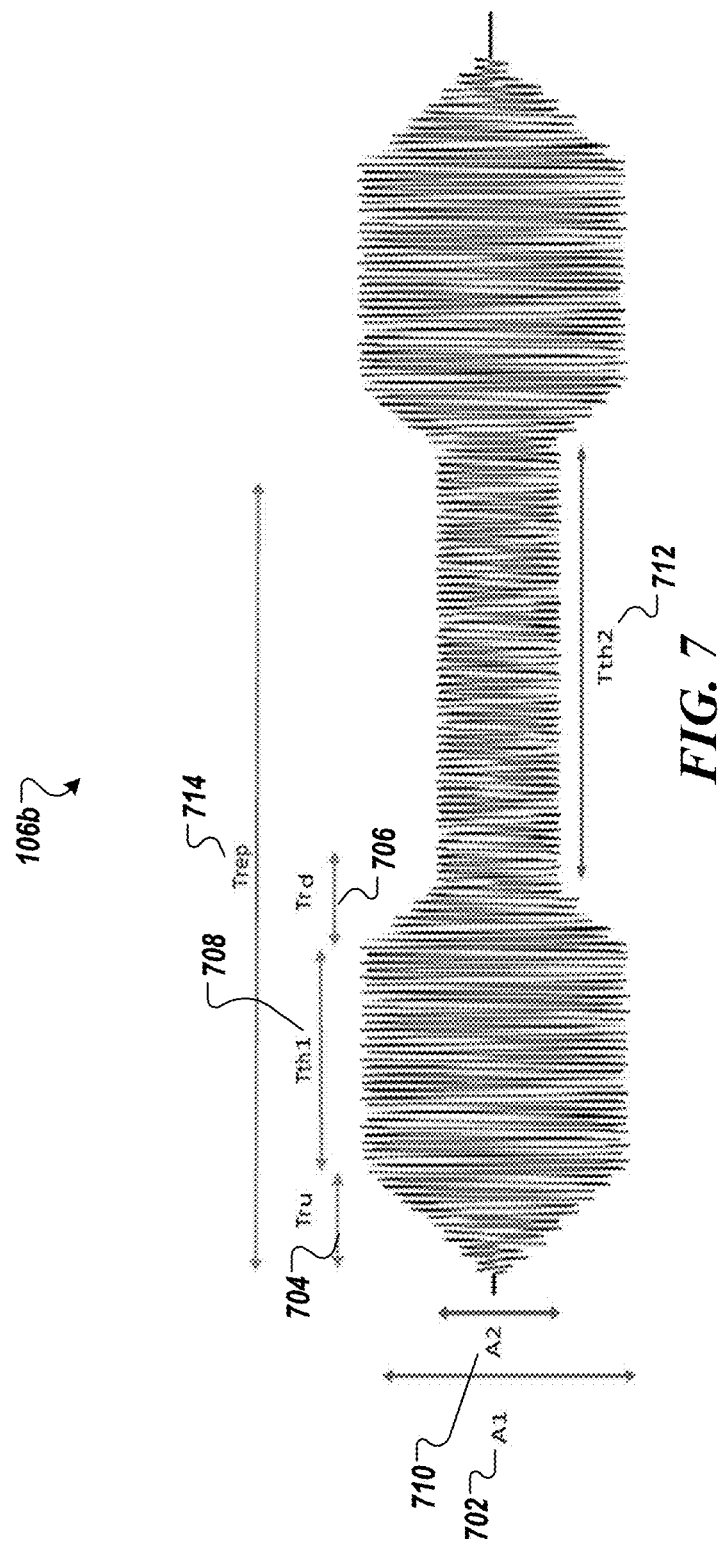
FIG. 7 is a diagram of another exemplary electrical stimulation generated by the portable electrical stimulation system in accordance with another illustrative embodiment.

FIG. 7 is a diagram of another exemplary electrical stimulation 106 (shown as 106*b*) generated by the portable electrical stimulation system 102 (e.g., from high-efficiency electrical-stimulation generator, e.g., 114, etc.) in accordance with another illustrative embodiment. The electrical stimulation 106*b* is parameterized to provide a plurality of complex stimulation waveforms, e.g., that does not produce onset response after the nerve has been blocked. A set of example parameters and description are provided in Table 1.

TABLE 1

| Parameter | Description | Units |
|---|---|---|
| "A1" (702) | Full Block Amplitude | mA |
| "Tru" (704) | Full Amplitude Ramp transition duration, up | S or number of cycles |
| "Trd" (706) | Full Amplitude Ramp transition duration down (could be set to zero) | S or number of cycles |
| "Tth1" (708) | Full amplitude therapy burst duration (could be set 'forever') | S or number of cycles |
| "A2" (710) | Sustaining Block Amplitude | mA |
| "Tth2" (712) | Full amplitude therapy burst duration (could be set "forever") | S or number of cycles |
| "Trep" (714) | Repetition Period for repetitive therapy bursts | S or number of cycles |
| #ThB (not shown) | Total number of therapy bursts applied from STIM ON start to automatic stop of therapy (could be set "indefinitely") | Number of Bursts |

Placement Assist Square Waveform Output

Figure 8:
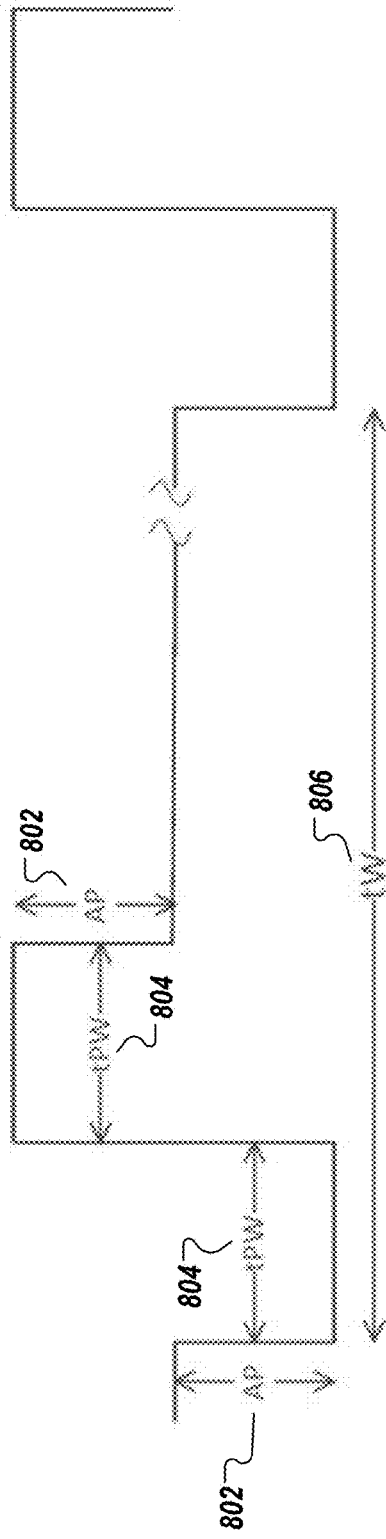
FIG. 8 is a diagram showing an example switching waveform output that can be generated by the electrical-stimulation generator for detecting nerve location and ideal electrode placement in accordance with an illustrative embodiment.

FIG. 8 is a diagram showing an example switching waveform output that can be generated by the electrical-stimulation generator 114 for detecting nerve location and ideal electrode placement in accordance with an illustrative embodiment. In FIG. 8, the switching waveform output 310 is shown as a biphasic balanced voltage waveform. A set of example parameters and description are provided in Table 2.

TABLE 2

| Symbol | Parameter | Units | Minimum | Maximum | Resolution |
|---|---|---|---|---|---|
| "AP" (802) | Pulse amplitude | V | 0 | 10 | 20 steps |
| "tPW" (804) | Pulse width | mS | 0.2-5% | 0.2 + 5% | NA |
| "TW" (806) | Pulse Waveform Period | S | 0.5-5% | 0.5 + 5% | NA |

In some embodiments, the parameter for the pulse waveform period (TW) is a constant value. The pulse amplitude (AP), in some embodiments, is linked to the intensity control values as provided by the user (e.g., via input/output 124*a*).

Figure 9:
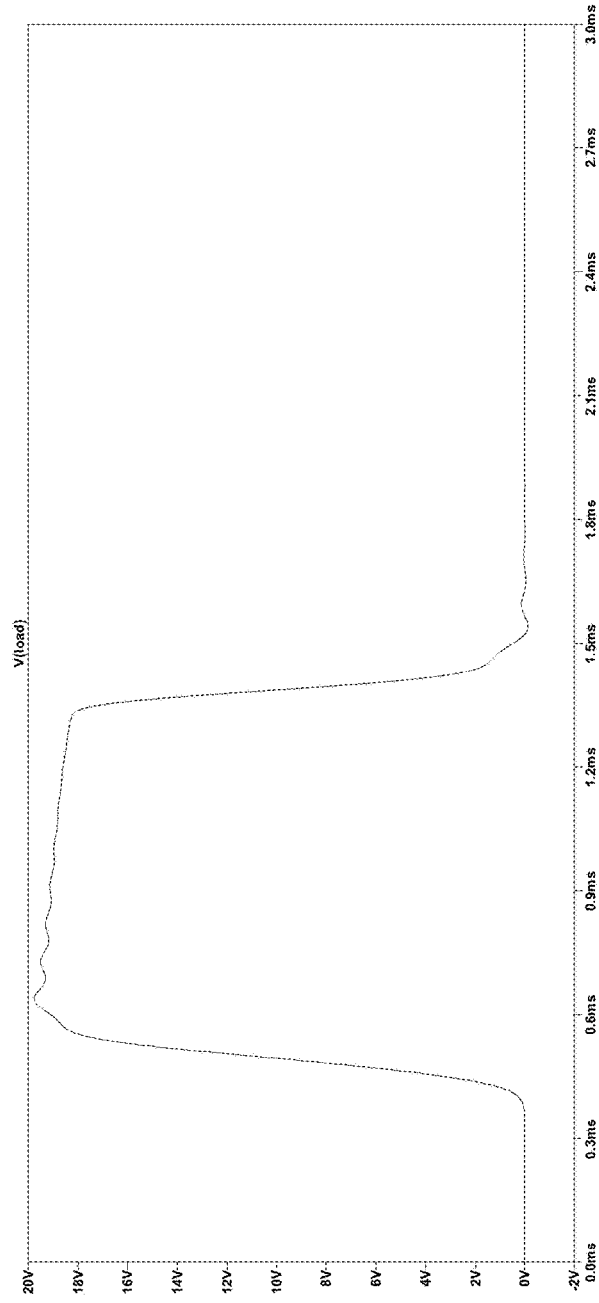
FIG. 9 shows an acquired placement assist square waveform in accordance with an illustrative embodiment.

In some embodiments, the electrical-stimulation generator (e.g., 114, 114*a*, 400, 500) is configured to generate the placement-assist waveform amplitude and then transition to a therapeutic electrical stimulation. In other embodiments, the electrical-stimulation generator (e.g., 114, 114*a*, 400, 500) is configured to generate a set of pre-defined placement-assist waveform outputs and feedback of the stimulation are then assessed to determine the characteristics of the placement of the electrode. The controller then directs the electrical-stimulation generator 114 to continuously output the electrical stimulation after that assessment. FIG. 9 shows an acquired placement assist square waveform in accordance with an illustrative embodiment.

Figure 10:
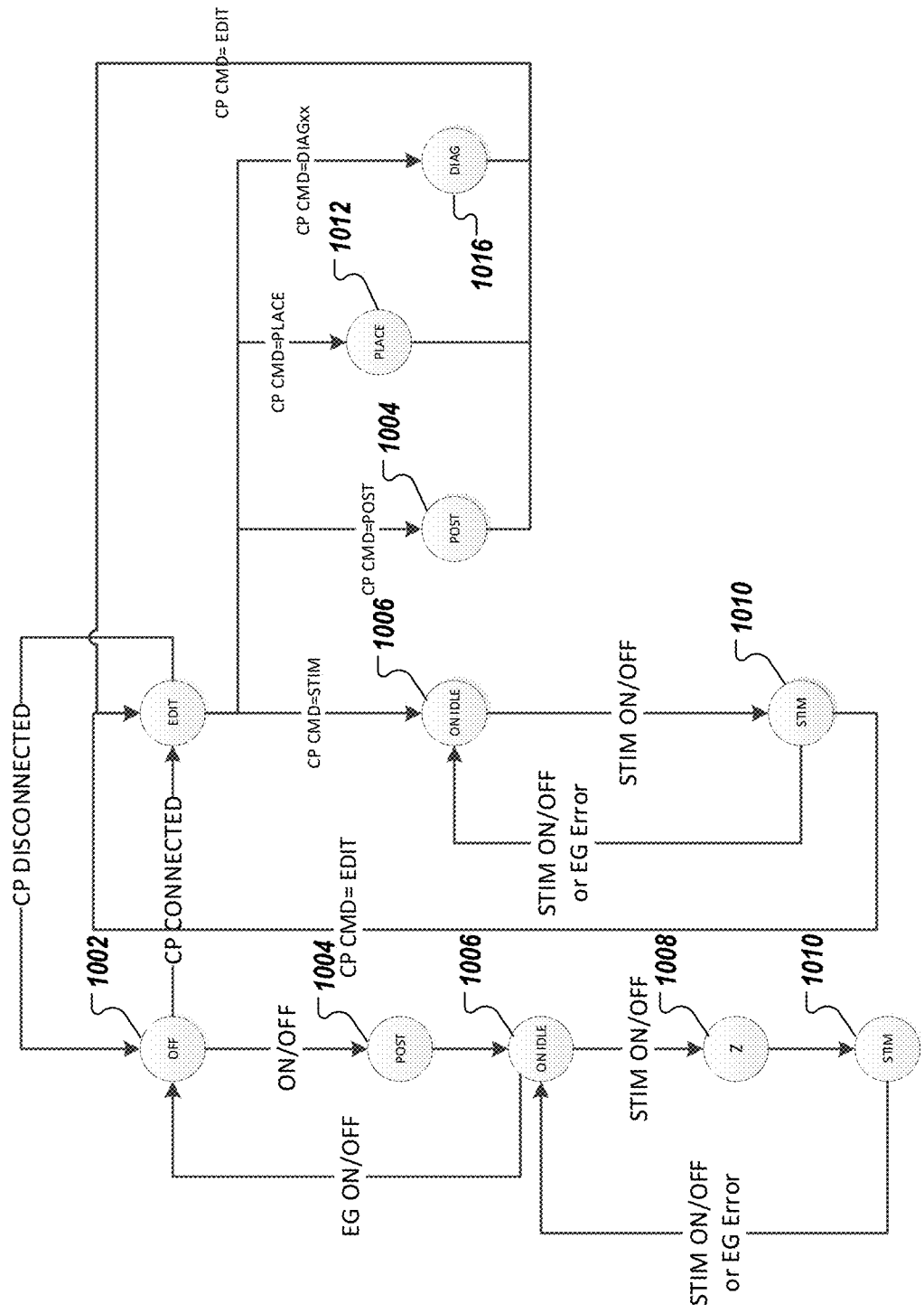
FIG. 10 is a diagram showing example operating states for the portable electrical stimulation system in accordance with an illustrative embodiments.

FIG. 10 is a diagram showing example operating states for the portable electrical stimulation system (e.g., 102, 202, etc.) in accordance with an illustrative embodiments. Description of the various example states as shown in FIG. 10 are provided in Table 3.

TABLE 3

| State | Action | Description |
|---|---|---|
| "OFF" (1002) | None. | EG ("electrical-generation") is Off and consumes minimal power. |
| "POST" (1004) | Perform POST, then exit. | Perform "power on self-test" (POST). |
| "ON IDLE" (1006) | Read status. Respond and provide output corresponding to EG Status | Idle state; no stimulation; wait for EG initiated commands. If the "ON IDLE" state was entered due to an EG error condition, then display the EG error type. |
| "Z" (1008) | Measure impedance. | |
| "PLACE" (1012) | Apply lead placement assist square waveform. Modify square wave amplitude using EC intensity controls. | Apply lead placement-assist square waveform. |
| "STIM" (1010) | Output electrical stimulation. Modify. Read Status. Output EG Status. Charge Balance. | Apply KHFAC ("kilohertz high-frequency AC") sinusoidal stimulation and related functions in accordance with settings. |
| "UPLOAD" (1014) | Upload EG stored data (log) to CP | Upload EG stored data (log) to CP (controller/processor). May include EG settings. |
| "DIAG" (1016) | Any commanded Action: Initiate tests. Perform test with fixture. Impedance check. Memory tests, calibration, etc. | Perform On-Demand diagnostics. |

Experimental Results

FIGS. 12-19 show results of experiment in which various high-frequency stimulation had been applied to a target nerve to treat acute pain without producing an onset response in the patient in accordance with an illustrative embodiment.

Example #1

Figure 12:
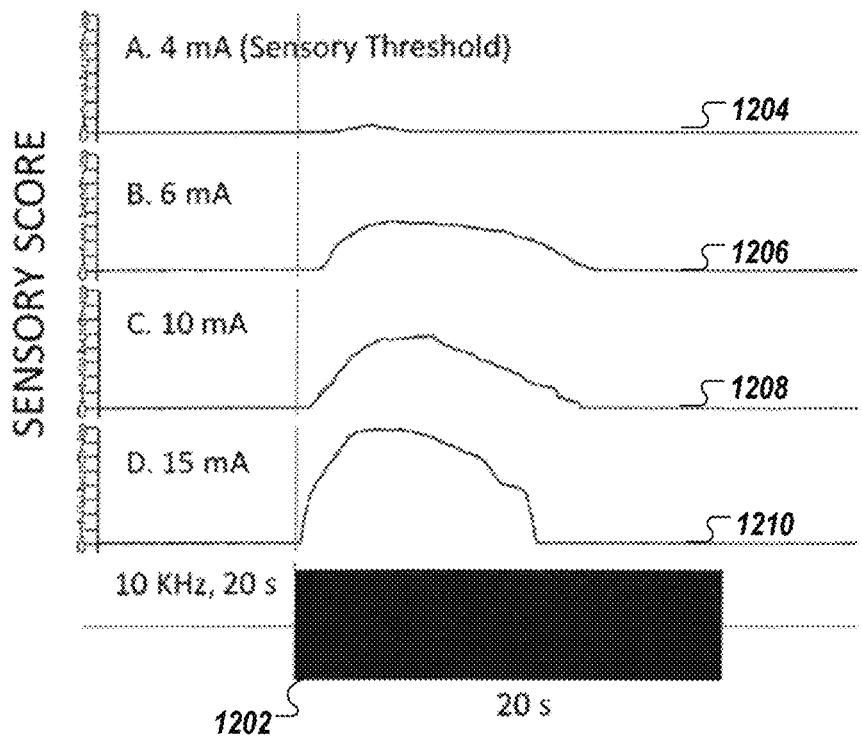
FIGS. 12 and 13 each shows a plot of a measured sensory response collected from a patient/subject in response to the application of a 10-kilohertz electrical stimulation (comprising electrical energy in the form of a sinusoidal waveform) being delivered percutaneously to the saphenous nerve of the patient in accordance with an illustrative embodiment.

FIG. 12 demonstrates a sensory response in an able-bodied subject to a percutaneously delivered high-frequency electrical stimulation. The sensations are consistent with the onset response elicited by high-frequency stimulation of a sensory nerve. An S8 (Abbott) electrode was used to stimulate the saphenous nerve at a site 5-to-10 cm proximal to the ankle. The stimulation consisted of a constant-current, 10 kHz sinusoidal waveform, and it was delivered for a period of 20 seconds at various amplitudes, including 4 mA (A—see reference number 1204), 6 mA (B—see reference number 1206), 10 mA (C—see reference number 1208), and 15 mA (D—see reference number 1210). The subject verbally described the quality of the evoked sensations (e.g. light-touch or pain) and indicated the intensity of the sensation on an 11-point scale: levels 1 and 2 defined tactile sensation, level 3 defined the pain threshold, and levels 4-10 indicated a mild-to-severe painful sensation.

In general, high-frequency stimulation delivered at 4 mA elicited a barely perceptible sensation (i.e. sensory-threshold) that faded within seconds, and before the high-frequency stimulation was terminated. Sensory-threshold was determined as the weakest stimulation intensity (10 cycles of a 10-kHz sinewave; 1 ms stimulation duration) that the subject could detect. High-frequency stimulation with an intensity of about 150% of sensory-threshold (6 mA), elicited a sensation consistent with the subject's threshold for pain (sensory score of 3), which again faded to baseline before the stimulation was terminated.

Table 1 shows the average (±standard deviation) sensory response to high-frequency electrical stimulation in an able-bodied subject delivered percutaneously, and with various stimulation amplitudes. Table 1 also provides the various criteria used to describe the sensory response. Criteria includes: 1. Peak sensory score (11-point scale); 2. Response area (in units, mA*s); 3. Onset latency, or minimal time to feel the sensory response (in seconds); 4. Peak latency or time to feel the peak sensation/sensory score (in seconds), and 5. Offset time for the sensory response to cease (in seconds). Indeed, FIG. 12 and Table 1 show that the peak sensation and response area increased with the amplitude of the high-frequency electrical stimulation, while the onset latency decreased. Peak latency and offset latency were more variable. It was also observed that the elicited sensations always terminated within seconds of it being evoked.

At a 6-mA stimulation intensity, the peak sensation ranking was 3.26 on the 11-point scale, and the subject described the sensory response as a sensation that increased quickly. Further, it took an onset time of 1.04 seconds for the subject to indicate a sensory response was felt and 11.09 seconds of offset time for the subject to indicate the sensory response had ceased, and the latency or amount of time to feel the peak sensory response was 3.99 seconds. Further the response area was 20.5 mA*s, indicating that the intensity of the sensory response was increased compared to the 4-mA stimulation.

At a 10-mA stimulation intensity, the peak sensation ranking was 4.95 on the 11-point scale, and the subject described the sensory response as sharp at the beginning, although after some time the sharpness went away along with any other sensation. Further, it took an onset time of 0.60 seconds for the subject to indicate a sensory response was felt and took 11.67 seconds of offset time for the subject to indicate the sensory response had ceased, and the latency or amount of time to feel the peak sensory response was 3.85 seconds. Further the response area was 38 mA*s indicating that the intensity of the sensory response increased compared to both the 4-mA and 6-mA stimulation.

At a 15-mA stimulation intensity, the peak sensation ranking was 7.54 on the 11-point scale, and the subject described the sensory response as painful at the beginning but also indicated that the pain went away quickly. Further, it took an onset time of 0.39 seconds for the subject to indicate a sensory response was felt and took 10.87 seconds of offset time for the subject to indicate the sensory response had ceased, and the latency or amount of time to feel the peak sensory response was only 2.52 seconds. Further the response area was 58.74 mA*s, indicating that the intensity of the sensory response was increased compared to the 4 mA, 6 mA, and 10 mA stimulations.

Further, the 6-mA stimulation was determined to be the stimulation intensity at which the pain threshold was reached, where the pain threshold was also associated with a peak sensation/sensory score of greater than or equal to 3. Example #1 also indicated that as the stimulation intensity was increased, the sensory score increased, the sensory response area increased, and the onset latency decreased.

TABLE 1

| Amplitude (mA) | Peak Sensation (0-11 Scale) | Response Area (mA*s) | Onset (seconds) | Peak Latency (seconds) | Offset (seconds) |
| --- | --- | --- | --- | --- | --- |
| 4 | 0.35 (±0.09) | 0.64 (±0.22) | 1.82 (±0.31) | 3.55 (±0.12) | 5.72 (±1.0) |
| 6 | 3.26 (±0.32) | 20.5 (±7.52) | 1.04 (±0.31) | 3.99 (±0.41) | 11.09 (±2.93) |
| 10 | 4.95 (±0.58) | 38.0 (±7.99) | 0.60 (±0.09) | 3.85 (±0.31) | 11.67 (±1.36) |
| 15 | 7.54 (±0.27) | 58.74 (±4.82) | 0.39 (±0.03) | 2.52 (±0.67) | 10.87 (±0.36) |

Table 1 shows the average sensory response to 20 seconds of 10 kHz percutaneous electrical stimulation at varying current amplitudes (n=3, ±standard deviation).

As shown in Table 1, at a 4-mA stimulation intensity, the peak sensation ranking was 0.35 on the 11-point scale, and the subject described the sensory response as a vibration that fades. Further, it took an onset time of 1.82 seconds for the subject to indicate a sensory response was felt and took only 5.72 seconds of offset time for the subject to indicate the sensory response had ceased, and the latency or amount of time to feel the peak sensory response was 3.55 seconds. Further the response area was 0.64 (mA*s) indicating that the intensity of the sensory response was low.

In addition, although the 15-mA stimulation was considered painful initially, it was determined that the 15-mA stimulation was successful at nerve blocking after the initial painful onset response, as indicated by the fact that the pain quickly went away. As such Example #2 was carried out to focus on minimizing the onset response at the 15-mA stimulation intensity, as discussed in more detail below.

Example #2

Figure 13:
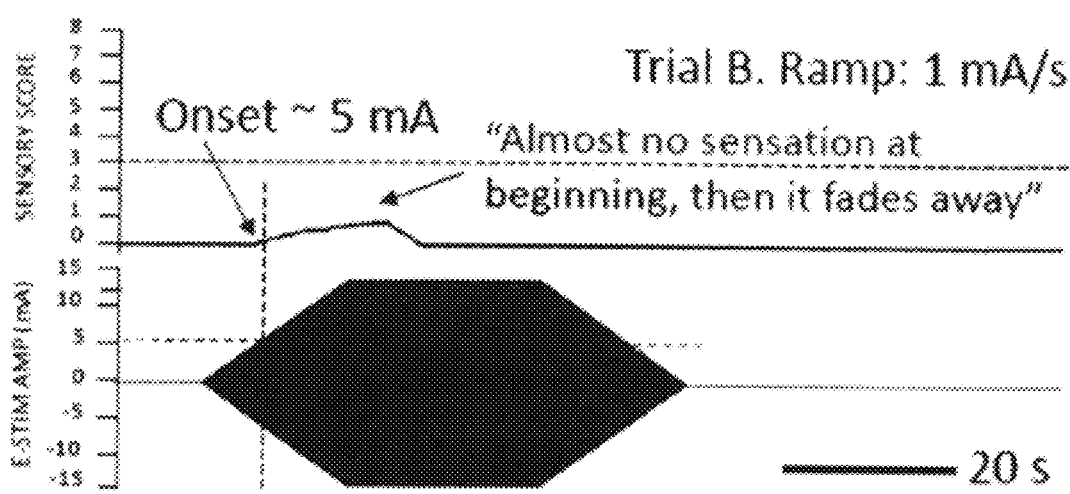
Figure 14:
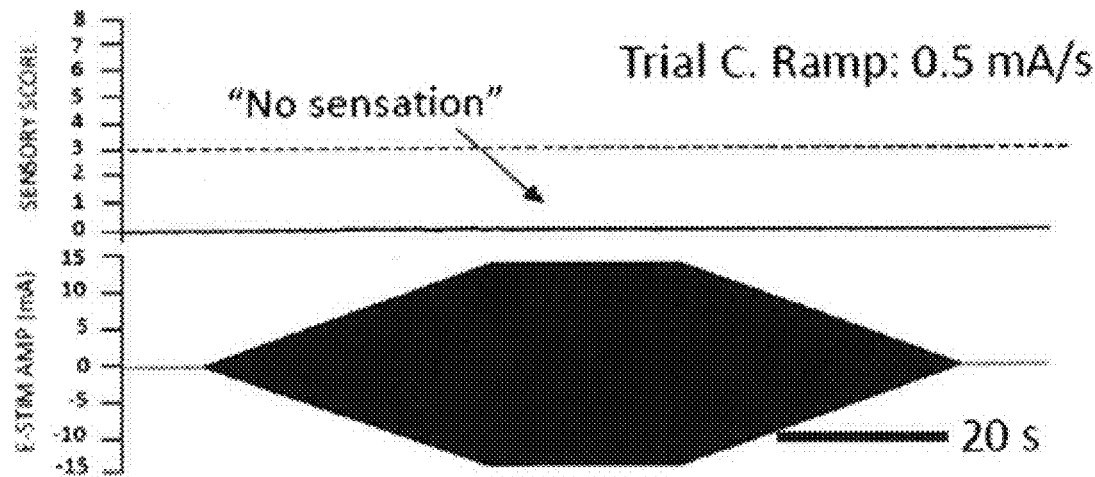
FIG. 14 is a plot showing a measured sensory response collected from a patient/subject in response to the application of another 10-kilohertz electrical stimulation with ramping profile in accordance with an illustrative embodiment.

To determine if the onset response experienced when a 15-mA stimulation was delivered to the saphenous nerve could be minimized or eliminated, various ramping conditions were tested where the amplitude was allowed to gradually increase to the 15-mA level rather than being immediately set to 15-mA, after which time the 15-mA stimulation was delivered for a time period of 20 seconds. Specifically, the data from the 15-mA stimulation from Example #1 where no ramping was utilized was compared to two different ramping rates—(1) 1 milliamp/second and (2) 0.5 milliamps/second. The results are shown in FIGS. 13-14 and Table 2 below.

TABLE 2

| Amplitude (mA) | Peak Sensation (0 to 8 Scale) | Response Area (mA * s) | Onset (seconds) | Peak Latency (seconds) | Offset (seconds) | Onset-Amp (mA) |
|---|---|---|---|---|---|---|
| 15 (no ramp) | 7.54 (±0.27) | 58.74 (±4.82) | 0.39 (±0.03) | 2.52 (±0.67) | 10.87 (±0.36) | NA |
| 15 (1 mA/s ramp) | 0.81 (±0.02) | 7.08 (±0.94) | 5.89 (±0.38) | 16.56 (±2.35) | 20.67 (±1.78) | 5.3 (±0.26) |

Table 2 shows an average sensory response to a 20-seconds 10 kHz percutaneous electrical stimulation at 15-milliamps current amplitude (n=3, ±standard deviation).

FIG. 14 shows results to an electrical stimulation in which a ramp rate of 1 milliamp per second was utilized to gradually increase the electrical stimulation to a desired 15-mA stimulation intensity was reached. As observed in FIG. 28B, the peak sensation ranking was reduced significantly to 0.81 on the 11-point scale, and the subject described the sensory response as feeling almost no sensation at the beginning, where the sensation quickly faded away. The sensory response was first felt when the amplitude reached about 5.3 mA. Further, it took an onset time of 5.89 seconds for the subject to indicate a sensory response was felt and took 20.67 seconds of offset time for the subject to indicate the sensory response had ceased, and the latency or amount of time to feel the peak sensory response was increased to 16.56 seconds. Further the response area was 7.08 mA*s.

Figure 15:
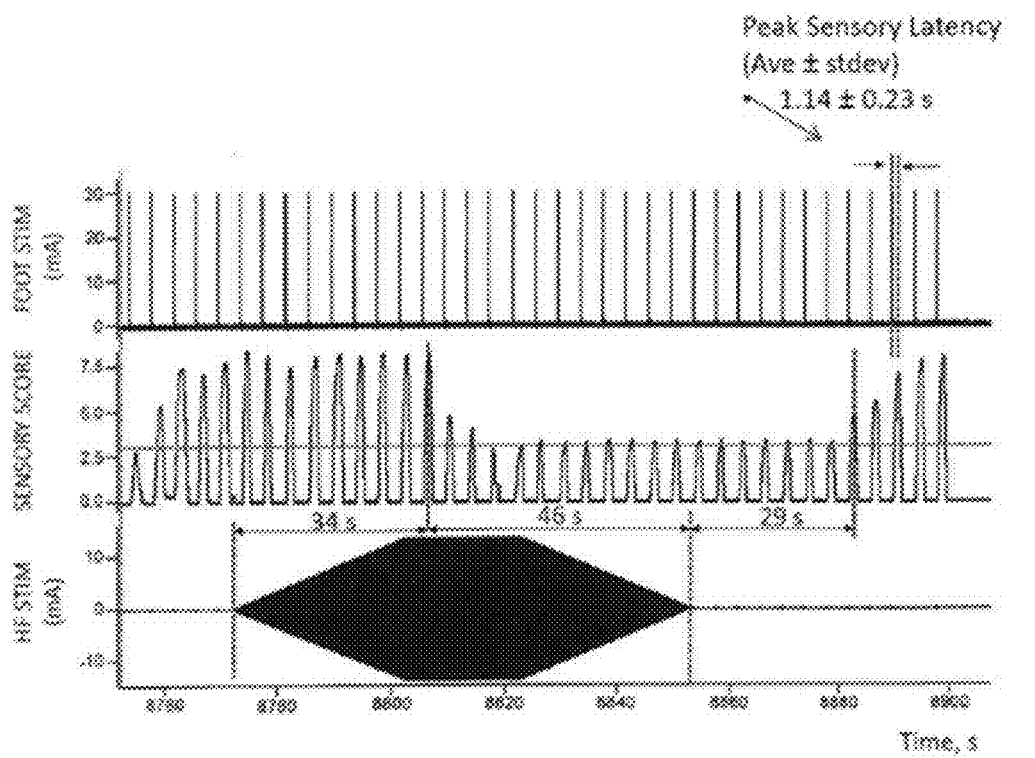
FIG. 15 is a plot showing a measured sensory response collected from a patient/subject in response to the concurrently application of a 10-kilohertz electrical stimulation and a pain stimulation in accordance with an illustrative embodiment.

FIG. 15 shows results to an electrical stimulation in which a ramp rate of 0.5 milliamps per second was utilized to gradually increase the electrical stimulation the until a desired 15-mA stimulation intensity was reached. It was observed that the peak sensation ranking was 0 on the 0 to 11 scale, and the subject described feeling no sensation at all for the sensory response, indicating that the presence of an offset response was completely eliminated. The sensory response was first felt when the amplitude reached about 5.3 mA. As such, all of the measured values are 0.

Indeed, it was observed that ramping the electrical stimulation gradually to a desired or pre-defined stimulation intensity or amplitude provided a peak sensation/sensory response level that is less than the baseline (same stimulation but without ramping); the response area is less than the baseline, the time to reach the onset response took longer than the baseline, the peak latency time took longer than the baseline; and the offset time took longer than the baseline.

Example #3

Figure 16:
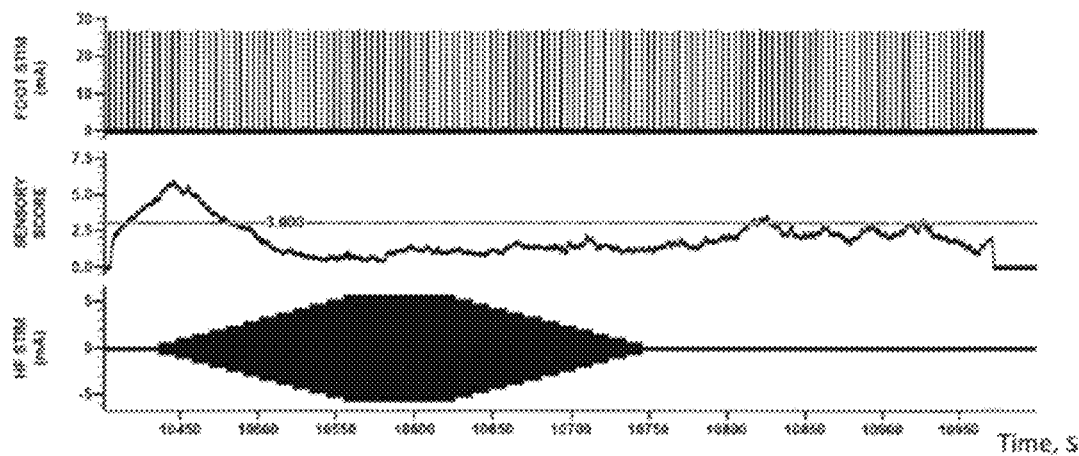
FIG. 16 is a plot showing a measured sensory response collected from a patient/subject in response to the concurrently application of a 10-kilohertz electrical stimulation and a pain stimulation in accordance with an illustrative embodiment.

The following results shows the ability to block acute pain sensations with high-frequency electrical stimulation delivered in a percutaneous fashion. FIG. 16 is a diagram of experimental results illustrating sensory responses to a sinusoidal waveform at various levels delivered percutaneously to the saphenous nerve, while pain inducing electrical stimulation was concurrently applied to the subject. Specifically, FIG. 16 demonstrates the effect of high-frequency electrical stimulation in blocking acute pain sensations in 2 able-bodied subjects.

In FIG. 16, a conventional electrical stimulation (9 pulses train, 500 Hz, 1 millisecond pulse width, about 28 mA amplitude, inter-train interval of 4 seconds) was again delivered to the subject's foot over-top of the saphenous nerve to elicit painful sensations to simulate/cause acute pain. Then, a high-frequency electrical stimulation was percutaneously delivered to the saphenous nerve at a site proximal to the ankle, and with a ramp rate of 0.05 mA/s, and a 5.5 mA plateau lasting 91 seconds. It was observed that, prior to application of the high-frequency stimulation to block the pain, the subjective sensory score was recorded with a maximum level of about 6 and, and during application of the high-frequency stimulation, a minimum level of about 1 was observed. Here, the amplitude of the high-frequency electrical stimulation was again approximately 4 times the sensory-threshold, or 1.3 mA. It was observed that the reduction in sensory score continued after termination of the high-frequency stimulation and for the duration of the trial that was about 270 seconds. Incidentally, the subject's sensory score recovered to 7.5 after a few minutes of rest and prior to the following trial.

Indeed, in the tested subjects, lower ramping rates were observed to provide longer lasting and more pronounced reduction in elicited painful sensations at the foot.

Example #4

Figure 17:
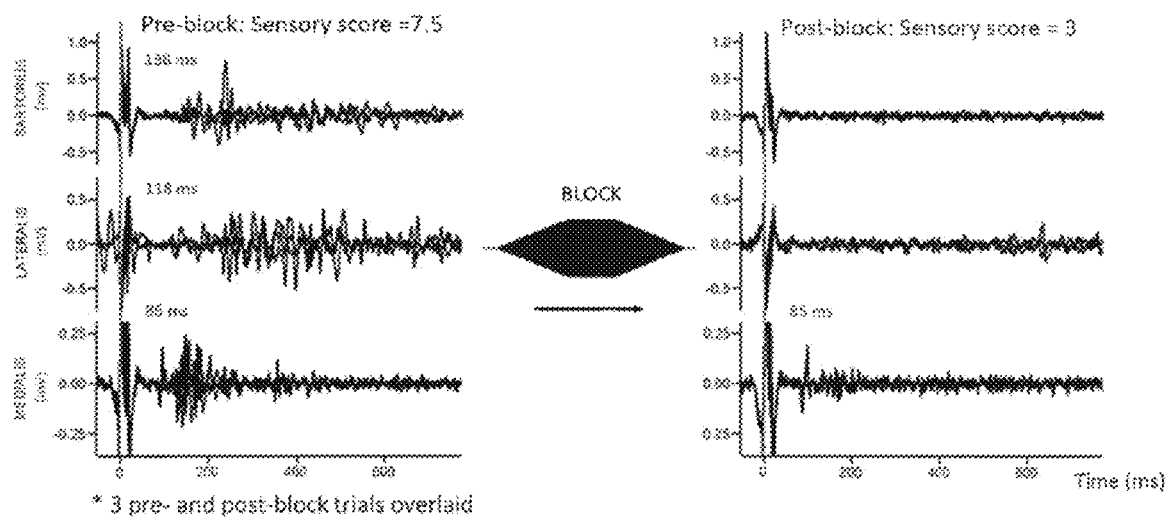
FIG. 17 is a plot illustrating observed effects of percutaneous high frequency electrical stimulation of the saphenous nerve at a site proximal to the ankle on the nociceptive reflex elicited by conventional electrical stimulation of the nerve at the foot in accordance with an illustrative embodiment.

FIG. 17 further demonstrates results of percutaneous high-frequency electrical stimulation in blocking the nociceptive reflex. Electromyogram (EMG) signals were recorded from the vastus medialis, vastus lateralis and sartorius muscles in response to painful electrical stimulation that is delivered to the foot over-top of the saphenous nerve to simulate/cause acute pain. The resultant bursts of EMG, hosted by the nociceptive reflex, are considered a quantitative method for assessing pain in humans. The plots on the left side and right side of FIG. 17 show stimulus-elicited bursts of EMG before and after high-frequency electrical stimulation (10 kHz) were delivered percutaneously to the saphenous nerve at a site proximal to the ankle. Three overdrawn trials represent each data trace. Prior to high-frequency electrical stimulation, the nociceptive reflexes were elicited in all 3 muscles tested (left side plot) with latencies ranging from 85 ms to 160 ms. Stimulus-elicited bursts of EMG were largely absent immediately following the stimulation (right side plot). The average sensory score reported by the subject during the time periods describing EMG activity decreased from 7.5 to 3 (pain-threshold). Indeed, these data suggest that the mechanisms responsible for reductions in pain sensation may be attributed to nerve block, and not by higher-order processes.

Example #5

Figure 18:
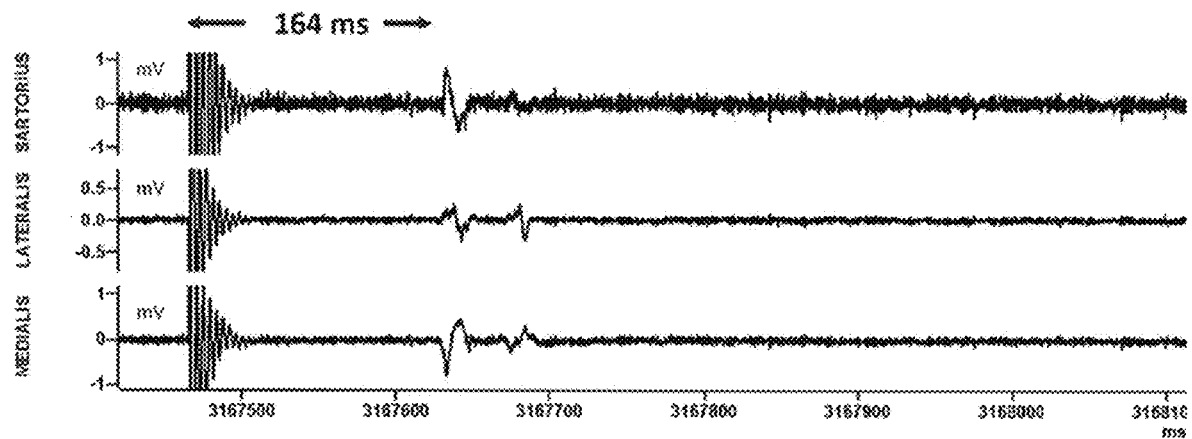
FIG. 18 is a plot illustrating bursts of electromyographic (EMG) activity that can be elicited by short-pulses of high-frequency electrical stimulation in accordance with an illustrative embodiment.

FIG. 18 is diagram of experimental results illustrating bursts of EMG activity elicited by short-pulses of high-frequency electrical stimulation (10 cycles, 10 kHz sine wave) to establish that placement of an electrode in the lumen of the intermuscular septum may provide a large window of electrical current that can be used to block saphenous nerve activity without causing co-excitation of nearby tissue. Specifically, FIG. 18 shows that the muscle activity elicited by short-bursts of high-frequency stimulation delivered to the intermuscular septum in the adductor canal is hosted by spinal reflexes and are not due to volume conduction or "co-excitation" of nearby muscle. To produce the results of FIG. 18, bursts of EMG activity were elicited by short-pulses of high-frequency electrical stimulation (10 cycles, 10 kHz sinewave). The stimulation was percutaneously delivered to the lumen of the intermuscular septum in the adductor canal via a cylindrical electrode (Model: Octrode; Abbott) operated in a monopolar fashion. Electromyogram (EMG) activity was recorded from the vastus medialis, vastus lateralis and sartorius muscles. Bursts of EMG were elicited with a minimum stimulation intensity of 25 mA (i.e., motor-threshold). Moreover, the bursts occurred about 164 ms post-stimulation. The exemplary method further established that placement of an electrode in the lumen of the intermuscular septum may provide a large window of electrical current that can be used to block saphenous nerve activity without causing co-excitation of nearby tissue.

Example #6

Figure 19:
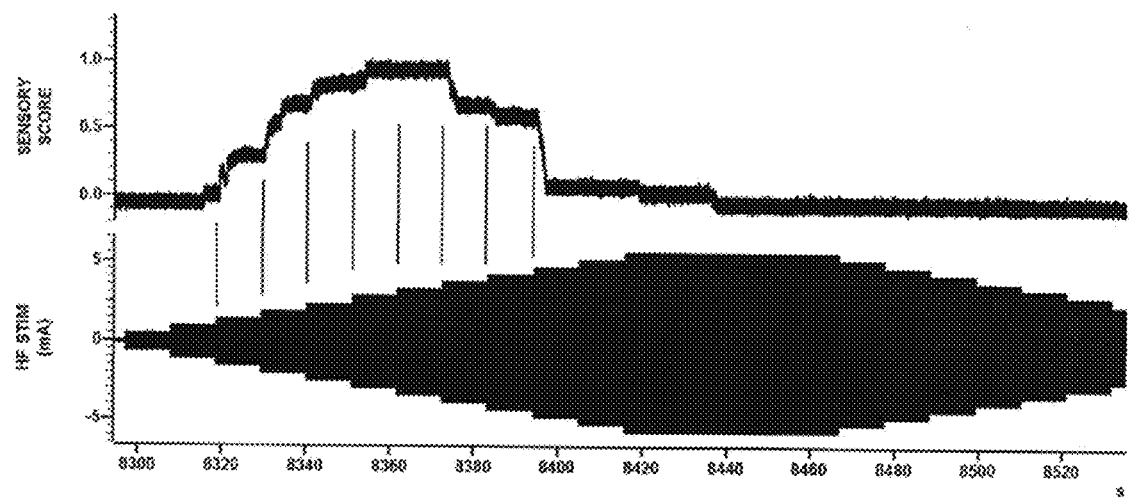
FIG. 19 is a plot showing an observed effect of having a discontinuity profile in the application of a high frequency electrical stimulation waveform to the saphenous nerve in accordance with an illustrative embodiment.

FIG. 19 demonstrates the effects of discontinuity in the application of a high-frequency electrical stimulation waveform being delivered to the saphenous nerve in an able-bodied subject. Indeed, as shown in FIG. 19, discontinuity in waveform amplitude and time were reliably detected by the subject as indicated by abrupt changes in sensory score. Indeed, a system and method that avoids such discontinuity (e.g., transient periods of discontinuity) is contemplated by the present embodiments.

Example Method of Treatment

Figure 20:
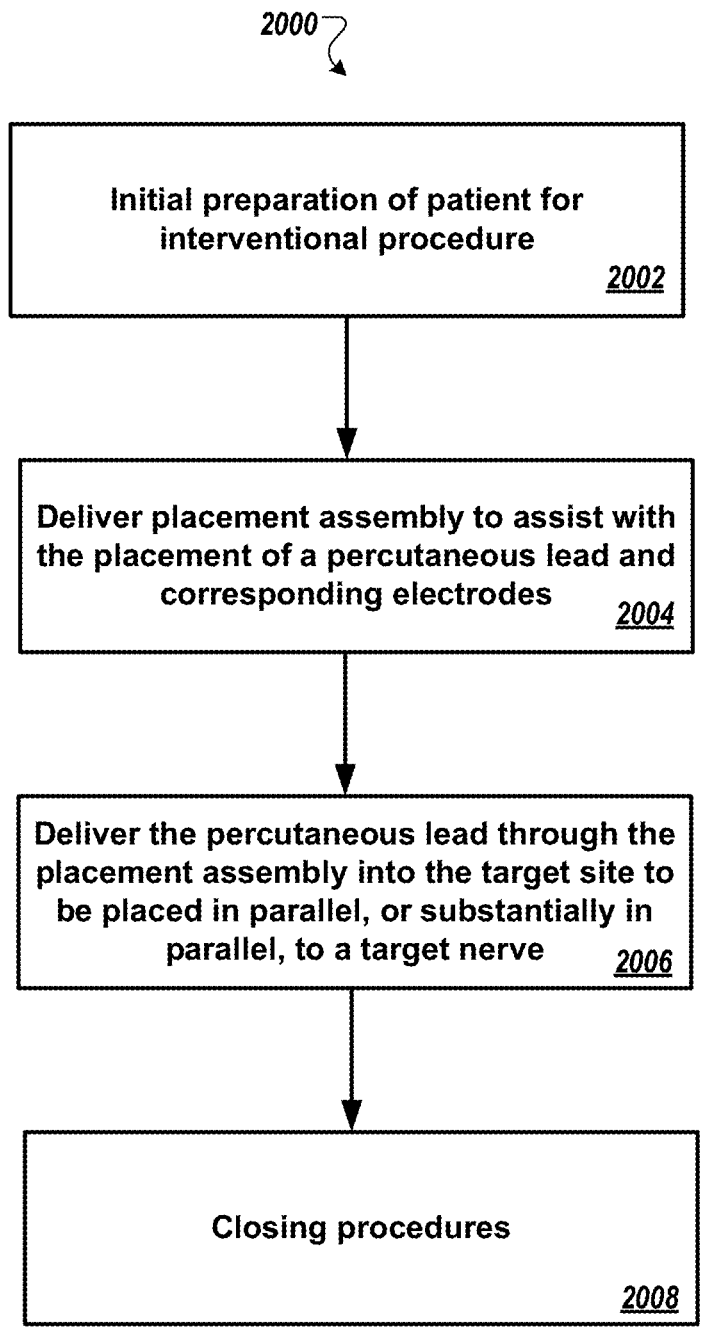
FIG. 20 is a diagram illustrating a method of treatment (e.g., for pain) to inhibit pain sensation using an exemplary electrical stimulation system to deliver high-frequency electrical stimulation to percutaneous leads placed in parallel, or substantially in parallel, and without direct contact, to a long axis of the peripheral nerve in accordance with an illustrative embodiment.

FIG. 20 is a diagram illustrating a method 2000 of treatment (e.g., for pain) to inhibit pain sensation using an exemplary high-frequency electrical stimulation system to deliver high-frequency electrical stimulation to percutaneous leads placed in parallel, or substantially in parallel, and without direct contact, to a long axis of the peripheral nerve in accordance with an illustrative embodiment. The method 2000 may be performed without an open surgical procedure. As shown in FIG. 20, the method 2000 includes an initial preparation (step 2002) of the patient for an interventional procedure. The initial preparation step may include pre-op preparation for the stimulator (e.g., 102, 202, etc.), percutaneous lead (e.g., 110), and return electrode as well as grounding the patient via application of a grounding electrode to the surface of the skin.

In some embodiments, the percutaneous lead is configured to operate with a central stylet that is inserted into a lumen of the percutaneous lead to stiffen the lead for insertion into the treatment site. The percutaneous lead may be assembled, in some embodiments, with the central stylet during the pre-op preparation. In other embodiment, the percutaneous lead is provided pre-assembled with the central stylet.

The initial preparation (e.g., 2002) may include imaging the region of interest, e.g., via ultrasound imaging, to identify the target nerve and the nerve region to block nerve conduction. With ultrasound imaging, the oblique view may be first used. The initial preparation step may include inserting a needle to deliver a local anesthetic along the anticipated lead-insertion path.

The method 2000 then include, in some embodiments, delivering (step 2004) a placement assembly to assist with the placement of the percutaneous lead (e.g., 110) and corresponding electrodes. The placement assembly, in some embodiments, is configured to receive a percutaneous lead inserted into an entry port of the placement assembly (e.g., a needle, introducer, or sheath) in which the percutaneous lead is placed at a first angle of insertion as defined with respect to an associated surface of the treatment site. The placement assembly then directs the percutaneous lead (e.g., 110) to a second angle that is parallel, or substantially parallel, to a long axis of a peripheral nerve to place the percutaneous electrodes of the leads over an overlapping nerve region of greater than about 3 mm. The first angle of insertion, in some embodiments, is between about 10 degrees and about 90 degrees with respect to the surface of the skin. In other embodiments, the first angle of insertion is between about 25 degrees and about 60 degrees, e.g., about 30 degrees. In some embodiments, the placement assembly is a needle. In other embodiments, the placement assembly is a Tuohy needle. In other embodiments, the placement assembly is an introducer. In some embodiments, the practitioner may ask the patient to provide an initial pain score associated with the pain area downstream to the treatment site. Further description of an example placement assembly/introducer that may be used in the procedure is disclosed in U.S. patent application Ser. No. 16/335,670, filed Mar. 15, 2019, entitled "Percutaneous Lead Placement Assembly," which is incorporated by reference herein in its entirety.

In some embodiments, the method step 2004 includes positioning the placement assembly (e.g., a curved Tuohy) into the target site. The positioning of the placement assembly may be performed while guided by ultrasound imaging. The placement of the placement assembly may include inserting the placement assembly into the target set and connecting the placement assembly to a stimulator (e.g., a signal waveform equipment that is used for this part of the procedure). The method step 2004 may then include stimulating the placement assembly to stimulate the target nerve to confirm placement and directing the distal end of the placement assembly in an orientation parallel to the target nerve. In some embodiments, the exemplary portable electrical stimulation system (e.g., 102, 202) is configured to generate a placement stimulation that is applied to the placement assembly. Indeed, the placement stimulation through the needle (i.e., placement assembly) is only used to guide the needle placement. In some embodiments, the practitioner may ask the patient to provide a pain score associated with the treatment site. Further description of delivery of the placement assembly is provided below.

The method 2000 includes delivering (step 2006) the percutaneous lead (e.g., 110) through the placement assembly into the target site. The step (2006) of delivering the percutaneous lead may include placing the distal end of the percutaneous lead (e.g., 110) into the placement assembly and advancing the lead to a first lead marker indicated on the percutaneous lead (e.g. 110). The step 2006 may then include re-orienting the ultrasound imager to image the regions parallel to the target nerve and then advancing the percutaneous lead to a specified or desired distance, e.g., up to a second lead marker indicated on the percutaneous lead. Indeed, the stylet as inserted, or fixed, inside the percutaneous lead (e.g., 110) may provide stiffness to the structure of the percutaneous lead to facilitate its insertion into the tissue. In some embodiments, the practitioner may ask the patient to provide an updated pain score associated with the pain area downstream to the treatment site and/or of the treatment site.

The method 2000 includes closing procedures (step 2008). The closing procedure may include removing the needle, stylet, needle, connection, and initial ground pad. Indeed, the stylet may be released from the locked state to be removed from the percutaneous lead. The closing procedure may include connecting the electrical connection of the percutaneous lead (e.g., 110) to a stimulator (e.g., the exemplary portable electrical stimulation system 102, 202). The stimulator may be activated to confirm placement location. In some embodiments, the practitioner may ask the patient to provide a pain score associated with the pain area downstream to the treatment site.

FIGS. 21A, 21B, 21C, and 21D are diagram illustrating example procedures of FIG. 20 of placing a percutaneous lead at a treatment site of a subject to block nerve conduction at the treatment site via an electrical stimulation (e.g., to provide pain therapy) in which an electrode of the lead is placed in parallel, or substantially in parallel to a long axis of a target nerve over an overlapping nerve region of greater than about 3 millimeter in accordance with an illustrative embodiment.

In FIG. 21A, a curved Tuohy 2020, as the placement assembly, is shown inserted (2022) into a treatment site 112 (shown as 112a), e.g., having located a target nerve 110 (shown as 110a). Prior to placement of the curved Tuohy 2020, as discussed above, the treatment site may be been treated, e.g., by local anesthetic, or scanned. In some embodiments, local anesthetic is introduced, e.g., via a needle, along an anticipated lead insertion path and the placement device may be guided by imaging (e.g., ultrasound).

To assist with the positioning of the curved Tuohy 2020, a stimulation may be applied to the curved Tuohy 2020 to identify when the tip of the curved Tuohy 2020 is next to or contacting the target nerve 110a.

In FIG. 21B, the curved Tuohy 2020 is shown connected to a stimulation source 2026 and a placement stimulation 2028 is applied to the curved Tuohy 2020 to apply a stimulus to it (e.g., to its tip). To this end, the medical practitioner or physician performing the insertion procedure can thus confirm placement and/or location (e.g., of the tip or a portion of the Tuohy) of the curved Tuohy 2020 at or relative to the target nerve 110a.

The curved Tuohy 2020 can then be used to assist/guide in the insertion of the percutaneous lead 110 (shown as 110a). In FIG. 21C, the percutaneous lead 11a (configured with one or more electrode(s) 2029) is shown inserted (2030) into the treatment site through the curved Tuohy 2020, e.g., to be placed in parallel, or substantially, in parallel to the target nerve 110a.

Following the insertion of the percutaneous lead 110a, the curved Tuohy 2020 can be retrieved leaving behind the percutaneous lead 110a at its inserted position. A stimulation, or a confirmation stimulation, may be applied (shown as 2032) via electrodes 2029 of the percutaneous lead 110a to confirm desired placement and/or positioning of the electrodes/leads in the therapeutic configuration. The stimulation 2032 may be a placement stimulation distinct from the therapeutic stimulation (e.g., 106). In some embodiments, the placement stimulation 2032 is the same as the therapeutic stimulation 106. In some embodiments, the stimulation source in FIG. 21D is the stimulation system (e.g., 102, 202) as described in the various embodiments herein. In other embodiments, the stimulation source in FIG. 21D is an external function generator.

In some embodiments, the medical practitioner or physician may ask the patient whether a pain sensation at a location downstream to the treatment site has ceased. In other embodiments, the medical practitioner or physician may introduce a sensory stimulus to a location downstream to the treatment site expected to be associated with the target nerve to confirm no sensory input being sensed there. Once placement of the percutaneous lead is confirmed, the treatment site can be closed and/or bandaged. The confirmation stimulation may be applied by the same stimulation source (e.g. 2026) used to confirm positioning of the placement assembly or by a different electrical source.

In some embodiments, the placement assembly is configured as a fixed-angle introducer having a gradual bend. The placement assembly may include a tip that facilitate advancement of the introducer into the tissue without the need of fluid injection, or other methods, to pre-open a space in the tissue to provides for passage of the percutaneous lead. The tip, or other portion, of the placement assembly may be conductive to facilitate application of an electrical stimulation to confirm placement of the placement assembly. Introducer subsystem includes, in some embodiments, a needle and an introducer. The needle can be removed from the introducer through which the percutaneous lead insertion can occur. The tip of the introducer may be angled with respect to the entry port to redirect the initial percutaneous lead insertion from the initial angle to a redirected angle between 10° and 90°, more specifically 25°-60°, for example 30°, to facilitate turning the electrodes to be parallel to the nerve.

In some embodiments, the redirection is caused by use of a needle or introducer with a fixed tip curve. In other embodiment, the redirection is caused by use of a sheath that is inserted through or around a straight needle/introducer. The sheath assumes a bent shape once the needle/introducer is retracted. In yet another embodiment, the redirection is via use of a needle/introducer which can be reversibly bent.

The placement assemblies and/or percutaneous lead may be provided in a kit for an electrical nerve block procedure. The kit may provide for articles and/or components. In some embodiments, the kit includes ECG and EMG electrodes may be included in the kit. The kit may include a container that may be, for example, a suitable tray having a removable sealed covering in which the articles are contained. In some embodiments, the kit may include drape, site dressings, tape, skin-markers. The kit, in some embodiments, may additionally include one or more containers of electrically conductive liquids or gels, antiseptics, and/or skin-prep liquids. The kit may include pre-packaged wipes such as electrically conductive liquid or gel wipes, antiseptic wipes, or skin-prep wipes. The kit may contain medicinal liquids and/or electrolytic solutions (e.g., the electrolytic solution may be or may include a bioresorbable gel material that is injected in liquid form but becomes substantially viscous or even solid-like after exiting the openings in the percutaneous electrode). In some embodiments, the kit includes a portable stimulator system (e.g., 102, 202) and corresponding cables (e.g., 108).

In some embodiments, the percutaneous lead (e.g., 110) may be used to deliver additional local anesthetic to the tip area of, or other areas along, the percutaneous lead. Indeed, a syringe may be connected to a connector of the percutaneous lead to deliver the local anesthetic to the lead. The treatment site may then be bandaged, and the treatment site closed. The practitioner may provide instructions on the operation of the stimulator and initiate delivery of the electrical stimulation, e.g., to treat the pain.

In some embodiments, the placement assembly is configured (e.g., suitably dimensioned and shaped) to be placed proximal to the mid-thigh saphenous nerve block, e.g., to treat post-surgical knee pain.

Example Method of Pain Treatment

Figure 22:
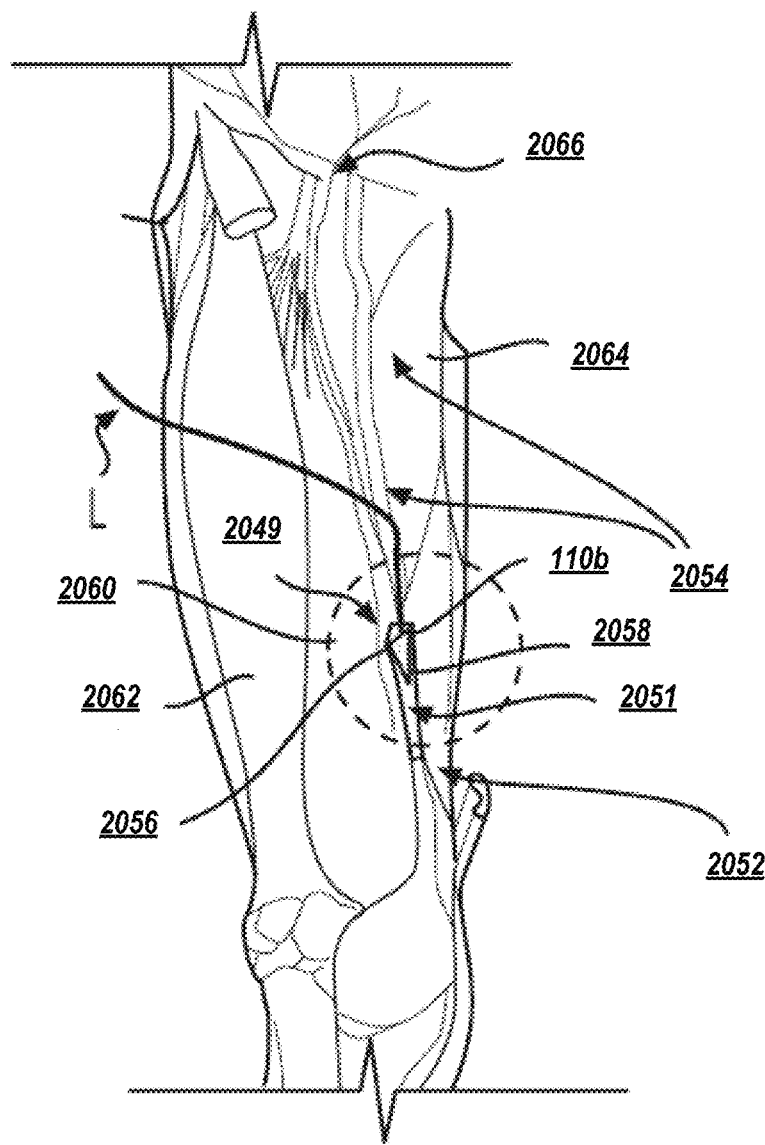
FIGS. 22, 23, and 24 show the exemplary nerve-blocking therapy being used for treating knee pain by blocking nerve-conduction of the saphenous nerve at the adductor canal via one or more electrodes. Other pain treatment therapy may be similarly performed using the method disclosed herein.
Figure 23:
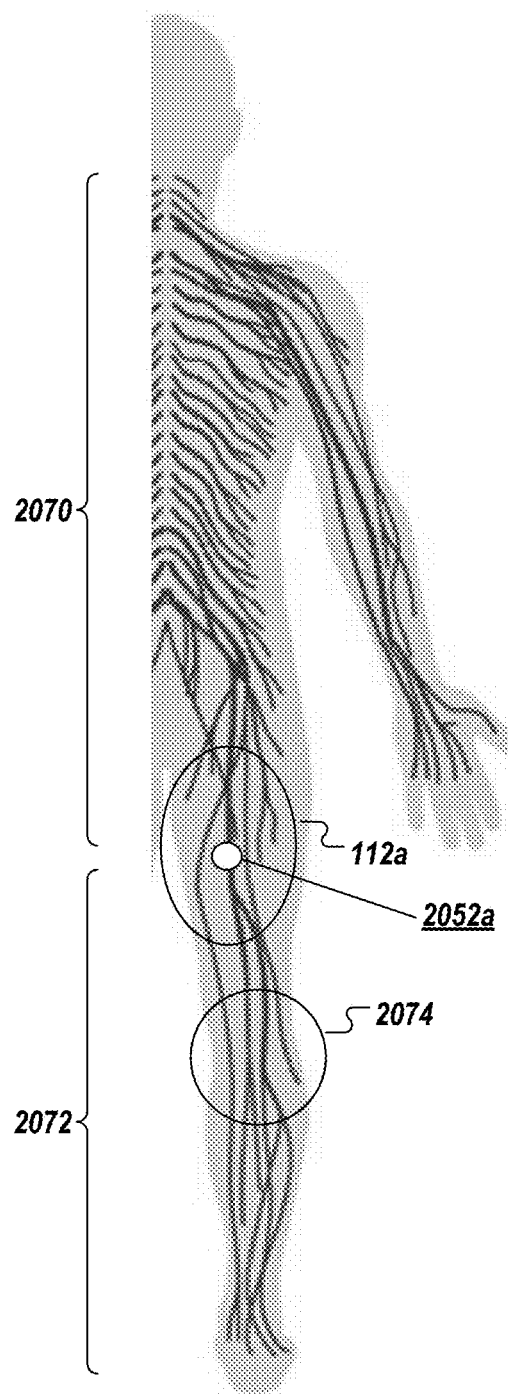
Figure 24:
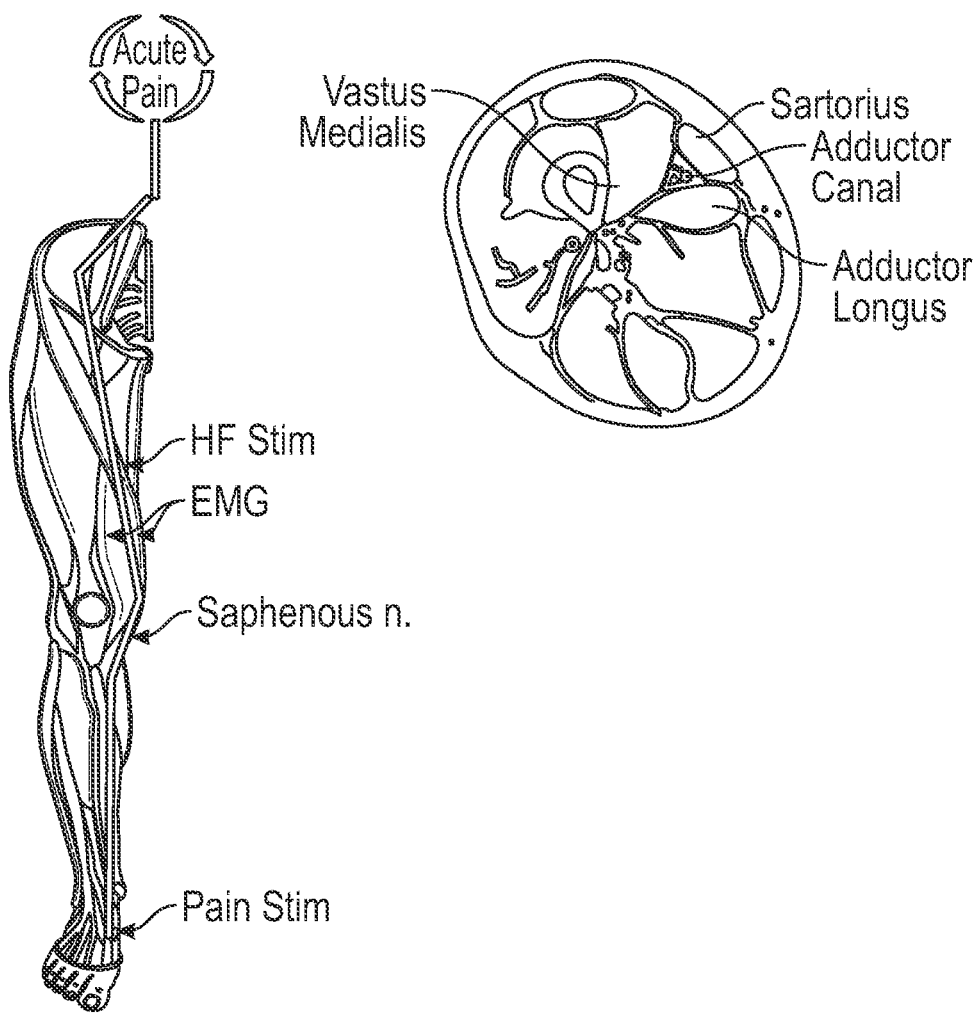

FIGS. 22, 23, and 24 show the exemplary nerve-blocking therapy being used for treating knee pain by blocking nerve-conduction of the saphenous nerve at the adductor canal via one or more electrodes. Other pain treatment therapy may be similarly performed using the method disclosed herein.

In FIG. 22, the percutaneous lead 110b is configured (i.e., suitable shaped and sized) to fit snugly within a cavity 2056 defined by the intermuscular septum 2058. Such a lead configuration can allow for the delivery of an immediately reversible nerve block of the saphenous nerve 2052 without evoking motor activity of the muscles forming the adductor canal 2054 (e.g., the sartorius 2060, vastus medialis 2062 and adductor longus 2064) due to volume conduction, thus allowing for therapeutic nerve conduction stimulation while reducing or eliminating muscle co-excitation. In addition, such a configuration can also prevent migration of the percutaneous electrode 110b within the adductor canal 2054. Moreover, because the percutaneous electrode 100b requires placement in the proximity of the saphenous nerve 2052, e.g., which may require penetration through the sartorius muscle 2060, the risk of accidental removal of the percutaneous electrode 100b by the patient is also mitigated (which may be a concern in a system that is being used to deliver a block over a time period, e.g., up to periods of several weeks).

Generally, selective modulation and blocking of saphenous nerve activity can be tailored to the anatomy of the adductor canal 2054. The adductor canal presents 2054, as an aponeurotic tunnel, is located in the middle third of the front of the thigh. It is located under the sartorius muscle 2060 and borders with the vastus medialis 2062 and adductor longus/magnus muscles 2064. The adductor canal 2054 contains the saphenous nerve 2052, the femoral nerve, artery and vein 2066 (see FIG. 22), and lymph nodes (not shown). In the distal anteromedial third of the thigh, the adductor canal 2054 is covered by the intermuscular septum (sub-sartorial fascia) 2058, which extends from the vastus medialis 2062 to the adductor longus/magnus 2064 muscles creating a triangular-shaped cavity or pocket 2056. This cavity or pocket 2056 is located at the distal third of the thigh and is about 5 centimeters to 6 centimeters long with the proximal opening of about 2 centimeters providing enough space for safe placement of the percutaneous lead 110b. Near this site, the saphenous nerve 2052 can have a diameter ranging from about 3 millimeters to about 4 millimeters. Structurally, the intermuscular septum 2058 is composed of connective tissue which may serve as an electrical isolator separating the saphenous nerve 2052 from surrounding excitable tissues. To this end, in preliminary EMG studies, high frequency electrical stimulation delivered to the saphenous nerve 2052 percutaneously at the intermuscular septum 2058 with large stimulation amplitudes up to 25 mA resulted in therapeutic nerve conduction stimulation with no co-excitation of nearby muscles.

As such, the percutaneous lead 110b (as well as 110 or 110a) can be inserted into the triangular-shaped cavity or pocket 2056 of the intermuscular septum 2058 covering the adductor canal 2054. The percutaneous 110b can be inserted along a direction corresponding to the saphenous nerve 2052 and at a location spaced a distance from the saphenous nerve 2052, such as a distance up to about 1.5 centimeters. The electrical stimulation to block painful sensations hosted by the saphenous nerve 2052 can be delivered to the saphenous nerve 2052 at the intermuscular septum 2058 of the adductor canal 2054, where the saphenous nerve 2054 can be modulated and blocked by percutaneous electrical stimulation without co-activation of nearby nerves and muscles, while at the same time preventing electrode migration within the adductor canal 2054. Further, the percutaneous electrode design utilized in the exemplary system and method allows for an straightforward and safe electrode removal, which can be conducted by a physician or a patient, thus allowing the use of the present embodiment in a single, in-patient or out-patient procedure lasting seconds-to-minutes that can be performed before or after a surgical procedure, where the system and method can be designed to deliver electrical stimulation after a surgical procedure that can last for hours to weeks and may include a complete or partial block of the target nerve (e.g., the saphenous nerve) for alleviation of acute and/or chronic pain, such as acute and/or chronic pain arising from the knee and/or the medial aspect of the leg and foot.

FIG. 23 further shows particular benefit of the treatment of pain using the method disclosed and referenced herein. In FIG. 23, the nerve-block conduction therapy is applied to the saphenous nerve (at a point 2052a) at a treatment location 112 (shown as 112a). Because the therapy can block nerve-conduction at the point 2052a, sensory function (and motor function, if applicable) above the point 2052a, i.e., upstream to point 2052a (shown as 2070), that are associated with the saphenous nerve and corresponding peripheral nerve are not affected. And, indeed, only sensory function below the point 2052a, i.e., downstream to the point 2052a (shown as 2072) and associated with the saphenous nerve are affected. To this end, post-surgical knee pain at a location downstream to the treatment site 112a (e.g., area 2072, including 2074) among other locations, can be treated using this method.

FIG. 24 shows an experiment associated with percutaneous method of treating pain via percutaneous electrodes placed in parallel orientation to a target nerve and stimulated via high-frequency electrical stimulation in accordance with an illustrative embodiment.

A study was performed on able-bodied human subjects (N=5) and underwent multiple trials of electrical stimulation. Acute pain sensations were elicited by electrical stimulation of the saphenous nerve at the ankle (see FIG. 24). High-frequency electrical stimulation comprising a 10 kHz fundamental frequency sinusoidal waveform was delivered to electrodes placed generally in parallel to the saphenous nerve at the adductor canal (see FIG. 24) via a percutaneous lead. Various high-frequency stimulation amplitudes (all ≤25 mA) and durations (seconds-to-minutes) were used. Outcome measures including acute pain score and muscle activity were recorded. In the study, subjects described their pain intensity on a 0-to-10 scale via a handheld potentiometer, where 3 was defined as the pain-threshold. Muscle activity was monitored both visually and by EMG recordings.

The study demonstrates the efficacy of high-frequency electrical stimulation of the saphenous nerve via a percutaneous electrode placed generally in parallel to the saphenous nerve in blocking acute pain sensations that were elicited distally and without eliciting unwanted contractions of the nearby muscles. The study further shows that blocking effects were titratable and reversible.

Indeed, the study concludes that percutaneous high-frequency electrical stimulation of a sensory nerve in the adductor canal, when delivered via percutaneous electrodes placed generally in parallel of the sensory nerve, can temporarily and reversibly block acute pain sensations in humans while doing so without causing co-excitation or stimulation of nearby muscles or tissues.

Further description of other experiments and results are described in U.S. patent application Ser. No. 16/335,673, filed Mar. 15, 2019, entitled "System and Method to Percutaneously Block Painful Sensations," which is incorporated by reference herein in its entirety. Other electrical waveform profile and configuration may be used, including those described in U.S. patent application Ser. No. 16/335,673, filed Mar. 15, 2019, entitled "System and Method to Percutaneously Block Painful Sensations," and in U.S. patent application Ser. No. 16/355,651, filed Mar. 15, 2019, entitled "System and Method to Percutaneously Block Painful Sensations," each of which is incorporated by reference herein in its entirety.

Example Percutaneous Lead

Figure 25A:
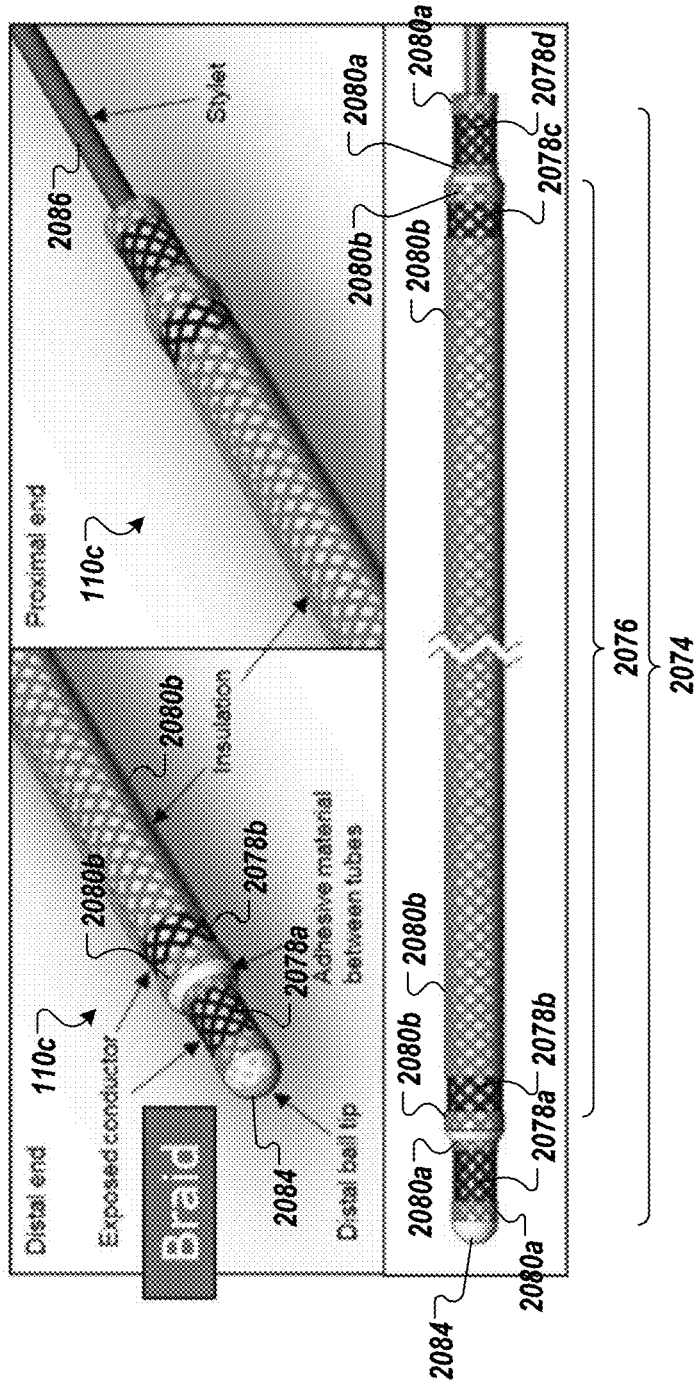
FIGS. 25A and 25B show exemplary percutaneous lead that can be used with the system and method described herein.
Figure 25B:

FIGS. 25A and 25B show an example percutaneous lead 110 (shown as 110c) that can be used with the exemplary portable electrical stimulation system (e.g., 102, 202, etc.) to perform the method described herein. The percutaneous lead 110c is particularly suitable for insertion, through tissue, in an intended orientation to be along one side of a long axis of a target nerve to orient electrodes located on the leads in parallel, or substantially in parallel, to the target nerve in accordance with an illustrative embodiment. As discussed herein, the percutaneous lead may be inserted through an introducer/needle.

To assist in advancing the percutaneous lead into the target tissue space parallel to the target nerve, the percutaneous lead 110c includes, in some embodiments, a removable stylet (e.g., a removable central stylet) that is inserted into a central region of the percutaneous lead to support, i.e., stiffen, the percutaneous lead during the insertion procedures. In some embodiments, the percutaneous lead is configured with a stiffness that facilitates advancement of the lead into the target tissue space parallel to the target nerve for a distance of up to 10 cm out of the needle. In some embodiments, the percutaneous lead has a stiffness that facilitates advancement of the lead i to the target tissue space for a distance of up to 4 cm out of the needle. In some embodiments, the percutaneous lead has a stiffness that facilitates advancement of the lead into the target tissue space for a distance of up to 3 cm out of the needle.

In some embodiments, the central stylet has a diameter between about 0.008" and 0.010". The central stylet may be made of stainless steel, tungsten, titanium, carbon, or other suitable medical grade material. The central stylet may be reversibly or irreversibly locked to the percutaneous lead to facilitate insertion.

In some embodiments, the percutaneous lead includes a clamp to reversible lock with the central stylet. The clamp creates friction between a lead lumen and the stylet. In some embodiments, the central stylet includes the clamp.

Alternatively, or in combination with, the percutaneous lead includes metal reinforcement of the electrode body to provide the desired stiffness to advance the lead into the target tissue space parallel to the target nerve for a distance of up to 10 cm out of a needle.

In FIG. 25A, a functional schematic of a percutaneous lead 110c is shown, the percutaneous lead 110c is configured with braided electrodes to be delivered parallel, or substantially in parallel, to a long axis of a target nerve in accordance with another illustrative embodiment. FIG. 25B shows another example of the percutaneous lead 110c having proportions for use as described herein, e.g., with peripheral nerves (e.g., saphenous nerve).

The percutaneous lead 110c may be configured with one or more tube members in which each tube members (e.g., 2074, 2076) includes an inner conductive layer 2078 (shown as 2078a, 2078b) that is partially or completely surrounded an external insulated layer 2080 (shown as 2080a, 2080b) to form an electrode pair. The inner conductive layer 2078 and outer insulated 2080 are configured as coaxial tubes, in some embodiments, with one electrode-contact pair formed per tube. In other embodiments, only a single electrode-contact is formed per tube. In yet other embodiments, the inner conductive layer 2078 and outer insulated 2080 are configured to form multiple electrode regions. The inner conductive layers 2078 (shown as 2078c, 2078d) are exposed, in some embodiments, at a proximal end of the percutaneous lead 110c to provide location for electrical contact and connection to a stimulator system (e.g., 102, 202, etc.). In some embodiments, the longitudinal body of the percutaneous lead 100c has a length sufficient to allow placement of the electrodes of the lead 110c (and associated electrodes) in the parallel orientation to the target nerve and to provide access for electrical connection to the contacts (e.g., 2078c and/or 2078d) outside the body. In other embodiments, the inner conductive layers 2078 of each of the tube members are coupled to a lead-wire (not shown) that provide electrical connection to the contacts.

Insulation of the wire tube may occur through insulation of individual wire(s), or by embedding the conductive tubing in insulated tubing. In some embodiments, each individual wire may be encapsulated to form the inner conductive layer 2078 and outer insulated 2080. In other embodiments, a single outer insulated 2080 is encapsulated over a coiled inner conductive layer. Examples of the coiled conductive layer embodiment, among other embodiments, are provided in U.S. patent application Ser. No. 16/335,660, filed Mar. 15, 2019, entitled "Percutaneous Lead," which is incorporated by reference herein in its entirety. Examples of other leads, among other things, are described WO/2016/032929, which is incorporated by reference herein in its entirety.

In some embodiments, wires may be close-packed, with no space between coils (e.g., a closed coil), or open, with a space between adjacent coils (e.g., with uniform or non-uniform spacing between adjacent coils) along the length of the lead to enable, for example, as anti-migration measures or ultrasound visibility.

In some embodiments, the percutaneous lead forms a full braid assembly comprising a longitudinal body that includes two or more coaxial conducting members in which each member includes multiple conductors (e.g., steel ribbon, carbon ribbon, platinum ribbon, carbon, etc.) interlaced and formed into a mesh tube embedded in a polymer and in which each tube has one or more exposure regions defined by the polymer. Further description of the braided conductive layer embodiment, among other embodiments, are provided in U.S. patent application Ser. No. 16/335,660, filed Mar. 15, 2019, entitled "Percutaneous Lead," which is incorporated by reference herein in its entirety.

Indeed, the percutaneous lead (e.g., 110, 110a, 110b, 110c) may form two or more electrodes configured to operate in bipolar fashion in which at least one of the electrode serves as the cathode and another electrodes serves as the return anode. In other embodiments, the percutaneous lead (e.g., 110, 110a, 110b, 110c) forms a single electrode with an electrical return being provided through a surface electrode placed on the skin. In yet another embodiment, the percutaneous lead (e.g., 110, 110a, 110b, 110c) is configured with or more than two electrodes to operate in a multipolar operation. The multiple electrodes may be used for electrode positional tuning and/or current steering.

Referring still to FIG. 25A, the conductive material of the inner conductive layer 2078, in some embodiments, forms one or more electrode site(s) (shown as 2078a, 2078b) intended to reside parallel to the target nerve to deliver electrical therapy. The external insulated layer 2080 (e.g., 2080a, 2080b) encapsulates the inner conductive layer 2078 (e.g., 2078a, 2078b) and includes openings to expose the portions of the inner conductive layer 2078a, 2078b that define the electrodes.

Tubes (e.g., 2074, 2076) may comprise coiled wire(s) with a specified wire count and/or coil pitch, formed into a tube of a given inner and outer diameter. The wires may be flat or rounded. Coiled wires may be crossed over one another to form a braided mesh. In other embodiments, a braided mesh is formed as a single unitary structure that is affixed to the tube.

In some embodiments, the conductive material is exposed at contact site(s) (e.g., 2078c, 2078d) residing outside the body of the patient and connect to cabling that transmits the treatment waveform from a waveform generator to the implanted electrode(s).

Referring still to FIG. 25A, the percutaneous lead (e.g., 110, 110a, 110b, 110c) is configured with a continuous individual electrodes. In other embodiments, the percutaneous lead (e.g., 110, 110a, 110b, 110c) is configured with multiple electrode segments in which the segments have a specified length and distance between them. For example, an electrode comprising of 3 segments may have an electrode length of 1 mm each in which each is separated by space of 4 mm to provide a lead length of about 11 mm.

The percutaneous lead (e.g., 110, 110a, 110b, 110c) may be configured with an electrode length between about 1 mm and about 10 cm, e.g., between about 3 mm and about 10 mm. For multiple electrodes on the lead body, the electrodes may be separated by a space of 1 mm to 10 cm, for example 10 mm.

Referring still to FIG. 25A, the inner conductive layer 2078 (e.g., of layers 2074 or 2076) may be made of a metal such as 304 or 316 stainless steel, platinum, carbon, and other suitable medical-grade electrode material, and the outer insulated layers 2080 is made of a polymer such as polyimide, Pebax®, or other suitable medical-grade insulators.

Referring still to FIG. 25A, the distal end of the percutaneous lead (e.g., 110, 110a, 110b, 110c) includes a ball tip 2084. The ball tip 2084 facilitates advancement of the percutaneous lead (e.g., 110, 110a, 110b, 110c) into the tissue by minimizing the likelihood of it piercing and/or damaging a blood vessel or nerve trunk.

The percutaneous lead (e.g., 110, 110a, 110b, 110c) includes a central stylet 2086 that stiffens the elongated wall of the percutaneous lead (e.g., the first and second members 2076, 2078). In some embodiments, the central stylet 2086 is fixably connected into a lumen of the percutaneous lead (e.g., 110, 110a, 110b, 110c) (e.g., the inner surface of the first member 2074). In other embodiments, the central stylet 2086 is removeable having a clamp that fixes the central stylet 2086 to the lumen of the percutaneous lead (e.g., 110, 110a, 110b, 110c) (e.g., the inner surface of the first member 2074) when engaged.

In general, regardless of its particular design, the percutaneous electrode ensemble may deliver stimulation in a monopolar fashion or mode. In this monopolar mode, one or more stimulating electrode(s) is positioned over the target nerve and a second dispersive electrode with a relatively larger surface area is positioned on a surface of the patient's body to complete the circuit. Alternatively, the stimulation may be delivered in a bipolar fashion or mode and the above-described system may further include one or more anodes, where each anode can be present on the percutaneous electrode or, alternatively, can be disposed on a skin contacting surface. When the stimulation is delivered in a bipolar fashion or mode, the one or more electrode(s) (also referred to as a "cathode(s)" is positioned near or adjacent the target nerve percutaneously and one or more anode(s) is positioned near or adjacent the target nerve percutaneously or, alternatively, on the skin over the target nerve to preferentially concentrate the delivery of electrical energy between the cathode(s) and anode(s). In either mode, the electrodes should be positioned a sufficient distance away from each other, to avoid shunting and a possible short-circuit. The tissue contacting surface or skin contacting surface of each anode will desirably have at least the same or greater surface area as the tissue contacting surface of the stimulating electrode(s).

Other percutaneous leads and configurations may be used including those described in U.S. patent application Ser. No. 16/335,660, filed Mar. 15, 2019, entitled "Percutaneous Lead," which is incorporated by reference herein in its entirety.

In some embodiments, single electrode contact may be used. In other embodiments, multiple electrode contacts (e.g., from about 2 to 20 contacts, such as from about 4 to 16 contacts, such as from about 6 to 12 contacts) can be utilized.

It is appreciated that certain features of the embodiment, which are, for clarity, described in the context of separate embodiments, may also be provided in combination in a single embodiment. Conversely, various features of the embodiment, which are, for brevity, described in the context of a single embodiment, may also be provided separately or in any suitable sub-combination.

Although the embodiment has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present embodiment.

What is claimed is:

1. A portable electrical stimulation system configured to percutaneously block nerve conduction, the system comprising:
   a modular power source;
   a switching circuit coupled to said modular power source and configured to continuously generate at an output of said switching circuit an electrical stimulation output at a plurality of selectable output level that span over a range of output levels that can block nerve conduction at a target site of a subject, and a controller coupled to the switching circuit, the switching circuit having one or a programmable output level, wherein the output of the switching circuit is coupled to one or more electrodes, directly or through a cable, located at or in proximity to, the target site, wherein the one or more electrodes are adapted to be placed in parallel, or substantially in parallel to a long axis of the peripheral nerve over an overlapping nerve region of greater than about 3 millimeters, and wherein the switching circuit is configured to continuously generate the electrical stimulation output at an output efficiency greater than 70%, wherein the output efficiency is a ratio of the electrical stimulation output from the switching circuit to an electrical input from the modular power source to the switching circuit.

2. The portable electrical stimulation system of claim 1, wherein the switching circuit is configured to continuously generate the electrical stimulation output at an output efficiency greater than 90%.

3. The portable electrical stimulation system of claim 1, wherein the switching circuit comprises a switching stage and a filter stage, the switching stage being configured to generate a square-wave or pulse-shaped amplitude modulated output, the filter stage being configured to shape the square wave or pulse-shaped amplitude modulated output to a sinusoidal waveform.

4. The portable electrical stimulation system of claim 3, wherein the filter stage includes inductive and capacitive components with a high-quality factor at an operating frequency output of the sinusoidal waveform between 1.5 kHz and 75 kHz.

5. The portable electrical stimulation system of claim 3, wherein the switching circuit comprises a variable output power source, the variable output power source comprising a linear regulator configured to vary the power source to the switching stage to vary the amplitude of the square-wave amplitude modulated output or the pulse-shaped amplitude modulated output.

6. The portable electrical stimulation system of claim 3, wherein the switching circuit comprises a variable output power source, the variable output power source comprising a switching power regulator or a linear regulator to vary the power source to the switching stage to vary the amplitude of the square-wave amplitude modulated output or the pulse-shaped amplitude modulated output.

7. The portable electrical stimulation system of claim 3, wherein the switching circuit comprises one or more feedback loops, the controller being configured to vary the pulse-shaped or square-shaped amplitude modulated output based on a detected envelope of the square-wave amplitude modulated output or the pulse-shaped amplitude modulated output.

8. The portable electrical stimulation system of claim 1, further comprising:

a second modular power source, wherein the second modular power source has sufficient stored electrical energy to continuously generate the electrical stimulation output for a temporary period; and a breaker to connect the switching circuit to the second modular power source and to isolate the modular power source during the temporary period without interruption.

9. The portable electrical stimulation system of claim 1, wherein the controller comprises a display, the controller being configured to present, via the display, the selected output level or a monitored output level of the electrical stimulation output.

10. The portable electrical stimulation system of claim 1, wherein the controller comprises a speaker, the controller being configured to monitor for interruption of the electrical stimulation output when operating in a stimulation mode, and to generate an audible alert, via the speaker, upon detection of an interruption of the electrical stimulation output while in the stimulation mode.

11. The portable electrical stimulation system of claim 1, wherein the switching circuit comprises a circuit to detect phasor magnitude load impedance between a pair of electrodes, and wherein the controller is configured to monitor a detected phasor magnitude load impedance and to output an alert when the detected phasor magnitude load impedance exceeds a specified threshold, and wherein the controller is configured to vary one or more control parameters associated with the electrical stimulation output based on the detected phasor magnitude load impedance.

12. The portable electrical stimulation system of claim 1, wherein the switch circuit comprises a first fault safety switch at a first output and a second fault safety switch at a second output, wherein each of the first fault safety switch and the second fault safety switch is configured to isolate the switch circuit from the pair of electrodes.

13. The portable electrical stimulation system of claim 1, wherein the switch circuit comprises a fault safety switch, wherein the fault safety switch is coupled between the modular power source and active output components to isolate the power source from the active output components and the electrode circuits when a circuit fault is detected.

14. The portable electrical stimulation system of claim 1, wherein the controller comprises a display and a monitoring circuit, wherein the monitoring circuit is configured to monitor a battery state of the modular power source, and wherein the controller is configured to present, via the display, a remaining battery life or a remaining operating time based on the monitored battery state.

15. The portable electrical stimulation system of claim 1, wherein the controller comprises persistent, non-volatile memory, the controller being configured to log, at predefined intermittent duration, one or more parameters selected from the group consisting of a first set of one or more parameters associated with the electrical stimulation output, a second set of one or more parameters associated with switching circuit, controller, or modular power source, a third set of one or more parameters associated with lead coupled to the switching circuit, a fourth set of one or more parameters associated with electrodes coupled to the switching circuit, and a fifth set of one or more parameters associated with software status.

16. The portable electrical stimulation system of claim 1, wherein the switch circuit comprises a high impedance differential voltage sensing circuit and a variable DC current injection circuit, wherein the differential voltage sensing circuit is configured to measure differential DC voltage at the pair of electrodes, and wherein the variable DC current injection circuit is configured to inject a current between the pair of electrodes to counteract any excess DC voltages based on the measured differential DC voltage.

17. The portable electrical stimulation system of claim 1, wherein the switch circuit is configured to continuously output the electrical stimulation output over, at least, a 24-hour duration using the modular power source without replacement or recharge of the modular power source.

18. The portable electrical stimulation system of claim 1, comprising:
   one or more bypass filter circuits coupled to the switch circuits, and
   a connection element coupled to the one or more bypass filter circuits, wherein the connection element is configured to be coupled to electrodes, directly or through the cable, with the electrodes, wherein the square wave amplitude modulated output or pulse-shaped amplitude modulated output can be sent directly to tissue for detecting nerve location and ideal electrode placement.

19. The portable electrical stimulation system of claim 1, wherein the one or more electrodes do not directly contact a portion of the peripheral nerve at the overlapping nerve region and is in proximity to the overlapping nerve region by less than about 15 millimeters.

\* \* \* \* \*